(12) United States Patent
Herranz et al.

(10) Patent No.: US 8,340,245 B2
(45) Date of Patent: Dec. 25, 2012

(54) TRANSPORTATION CONTAINER INSPECTION SYSTEM AND METHOD

(75) Inventors: Michel Herranz, Salamanca (ES); Luis Roso Franco, Salamanca (ES); Francisco Martin Labajos, Salamanca (ES); Belen Curto, Salamanca (ES)

(73) Assignee: Sentinel Scanning Corporation, Myersville, MD (US)

( * ) Notice: Subject to any disclaimer, the term of this patent is extended or adjusted under 35 U.S.C. 154(b) by 115 days.

(21) Appl. No.: 12/802,538

(22) Filed: Jun. 7, 2010

(65) Prior Publication Data

US 2011/0058646 A1    Mar. 10, 2011

Related U.S. Application Data

(60) Provisional application No. 61/184,449, filed on Jun. 5, 2009, provisional application No. 61/251,592, filed on Oct. 14, 2009.

(51) Int. Cl.
*G01N 23/04* (2006.01)
(52) U.S. Cl. .............................. 378/57; 378/4
(58) Field of Classification Search ................ 378/4, 19, 378/57, 98.2, 98.8
See application file for complete search history.

(56) References Cited

U.S. PATENT DOCUMENTS

| | | | |
|---|---|---|---|
| 2,209,963 A | 8/1940 | Du Mond | |
| 2,539,196 A | 1/1951 | Marshall | |
| 2,586,304 A * | 2/1952 | Coltman et al. | 313/527 |
| 3,018,374 A | 1/1962 | Pritchett | |
| 3,636,353 A | 1/1972 | Untmermeyer | |
| 3,862,450 A * | 1/1975 | Mossman | 313/396 |
| RE28,544 E | 9/1975 | Stein et al. | |

(Continued)

FOREIGN PATENT DOCUMENTS

EP         1 319 963        12/2001
(Continued)

OTHER PUBLICATIONS

International Search Report & the Written Opinion of the International Application No. PCT/US10/01643, International Filing Date Jun. 7, 2010, Dated Oct. 13, 2010.

(Continued)

*Primary Examiner* — Glen Kao
(74) *Attorney, Agent, or Firm* — Merchant & Gould P.C.

(57) ABSTRACT

In exemplary embodiments of the present invention, containers, such as, for example, those used in transportation and shipping, can be inspected by using a CT X-ray scanning system with a large area detector plate. In exemplary embodiments of the present invention the detector plate can directly convert X-rays transmitted through the container into visible light, thus forming light patterns on the outer surface of the plates. The plates can then be analyzed using, for example, CCD or ICCD cameras and a data processor so as to form real-time 2D and/or 3D images of objects in the container. In exemplary embodiments of the present invention each such plate can comprise a coating of X-ray converting material such as, for example, a phosphor on a metallic plate. In exemplary embodiments of the present invention an exemplary scanning system can, for example, rotate a rotor having an X-ray source on one side of an axis of rotation, and a detector including such detector plates on the other side of the axis. In exemplary embodiments of the present invention a container can be moved, through an opening in the rotor and support structure in synchronization with the rotor, such as, for example, by transporting the container on rails.

11 Claims, 36 Drawing Sheets

U.S. PATENT DOCUMENTS

| | | | |
|---|---|---|---|
| 3,924,132 A | 12/1975 | Koslow | |
| 4,031,545 A | 6/1977 | Stein et al. | |
| 4,149,081 A | 4/1979 | Seppi | |
| 4,158,142 A | 6/1979 | Haimson | |
| 4,196,352 A | 4/1980 | Beringer et al. | |
| 4,229,654 A | 10/1980 | Arya et al. | |
| 4,251,726 A | 2/1981 | Alvarez | |
| 4,258,264 A | 3/1981 | Kotera et al. | |
| 4,346,295 A | 8/1982 | Tanaka et al. | |
| 4,352,021 A | 9/1982 | Boyd et al. | |
| 4,357,535 A | 11/1982 | Haas | |
| 4,430,568 A | 2/1984 | Yoshida et al. | |
| 4,439,866 A | 3/1984 | Kato et al. | |
| 4,485,481 A | 11/1984 | Takano | |
| 4,521,900 A | 6/1985 | Rand | |
| 4,531,226 A | 7/1985 | Peschmann | |
| 4,571,493 A | 2/1986 | Horikawa | |
| 4,573,179 A | 2/1986 | Rutt | |
| 4,591,714 A | 5/1986 | Goto et al. | |
| 4,599,740 A | 7/1986 | Cable | |
| 4,631,741 A | 12/1986 | Rand et al. | |
| 4,671,256 A | 6/1987 | Lemelson | |
| 4,722,096 A | 1/1988 | Dietrich et al. | |
| 4,736,396 A | 4/1988 | Boyd et al. | |
| 4,767,927 A | 8/1988 | Ohyama et al. | |
| 4,809,312 A | 2/1989 | Annis | |
| 4,812,660 A | 3/1989 | Lindmayer | |
| 4,818,876 A | 4/1989 | Agano et al. | |
| 4,822,520 A | 4/1989 | Lindmayer | |
| 4,825,454 A | 4/1989 | Annis et al. | |
| 4,839,092 A | 6/1989 | Lindmayer | |
| 4,842,960 A | 6/1989 | Lindmayer | |
| 4,879,186 A | 11/1989 | Lindmayer | |
| 4,918,315 A | 4/1990 | Gomberg et al. | |
| 4,941,162 A | 7/1990 | Vartsky et al. | |
| 4,952,814 A | 8/1990 | Huntzinger | |
| 4,956,856 A | 9/1990 | Harding | |
| 4,963,746 A | 10/1990 | Morgan et al. | |
| 4,964,148 A | 10/1990 | Klostermann et al. | |
| 4,987,584 A | 1/1991 | Doenges | |
| 4,989,225 A * | 1/1991 | Gupta et al. | 378/10 |
| 5,007,072 A | 4/1991 | Jenkins et al. | |
| 5,014,293 A | 5/1991 | Boyd et al. | |
| 5,023,895 A * | 6/1991 | McCroskey et al. | 378/4 |
| 5,044,002 A | 8/1991 | Stein | |
| 5,065,023 A | 11/1991 | Lindmayer | |
| 5,065,418 A | 11/1991 | Bermbach et al. | |
| 5,076,993 A | 12/1991 | Sawa et al. | |
| 5,097,494 A | 3/1992 | Pantelleria et al. | |
| 5,098,640 A | 3/1992 | Gozani et al. | |
| 5,115,459 A | 5/1992 | Bertozzi | |
| 5,124,554 A | 6/1992 | Fowler et al. | |
| 5,124,658 A | 6/1992 | Adler et al. | |
| 5,138,642 A * | 8/1992 | McCroskey et al. | 378/19 |
| 5,153,439 A | 10/1992 | Gozani et al. | |
| 5,182,764 A * | 1/1993 | Peschmann et al. | 378/57 |
| 5,185,774 A | 2/1993 | Klostermann et al. | |
| 5,197,088 A | 3/1993 | Vincent et al. | |
| 5,200,626 A | 4/1993 | Schultz et al. | |
| 5,278,418 A | 1/1994 | Broadhurst | |
| 5,313,511 A | 5/1994 | Annis et al. | |
| 5,367,552 A | 11/1994 | Peschmann | |
| 5,410,156 A | 4/1995 | Miller | |
| 5,420,905 A | 5/1995 | Bertozzi | |
| 5,440,133 A | 8/1995 | Moyers et al. | |
| 5,444,756 A * | 8/1995 | Pai et al. | 378/98.8 |
| 5,469,487 A | 11/1995 | Hu | |
| 5,471,516 A | 11/1995 | Nunan | |
| 5,490,193 A | 2/1996 | Kuroda et al. | |
| 5,490,218 A | 2/1996 | Krug et al. | |
| 5,491,734 A | 2/1996 | Boyd et al. | |
| 5,493,596 A | 2/1996 | Annis | |
| 5,495,106 A | 2/1996 | Mastyny | |
| 5,513,236 A | 4/1996 | Hui | |
| 5,524,133 A | 6/1996 | Neale et al. | |
| 5,541,970 A | 7/1996 | Hu | |
| 5,557,108 A | 9/1996 | Tumer | |
| 5,559,847 A | 9/1996 | Hu et al. | |
| 5,600,303 A | 2/1997 | Husseiny et al. | |
| 5,600,700 A | 2/1997 | Krug et al. | |
| 5,606,585 A | 2/1997 | Hu | |
| 5,611,502 A | 3/1997 | Edlin et al. | |
| 5,638,420 A | 6/1997 | Armistead | |
| 5,642,394 A | 6/1997 | Rothschild | |
| 5,692,028 A | 11/1997 | Geus et al. | |
| 5,692,029 A | 11/1997 | Husseiny et al. | |
| 5,696,806 A | 12/1997 | Grodzins et al. | |
| 5,712,889 A | 1/1998 | Lanzara et al. | |
| 5,729,582 A | 3/1998 | Ham et al. | |
| 5,772,916 A | 6/1998 | Jamil et al. | |
| 5,818,054 A | 10/1998 | Randers-Pehrson et al. | |
| 5,828,719 A | 10/1998 | He et al. | |
| 5,838,758 A | 11/1998 | Krug et al. | |
| 5,838,759 A | 11/1998 | Armistead | |
| 5,841,832 A | 11/1998 | Mazess et al. | |
| 5,901,198 A | 5/1999 | Crawford et al. | |
| 5,917,880 A | 6/1999 | Bjorkholm | |
| 5,930,326 A | 7/1999 | Rothschild et al. | |
| 5,966,422 A | 10/1999 | Dafni et al. | |
| 5,970,113 A | 10/1999 | Crawford et al. | |
| 5,974,111 A | 10/1999 | Krug et al. | |
| 5,983,671 A | 11/1999 | Haines et al. | |
| 6,009,146 A | 12/1999 | Adler et al. | |
| 6,018,562 A | 1/2000 | Willson | |
| 6,041,097 A | 3/2000 | Roos et al. | |
| 6,078,642 A | 6/2000 | Simanovsky et al. | |
| 6,088,423 A | 7/2000 | Krug et al. | |
| 6,110,398 A | 8/2000 | Jamil et al. | |
| 6,151,381 A | 11/2000 | Grodzins et al. | |
| 6,218,943 B1 | 4/2001 | Ellenbogen | |
| 6,236,709 B1 | 5/2001 | Perry et al. | |
| 6,249,567 B1 | 6/2001 | Rothschild et al. | |
| 6,256,404 B1 | 7/2001 | Gordon et al. | |
| 6,259,762 B1 | 7/2001 | Pastyr et al. | |
| 6,269,142 B1 | 7/2001 | Smith | |
| 6,278,115 B1 | 8/2001 | Annis et al. | |
| 6,292,533 B1 | 9/2001 | Swift et al. | |
| 6,347,132 B1 | 2/2002 | Annis | |
| 6,411,673 B1 | 6/2002 | Bromberg et al. | |
| 6,411,674 B1 | 6/2002 | Oikawa | |
| 6,416,960 B1 * | 7/2002 | Bryan | 435/7.23 |
| 6,438,201 B1 | 8/2002 | Mazess et al. | |
| 6,449,334 B1 | 9/2002 | Mazess et al. | |
| 6,452,117 B2 | 9/2002 | Curcio et al. | |
| 6,490,337 B1 | 12/2002 | Nagaoka et al. | |
| 6,542,574 B2 | 4/2003 | Grodzins | |
| 6,555,838 B1 | 4/2003 | Livingston et al. | |
| 6,600,855 B2 | 7/2003 | Werkheiser et al. | |
| 6,625,376 B2 | 9/2003 | Werkheiser et al. | |
| 6,628,745 B1 | 9/2003 | Annis et al. | |
| 6,668,033 B1 | 12/2003 | Schelten | |
| 6,680,790 B2 | 1/2004 | Johnson et al. | |
| 6,687,328 B2 | 2/2004 | Bavendiek et al. | |
| 6,696,698 B2 | 2/2004 | Livingston | |
| 6,713,777 B2 | 3/2004 | Karasawa | |
| 6,735,271 B1 | 5/2004 | Rand et al. | |
| 6,800,858 B1 | 10/2004 | Seppi | |
| 6,800,870 B2 | 10/2004 | Sayag | |
| 6,842,499 B2 | 1/2005 | Zapalac | |
| 6,861,661 B2 | 3/2005 | Nakajim et al. | |
| 6,865,333 B2 | 3/2005 | Porter et al. | |
| 6,894,303 B2 | 5/2005 | Livingston | |
| 6,963,678 B2 | 11/2005 | Werkheiser et al. | |
| 6,965,661 B2 | 11/2005 | Kojima et al. | |
| 6,998,632 B2 | 2/2006 | Magne et al. | |
| 7,020,232 B2 | 3/2006 | Rand et al. | |
| 7,050,536 B1 | 5/2006 | Fenkart et al. | |
| 7,082,186 B2 | 7/2006 | Zhao et al. | |
| 7,102,149 B2 | 9/2006 | Kuroda et al. | |
| 7,103,137 B2 | 9/2006 | Seppi et al. | |
| 7,112,807 B2 | 9/2006 | Yonekawa | |
| 7,164,747 B2 | 1/2007 | Ellenbogen et al. | |
| 7,170,079 B2 | 1/2007 | Fasbender et al. | |
| 7,286,630 B2 | 10/2007 | Holt | |
| 2003/0215055 A1 | 11/2003 | Ozawa et al. | |
| 2004/0258196 A1 | 12/2004 | Lounsberry | |
| 2005/0243321 A1 | 11/2005 | Cohen et al. | |

| | | | |
|---|---|---|---|
| 2006/0126772 | A1 | 6/2006 | Hu et al. |
| 2006/0237653 | A1 | 10/2006 | Popescu |
| 2006/0280286 | A1* | 12/2006 | Kaval .............................. 378/57 |
| 2007/0003003 | A1 | 1/2007 | Seppi et al. |
| 2007/0140414 | A1 | 6/2007 | Garms et al. |
| 2007/0147586 | A1 | 6/2007 | Scheinman et al. |
| 2007/0172020 | A1 | 7/2007 | Nambu |
| 2007/0183557 | A1* | 8/2007 | Manzke et al. ................... 378/4 |
| 2008/0173824 | A1* | 7/2008 | Sekiguchi et al. ....... 250/370.11 |
| 2008/0292050 | A1 | 11/2008 | Goodenough et al. |

FOREIGN PATENT DOCUMENTS

| | | |
|---|---|---|
| JP | 02-051045 | 2/1990 |
| JP | 03-002746 | 9/1991 |
| JP | 2001276052 | 9/2001 |
| JP | 2006-275853 | 12/2006 |
| SU | 741011 | 6/1980 |

OTHER PUBLICATIONS

Douglas, Transmission Computed Tomography, Future Technologies, Chapter 130, 1981, pp. 4366-4368.

International Search Report Application No. PCT/US08/01978, International Filing Date Feb. 13, 2008, Search Report Dated Dec. 5, 2008, 4 pages.

Radiation Protection in Radiotherapy, Part 5, External Beam Radiotherapy Lecture 2 (cont): Equipment and safe design, 49 pages, downloaded Apr. 20, 2012.

US Office Action dated May 28, 2010 in related U.S. Appl. No. 12/070,043, filed Feb. 13, 2008, 11 pages.

* cited by examiner

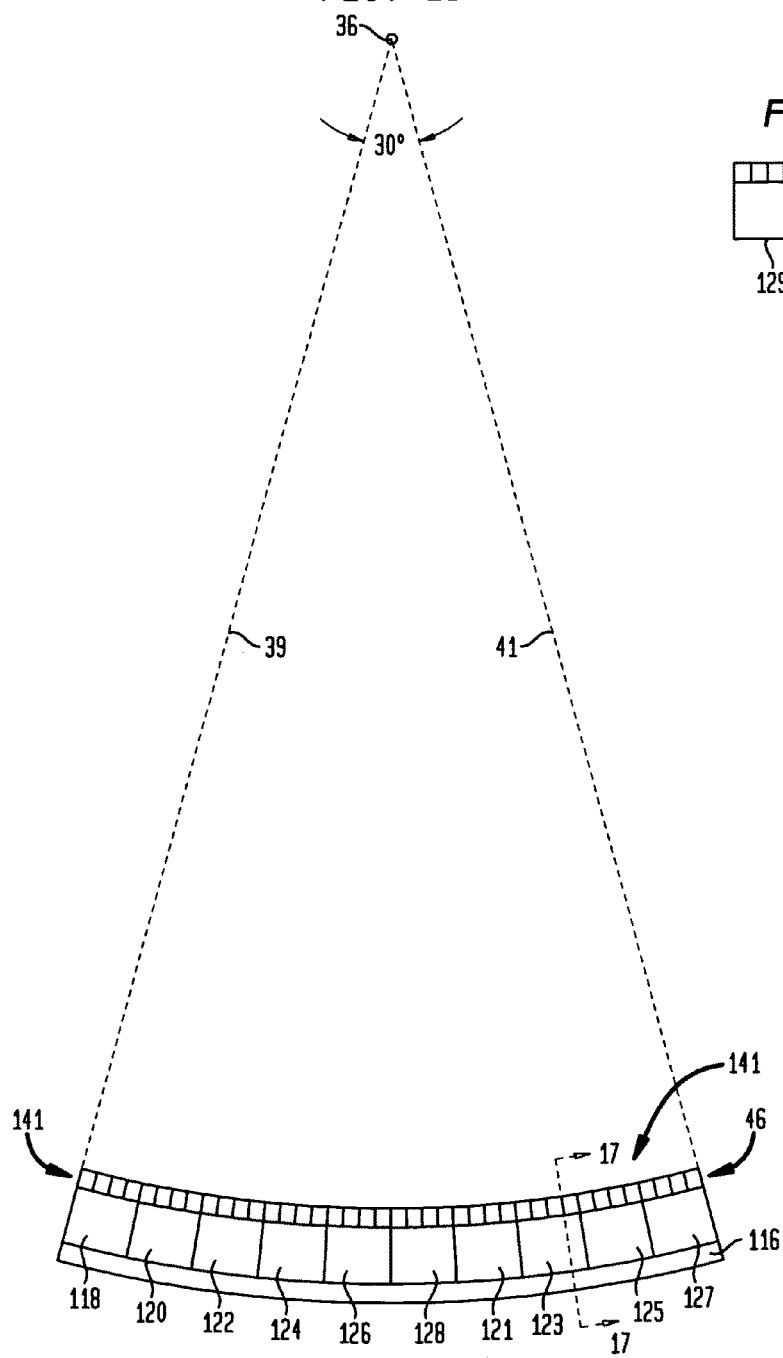
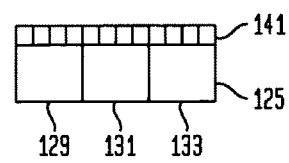

A) X-RAY ARRIVES
B) e-JUMPS TO CONDUCTION BAND
C) e-TRAPPED

FIG. 36
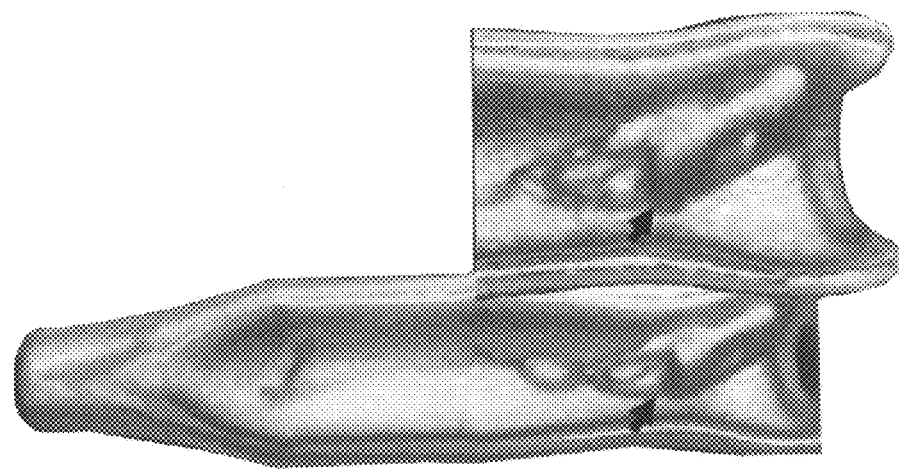
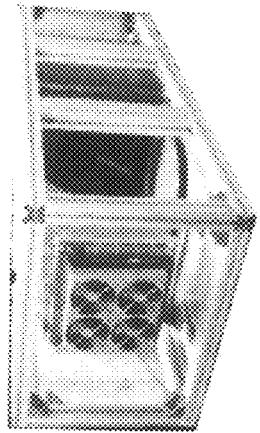
EXAMPLES
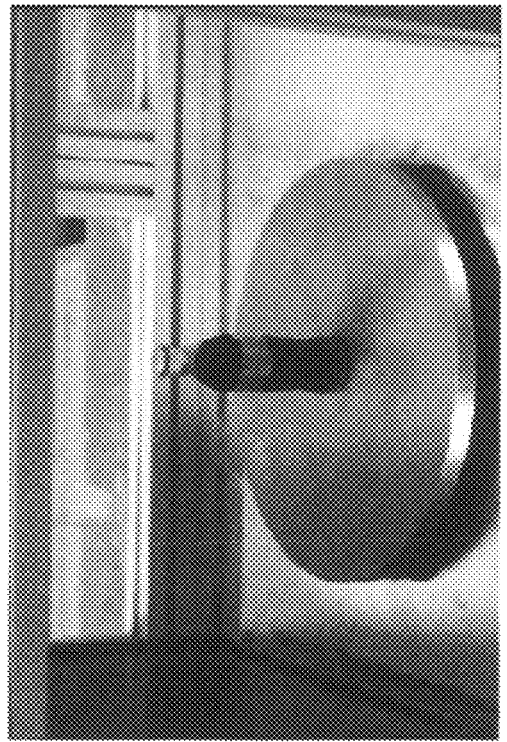
HIDDEN DETONATING FUSE IN A BOTTLE

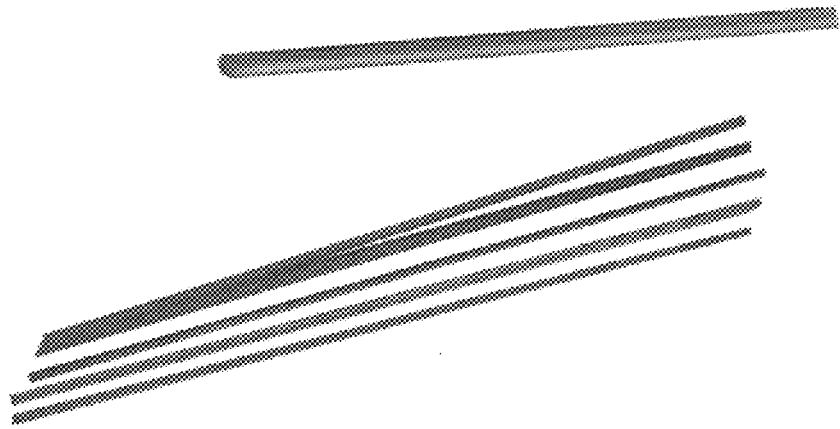
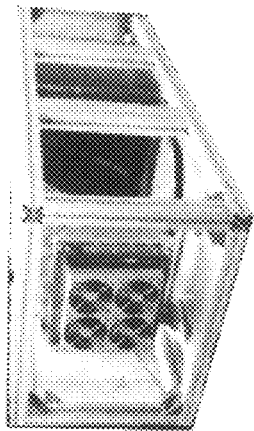
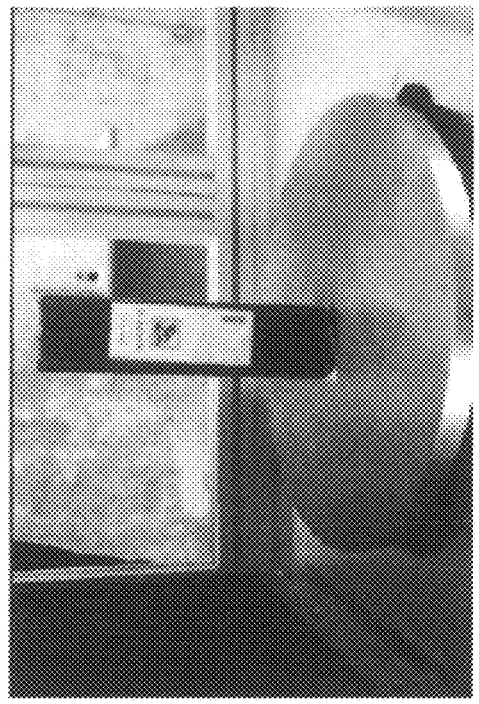
FIG. 37

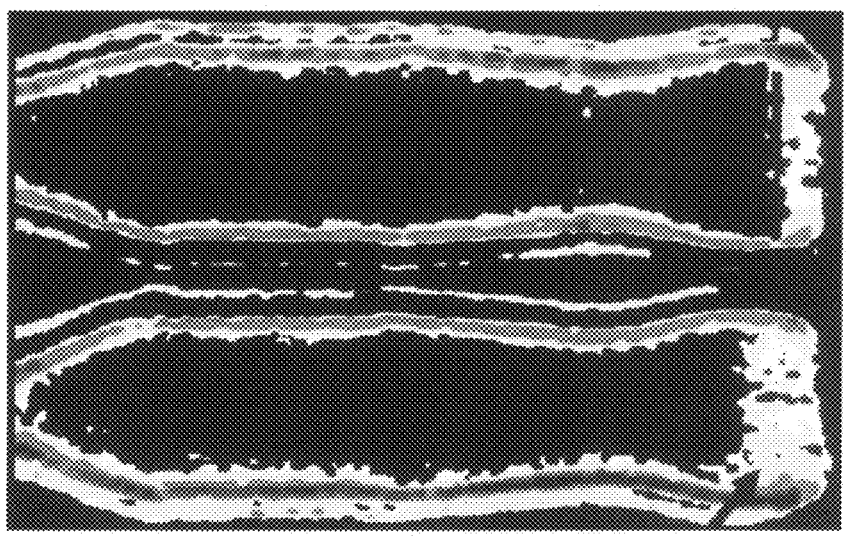
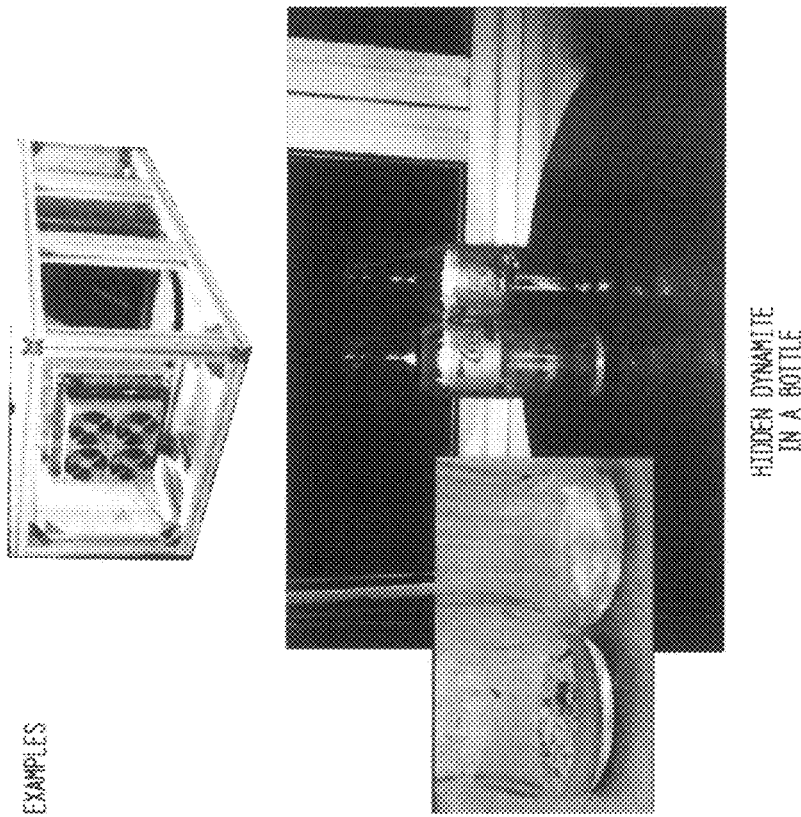
FIG. 38

TRANSPORTATION CONTAINER INSPECTION SYSTEM AND METHOD

CROSS REFERENCE TO OTHER APPLICATIONS

This application claims priority to U.S. Provisional Patent Application Nos. 61/184,449, filed on Jun. 5, 2009, and 61/251,592, filed on Oct. 14, 2009, which are hereby incorporated herein by reference.

TECHNICAL FIELD

The present invention relates to apparatus and methods for computed tomography ("CT") scanning. More specifically, the present invention relates to CT scanners and methods for scanning relatively large objects or bodies, and to radiation detectors and detection methods, particularly for detecting X-rays. In particular, the invention relates to CT Scanning and contraband detection in relatively large transportation containers such as standard sealed containers for transporting goods by ocean freight or air freight; land freight carrier containers such as truck bodies, rail road cars and the like; smaller cargo containers shipped on pallets or otherwise, in trunks and other baggage for ocean and airplane travelers, etc.

BACKGROUND OF THE INVENTION

CT overcomes many problems faced by using conventional two-dimensional radiographs. CT does this by scanning thin slices of the object with a narrow X-ray beam that rotates around the object. This produces an image of each slice as a cross-section of the body, for example, and can thus show each of the tissues or objects in a slice of width ranging from 0.5 mm-10 mm, with 5 mm being typical.

In contrast to radiography, CT can also differentiate between tissues or objects of similar density because of the narrow x-ray beam and the use of "windowing." In CT, information acquired can be stored on a digital computer as digital raw data and an image can, for example, be displayed on a video monitor or printed onto x-ray film. Such an image is made up of a matrix of thousands of tiny squares or pixels. A conventional single slice CT image has 262,144 pixels arranged in an array of 512×512 pixels, and 1,048,576 pixels (known as a "Megapixel") arranged in an array of 1024×1024 pixels is fast becoming common.

The detection of contraband in transportation containers, and particularly in to larger containers such as ocean freight cargo containers, air freight cargo containers, etc., presents a long-standing problem. Only a small percentage of such cargo containers are inspected for contraband, such as illegal drugs, explosive devices, illegal weapons, radioactive materials, etc. As a result, such containers present an inviting vehicle for the smuggling of contraband.

When such containers are inspected for contraband, it usually is very labor-intensive and time-consuming to do so. Therefore, it also is relatively expensive to do so. These factors are significant in limiting the amount of inspection which can be done at a tolerable cost.

Accordingly, one of the objects of the invention is to provide a system or device and method for inspecting transportation containers for contraband at a relatively modest cost.

CT scanners are used to perform the non-invasive inspection of objects such as luggage, bags, briefcases, cargo containers, vehicles and the like, to identify hidden contraband at airports, public buildings, roadways and other security checkpoints. The contraband may include hidden guns, knives, explosive devices and illegal drugs, for example.

Computed tomography ("CT") enables the reconstruction of the cross-sectional images of the cargo contents being scanned, enabling identification of the items in the container. CT images have long attracted much attention in the field of medical diagnosis because they provide a sharp tomographic image of a soft tissue which could not be obtained using conventional X-ray films. CT images also provide higher resolution, better image contrast and greater sensitivity to characteristics of the object being scanned, than radiographs.

While the smuggling of contraband such as guns and explosives onto planes in carry-on bags and in luggage has been a well known, ongoing concern, another serious threat is the smuggling of contraband across land borders by concealment in trucks or automobiles and by boat in large cargo containers. Standard cargo containers are typically 20 to 50 feet (6 to 14 meters) long, 8 feet (2½ meters) high and 6 to 9 feet (3 to 4 meters) wide. Air cargo containers, which typically contain many pieces of luggage or other cargo to be stored in the is body of an airplane, may range in size from about 35 by 21 by 21 inches (around less than 1 meter by 0.7 meter by 0.7 meter) up to about 240 by 118 by 96 inches (6 by 3 by 2½ meters).

Large collections of objects, such as, for example, many pieces of luggage, may also be supported on pallets. Pallets, which may have supporting side walls, may be of a size comparable to cargo containers.

Typical airport scanning systems for carry-on bags have tunnel entrances up to about 0.40×0.40 meters. Scanning systems for checked luggage have only slightly larger openings. Thus, such systems are insufficient to inspect cargo containers because only bags that are small enough to fit through the scanner's tunnel may be inspected. The relatively low energies used in typical X-ray luggage and baggage scanners usually are insufficient to enable the X-rays to pass through the much larger cargo containers. In addition, many such conventional systems operate too slowly to economically inspect larger objects, such as cargo containers. Thus, the art faces a problem in developing a system for scanning large objects efficiently and accurately.

SUMMARY OF THE INVENTION

In exemplary embodiments of the present invention, a transportation container inspection system can include a scanner support structure defining a scanning volume, a scanner rotor mounted on the support structure, the scanner rotor mounted so as to rotate about an axis of rotation running through the scanning volume, where the rotor includes an X-ray source mounting arm extending outwardly from the rotational axis in a first direction, and a detector located on the rotor away from the rotational axis in a second direction, opposite to the first direction. The system can further include a detector positioned to receive X-radiation transmitted through the scanning volume from the source, and a data processor to analyze the received X-ray signal to identify at least some of the contents of the container.

In exemplary embodiments of the present invention an X-ray detector can be provided, such detector including (a) a plate for detecting X-rays transmitted through an object being examined and converting said X-rays into electromagnetic radiation of a wave length differing from the wave length of said X-rays; (b) a digital camera for viewing said plate and detecting the pattern of said electromagnetic radiation on said plate and converting the detected radiation patterns into electrical signals, and (c) a data processor for processing said electrical signals so as to determine the composition of said object.

In exemplary embodiments of the present invention an X-ray detector can be provided, the detector including a plurality of modules assembled side-by-side to form a detector assembly, each of said modules comprising (a) a housing; (b) a detector plate forming an entrance wall to the housing, the plate adapted to detect X-rays transmitted through an object being examined and converting said X-rays into electromagnetic radiation of a wavelength differing from the wavelength of the X-rays; (c) a digital camera mounted to the housing to receive the electromagnetic radiation from the detector plate and convert the electromagnetic radiation into electrical signals; and (d) a data processor for processing said electrical signals so as to determine the composition of the object being examined.

In exemplary embodiments of the present invention a transportation container inspection system can be provided, said system including (a) a scanner support structure defining a transportation container location; (b) a scanner rotor mounted on said scanner support structure, said scanner rotor being mounted to rotate about an axis of rotation through said container location; (c) said rotor including an X-ray source mounting arm extending outwardly from said axis in a first direction; (d) a detector located on said rotor away from said axis in a second direction opposite to said first direction, said detector being positioned to receive X-radiation transmitted through said container from said X-ray source; and (e) a drive system for rotating said rotor about said axis and moving said container along said axis in synchronism with said rotor.

In exemplary embodiments of the present invention an X-ray detector plate can be provided, said detector plate comprising a coating on a substrate, the coating comprising a mixture of: (a) a phosphor compound that converts X-rays into electromagnetic radiation of a wave length differing from the wavelength of said X-rays; (b) a protective compound that provides protection to said phosphor; (c) a reflector compound that amplifies said light signals; and (d) optionally a dopant compound.

In exemplary embodiments of the present invention a method for the preparation of a detector plate can be provided, the method including (a) mixing or dispersing in a liquid solution of (i) a phosphor compound that converts X-rays into electromagnetic radiation of a wave length differing from the wavelength of said X-rays; (ii) a protective compound that provides protection to said phosphor; (iii) a reflector compound that amplifies said light signals; and (iv) optionally a dopant compound; (b) depositing said mixture on a substrate; and (c) allowing said mixture to solidify, thereby forming a coating on the substrate.

In exemplary embodiments of the present invention an X-ray detector can be provided, said X-ray detector comprising a plate that converts received X-rays into electromagnetic radiation of a wavelength differing from the wave length of said X-rays. Said received X-rays can be X-rays that were transmitted through at least one object being examined. Further, for example, the X-ray detector can comprise a mirror, arranged to direct said electromagnetic radiation to a capturing device. Additionally, in exemplary embodiments of the present invention said capturing device can comprise a digital camera which converts the electromagnetic radiation to electrical signals. Further, in such exemplary embodiments the X-ray detector can comprise a data processor to process said electronic signals into an image of the at least one object. Finally, in addition, such a data processor can enhance the image so as to allow a viewer to easily distinguish the components of said at least one object and to determine the composition of at least one of said components.

In exemplary embodiments of the present invention a CT scanner can be provided, comprising any of the exemplary X-ray detectors described above. Such a CT scanner can make multiple scans of at least one object by moving the at least one object relative to an X-ray source. Further, for example, the CT scanner can comprise a data processor, which processes data from the multiple scans of the at least one object to generate 2D and/or 3D images of said at least one object. In exemplary embodiments of the present invention visualization software can be run on the data processor to enhance the 2D and/or 3D images so as to allow a viewer to easily distinguish the components of said at least one object and to determine the composition of at least one of said components. In exemplary embodiments of the present invention several 2D and 3D algorithms for different geometrics of the scanner can be used to generate said 2D and/or 3D images.

In exemplary embodiments of the present invention an inspection system can be provided, comprising a scanner support structure with an opening; and a rotor mounted on the scanner support structure, the rotor mounted so as to rotate about an axis of rotation running through the opening, the rotor including: an X-ray source, and a detector, the detector being positioned to receive X-rays emitted from said X-ray source. In exemplary embodiments of the present invention the opening can be between 3-5 meters in diameter, or, for example, can be greater than or equal to 5 meters in diameter. Alternatively, in a small scale embodiment, the inspection system can have an opening between 0.5 and 2 meters in diameter. In exemplary embodiments of the present invention the inspection system can further include a data processor for processing the X-rays is received by the detector to generate 2D and/or 3D images of at least some of the contents of a container placed in the opening. In exemplary embodiments of the present invention said 2D and/or 3D images can be color enhanced by the data processor, and, for example, said color enhancing can assign different colors to objects, as a function of their density.

In exemplary embodiments of the present invention such an inspection system can further include a drive device for moving a container through said opening, a braking system for stopping the rotation of said rotor at each of two stop positions and reversing the direction of rotation of said rotor at each of said stop positions, and moving said container from a first reading position to a second reading position during the deceleration, stopping, and acceleration of said rotor at each of said stop positions. The inspection system can have an opening of a size and shape so as to allow a transportation container to pass through it.

BRIEF DESCRIPTION OF THE DRAWINGS

FIG. 16 is a schematic side-elevation view of a further embodiment of the detector structure of the invention;

FIG. 17 is a cross-sectional view taken along line 17-17 of FIG. 16;

FIGS. 35-39 depict several real examples of objects scanned and identified using an exemplary small scale scanning system according to an exemplary embodiment of the present invention;

DETAILED DESCRIPTION OF THE INVENTION

Figure 1:
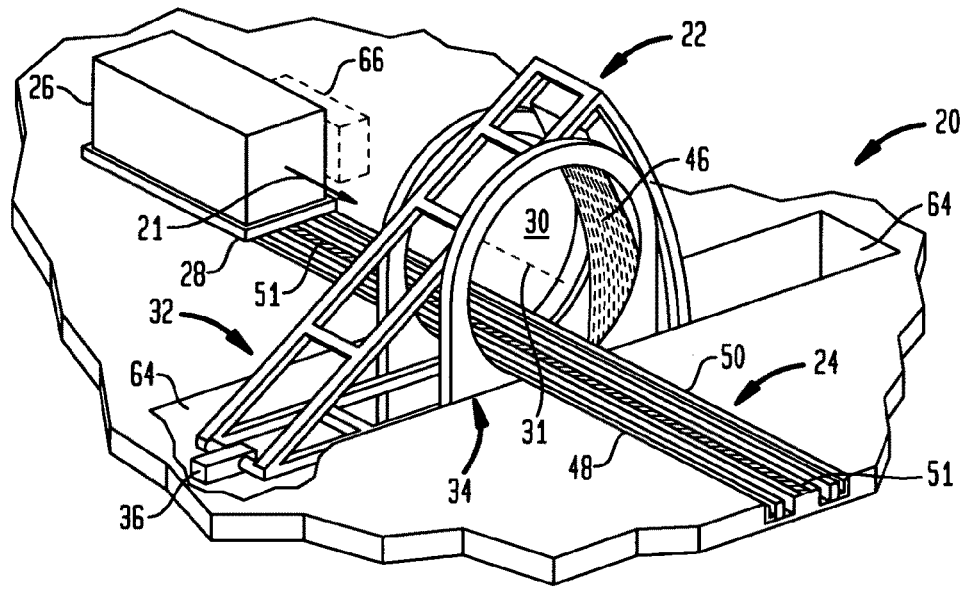
FIG. 1 is a perspective, partially schematic view of an exemplary scanning system according to an exemplary embodiment of the present invention.

There have been various proposals for systems and methods to accomplish large container CT scanning. Some involved the use of X-ray scanning and computer tomography to take many different images of the contents of a container and analyze the images to determine the composition of the materials at various locations within the container.

For example, it was proposed that a plurality of X-ray sources could be moved on a semicircular track around a container. The sources emit X-rays, some of which would pass through the container and could be detected, thus allowing the to contents of the container to be imaged. However, because X-ray sources tend to be relatively heavy and difficult to move rapidly, such a system would be both very slow and expensive. Furthermore, because relatively high energy X-rays are required to scan the contents of large containers, having multiple high energy X-ray sources can be unreasonably expensive.

It has also been proposed in CT scanning of humans to use a relatively large, arcuate sheet of phosphor material which can record and store X-rays. Then, when subsequently stimulated by a second type of radiation, such as, for example, laser beams, the phosphor material releases visible light in proportion to the strength of the original X-rays it had received. Such proposals have not met with wide acceptance for a variety of reasons.

Although, in some prior proposals, phosphor sheet materials have been used in detectors, because such materials store the images and then require a separate read-out step to obtain the image signal, this has the disadvantage of requiring additional equipment, as well as requiring additional time to convert the stored signals into visible light images and then process those.

Accordingly, in exemplary embodiments of the present invention, a relatively broad area detector sheet can be provided, which can rapidly produce light patterns corresponding to the received X-rays without additional or extra read-out equipment. In exemplary embodiments of the present invention a such detector can be provided which is relatively economical in construction and operation.

In exemplary embodiments of the present invention a CT Scanning device can be provided which can convert received X-ray signals into visible images quickly and accurately so as to make real-time imaging a reality.

Thus, in exemplary embodiments of the present invention, a system (including a device) and method can be provided for inspecting the contents of transportation containers at a relatively modest cost. Such system and method can provide a relatively accurate and high quality inspection in a relatively short time. Moreover, such system can be relatively inexpensive to manufacture, operate and maintain. Such a system, can include a relatively broad area detector sheet which can rapidly produce light patterns corresponding to the X-rays it receives is without additional or extra read-out equipment.

Thus, in exemplary embodiments of the present invention a scanner can have, for example, a rotor with an X-ray source at one end, and, for example, a large area detector at the other end. The rotor can have, for example, a central opening through which containers, such as, for example, cargo containers, can be moved. The rotor can, for example, be supported by a rotor support structure which has a matching opening. In exemplary embodiments of the present invention the cargo containers can be moved through the openings in the rotor and the support structure in synch with the rotation of the rotor so as to scan the entire container relatively quickly.

In exemplary embodiments of the present invention the detector structure can comprise one or more X-ray converting plates (also called detector plates) which can use a selected material to directly convert received X-rays into visible light. The light patterns can be scanned by one or more CCD or ICCD cameras whose output can be delivered to a computer or data processor to form corresponding images which facilitate identification of objects found in the container. In exemplary embodiments of the present invention real-time images can be obtained, as well as 3-D images, as described below.

In exemplary embodiments of the present invention the rotor can first swing in one direction and then swing in the opposite direction, where, for example, it scans over an angle of at least two hundred and ten degrees in each scan.

In exemplary embodiments of the present invention the containers can be positioned on a rail car traveling on rails, or the like, when passing through the openings of the rotor and the rotor support.

FIG. 1 is a perspective view of a scanning system 20 for scanning and detecting the contents of cargo container 26. As noted, cargo container 26 can be, for example, of the type used for carrying cargo on ships, in aircraft, on trailer trucks and railroad cars, etc.

In exemplary embodiments of the present invention, cargo container 26 can move, for example, on a flat-top railroad car 28 along a set of railroad tracks 24 (in the direction of arrow 21) through scanning structure 22. Scanning structure 22 can include a rotor 32, which can be rotatably mounted on rotor support structure 34. Each of support structure 34 and rotor 32 can have, for example, a centrally-located opening. These openings can be co-aligned so as to form a passageway or short tunnel 30 through which transportation container 26 can, for example, pass for inspection.

In exemplary embodiments of the present invention rotor 32 can have a girder structure 40, 41, 42, 44 which can have, for example, a generally triangular shape, with a curved bottom edge 42. At the left end of rotor 32 can be mounted X-ray source 36, for example, mounted on cross-member 38. In exemplary embodiments of the present invention, at the opposite end of rotor 32 can be, for example, mounted arcuate detector structure 46.

Figure 2:
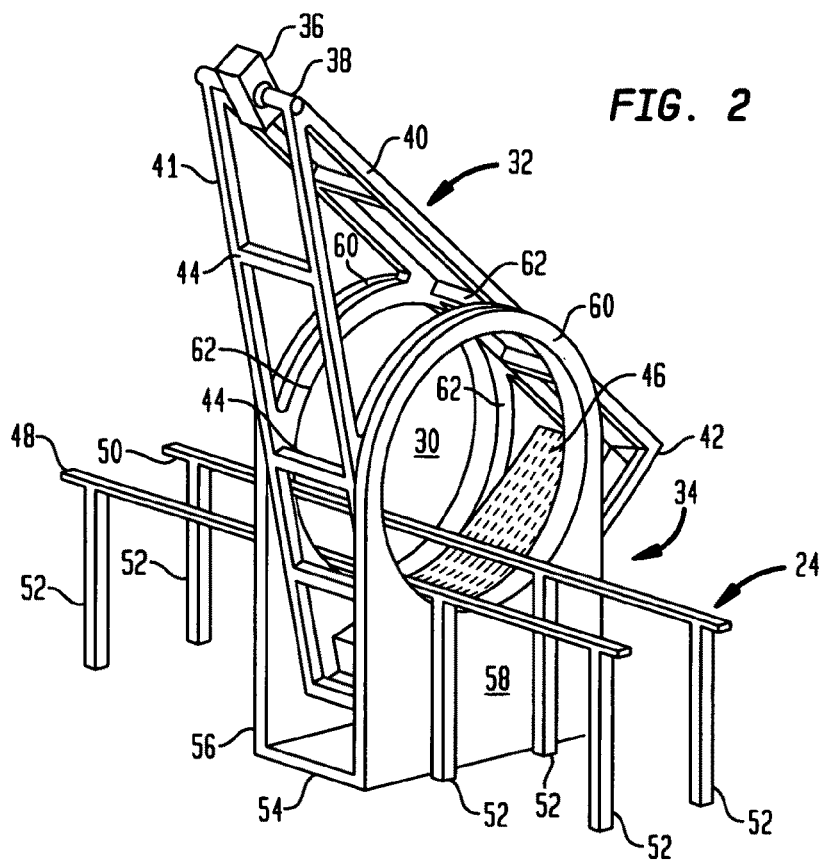
FIG. 2 is an enlarged schematic perspective view of a portion of the system of FIG. 1.

As shown in FIGS. 1-2, the rotor support structure can be stationary and rotor 32 can, for example, be mounted so as to rotate on structure 34 about central axis 31 (FIG. 1). In the depicted example, the direction of movement 21 of cargo container 26 is parallel to rotational axis 31.

X-ray source 36 forms a generally pyramid-shaped beam (see index numbers 152, 154 and 156 in FIG. 8) which can cover the entire curved surface of detector structure 46. X-rays which pass through cargo container 26 as passes through opening 30 can be recorded on detector 46 which can, for example, immediately convert the received X-rays into light signals.

In the exemplary embodiment shown in FIG. 1, rotor 32 extends partially into is trench 64 which is relatively shallow, yet deep enough to allow the outer end of rotor 32 and source 36 to travel from a position substantially fifteen degrees below the horizontal at one extreme position, to fifteen degrees below the horizontal at the other extreme, thus allowing a total scan arc of 210 degrees. In scanning, rotor 32 can, for example, alternatingly rotates clockwise and counter-clockwise between such two extreme positions, while cargo container 26 is moved through opening 30.

Figure 3:
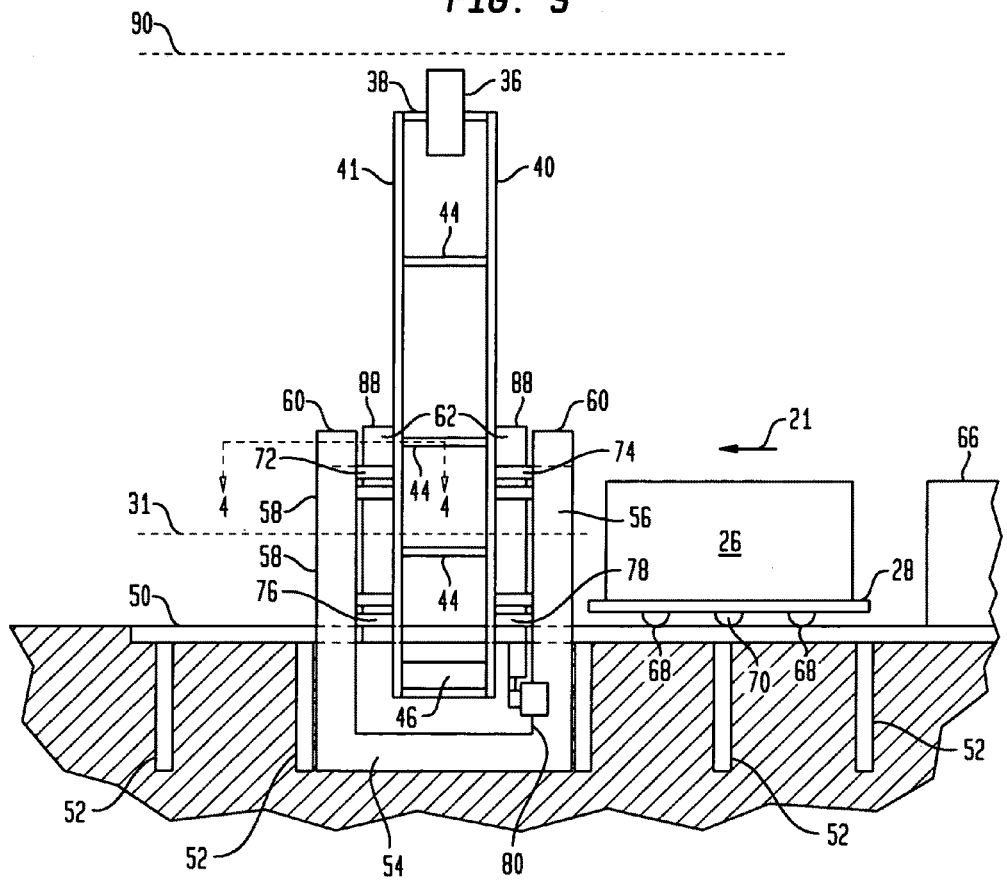
FIG. 3 is a schematic, partially broken away side elevation view of a portion of the system shown in FIGS. 1 and 2.

In exemplary embodiments of the present invention, railroad car 28 can be moved along railroad tracks 48 and 50 by means of, for example, gear motor 70 (see FIG. 3) which can be engaged with centrally-located cog rail 51, located between rails 48 and 50. As shown in FIG. 3, rail car 28 can have conventional flanged wheels 68, allowing it to roll smoothly and evenly along rails 48 and 50. As noted, in exemplary embodiments of the present invention the movement of cargo container 26 can be synchronized with the rotation of rotor 32.

Continuing with reference to FIG. 1, in exemplary embodiments of the present invention a preliminary inspection station 66 can also be provided, at which preliminary inspection of a cargo container can be conducted, as is described more fully in U.S. patent application Ser. No. 12/070,043.

Specifically, at inspection station 66, heat sensor equipment can be used, for example, to sense the presence of a heat source in a container so as to detect human beings or animals which might be damaged by exposure to the X-rays to be used in the equipment 22, and also to permanently remove any humans and/or animals if their transfer is illicit.

In exemplary embodiments of the present invention a radiation sensor can be used at station 66 to detect any source of radioactivity which might be located in the container so that it can be removed safely. Additionally, a linear X-ray scan can be performed at station 66 to determine whether, and if so where, there is a substantial amount of empty space in the container. This information can then be fed to the scanner system to enable it to avoid scanning the empty space.

In exemplary embodiments of the present invention rotor 32 can be balanced with respect to rotational axis 31. That is, the force moments in the counter-clockwise direction are set to be equal and opposite to the force moments in the clockwise direction.

Although X-ray source 36 is much farther from the axis 31 than detector 46 at the opposite end of the detector structure is relatively heavy. This weight is due, in part, to the presence of metal components and relatively thick lead shielding which tends to stop stray radiation from escaping from the outer surface of the detector so as to shield personnel and equipment in the area from stray X-rays.

Rotor And Support Structure

Figure 4:
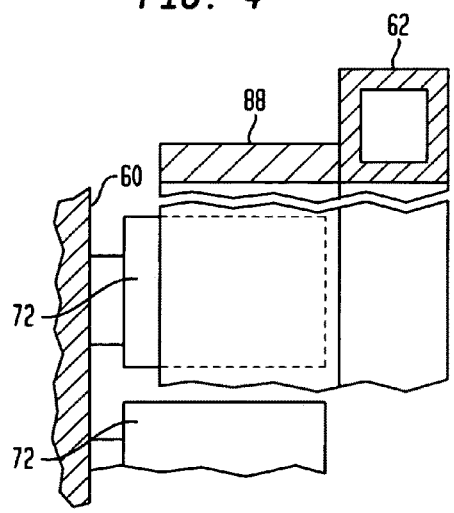
FIG. 4 is a partially broken away enlarged cross-sectional view taken along line 4-4 of FIG. 3.

Referring to FIG. 2, rotor support structure 34 can include a bottom wall 54 which can be anchored at the bottom of trench 64, and a pair of vertical, spaced-apart side walls 56 and 58. The side walls can have circular holes formed by curved portions 60, etc. Such circular openings in the rotor can be formed by curved beams or square tubing 62 (see FIG. 4).

Railroad tracks 48 and 50 (and 51, although not shown in FIG. 2) can pass through the openings in rotor and rotor support at its lower edge and can be supported on the ground by pilings 52 extending into the ground.

Rotor Bearings and Drive System

Figure 5:
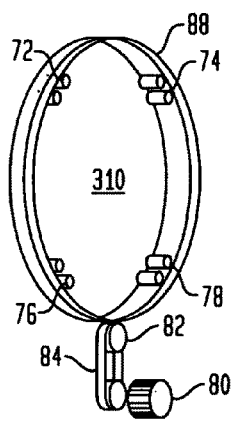
FIG. 5 is a schematic perspective view of a portion of the system shown in FIG. 3.

A bearing and drive system for an exemplary rotor is not shown in FIGS. 1-2, but is illustrated in FIGS. 3 and 5. With reference thereto, for example, extending outwardly from rings 62 can be cylindrical flanges 88. These flanges can engage with four pairs of rollers 72, 74, 76 and 78 (FIG. 5) which extend inwardly from each of vertical side walls 56 and 58 so as to support the weight of the rotor and make it relatively easy to rotate.

As shown in FIGS. 3 and 5, a reversible electrical drive motor 80 can be used to drive chain 84 which can, for example, rotate friction wheel 82 which can engage flange 88 to rotate rotor 30.

Rotor Movement

In exemplary embodiments of the present invention a scanner can scan over a minimum angle of two hundred ten degrees in order to provide enough data to accurately determine the contents of an exemplary container. Actually, trench 64 can, for example, be sufficiently deep so as to permit the rotor to move at each extreme position to twenty degrees past horizontal for a total angle of travel, from one stop point to the other, of two hundred twenty degrees.

At this juncture it is noted that according to the basic theory of tomography, in order to perform a full scan it is not necessary to scan around a full 360° path, but rather 180° degrees plus the angle of the accelerator beam is sufficient. Thus, in exemplary embodiments of the present invention a scanner can scan over a minimum angle of two hundred ten degrees.

Additionally, however, scanning should be done at a constant speed. Thus, where a rotor scans first by rotating in a clockwise direction, and then subsequently in a counterclockwise direction, when the system finishes scanning on one side, it has to slow down and stop, which means losing the constant speed and thus the ability to make a proper scan. In exemplary embodiments of the present invention this process of braking, stopping, starting and once again acquiring a constant speed in the opposite direction can, for example, be done in an angle of 5° (on each side). This 5 degrees or arc length is not used for scanning, but is necessary for the proper operation of the mechanical system. Thus, to optimize the use of these non-scanning time intervals, in exemplary embodiments of the present invention, when the rotor is moving through these 5 degree swaths at the end of each scan direction the container can, for example, be moved to its next reading position.

Figure 11:
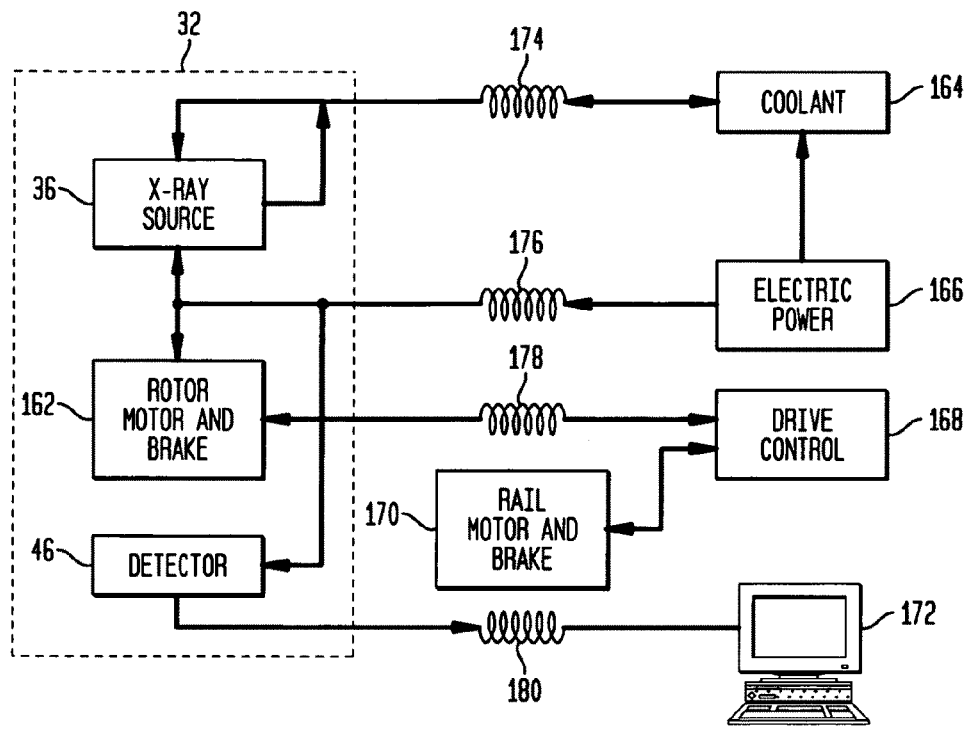
FIG. 11 is a schematic block diagram of exemplary electrical and mechanical operating systems according to exemplary embodiments of the present invention.

Referring now to FIG. 11, in exemplary embodiments of the present invention an electrically operated brake 162 can be provided with the rotor motor as indicated to control the reciprocating motion of the rotor. When the rotor reaches a position within five degrees of its end point, drive motor 80 can be turned off and the electrically operated brake can be applied so as to bring the rotor to a stop at its end position. Then, the drive motor can reverse direction and drive the rotor in the opposite direction, gaining full speed, for example, within five degrees after it starts rotating in the reverse direction. This procedure can be repeated until full scanning of a container has been achieved.

In accordance with the invention, because the rotor is rotationally balanced about the axis of rotation, drive motor 80 used to rotate the rotor need not be very large or expensive. This also applies to the braking mechanism needed to stop the rotor.

Additionally, in exemplary embodiments of the present invention, rotor 32 can be rotated at a relatively high speed to achieve scanning in a relatively short time. For example, it is believed that rotor 32 can execute one complete scan (rotation through an angle of two hundred and twenty degrees in one direction) in thirty seconds or so. Such a scan can, for example, be sufficient to cover a length of approximately 1.5 meters of the cargo container. At this rate, a cargo container can be scanned fully within from a little over two minutes to around four minutes, depending upon the length of the container.

In some exemplary embodiments, the speed of the rotor can be increased to complete one scan in as little as fifteen seconds or less. In such case, scanning time can be proportionately reduced. Scanning time can also be reduced, for example, by using two linear accelerators as the X-ray source, thus effectively doubling the width of the scan beam (using the same distance of the X-ray source from the container). Further, in other exemplary embodiments of the invention, as described below, even higher scanning speeds can be achieved.

Alternative Scanner Embodiments

Figure 6:
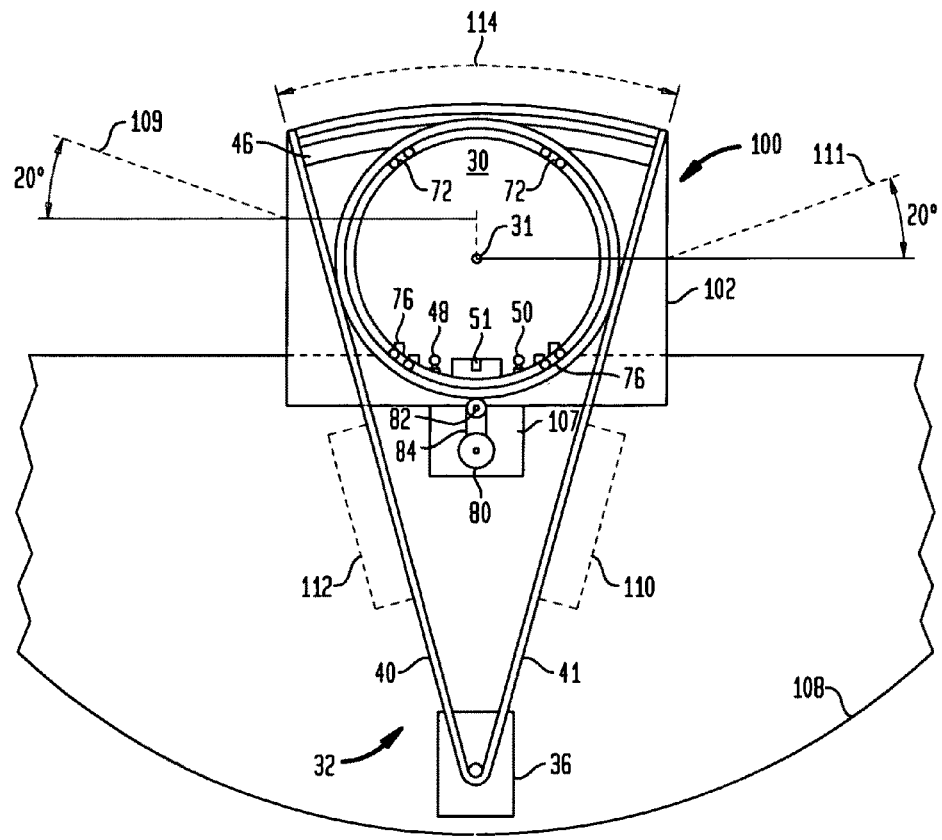
FIG. 6 is a front elevation view, partially broken-away and partially schematic, of exemplary scanning system according to an exemplary embodiment of the present invention.
Figure 7:
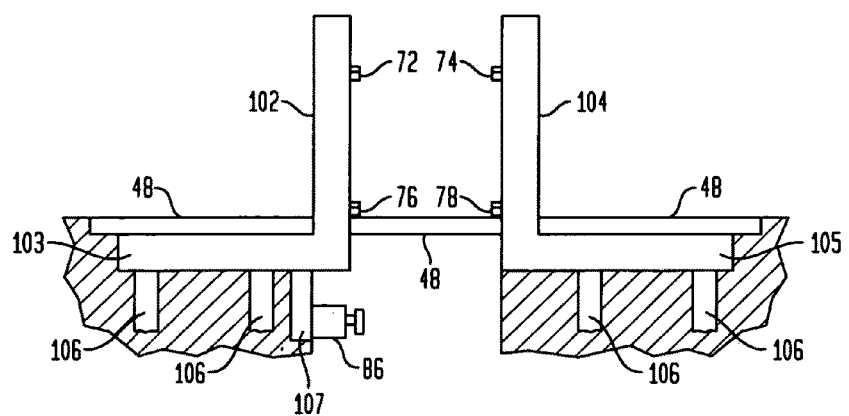
FIG. 7 is a side elevation view of a portion of the structure shown in FIG. 6.

FIGS. 6-7 show an alternative scanner system 100 which is essentially the same as the exemplary scanner system shown in FIGS. 1-6, except that rotor 32 is mounted to rotate through a complete circle, first in one direction and then in the opposite direction for each scanning operation. To this end, a semi-circular trench 108 can be dug in the ground, and vertical rotor support walls 102 and 104 (FIG. 7) can be anchored in the ground by horizontal portions 103 and 105 with anchor posts 106 buried in the ground on both sides of the trench. In exemplary embodiments of the present invention drive motor 80 can be mounted on a vertical extension 107 of support member 102.

In addition, optional locations of various equipment, to be described below, are indicated by dashed lines 110, 112 on the sides of the rotor structure, and at 114 at the detector end of the rotor, as shown in FIG. 6.

In a further alternative embodiment, the longer portion of the rotor, that extending into trench 105 in FIG. 6, can move only through an angle of 220° with stop positions along lines 109, 111 which are, respectively, 20° clockwise beyond horizontal and 20° counter clockwise beyond horizontal. However, in this exemplary embodiment, the long portion of the rotor moves underground along most of its travel path, an arrangement which may be necessary or desirable to prevent the rotor from extending upwardly to as great a height as the exemplary embodiment of FIGS. 1-3. Such a construction can allow the roof 90 of a shelter for the scanner (as shown in FIG. 3) to be considerably lower than otherwise.

Figure 13:
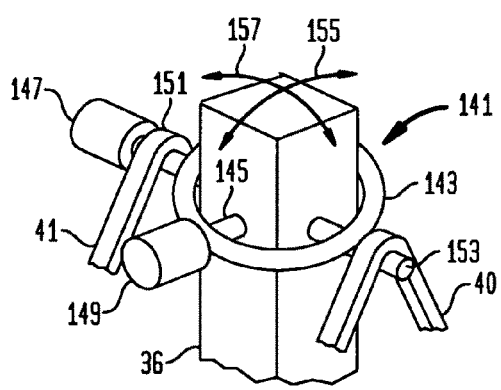
FIG. 13 is a perspective, partially broken-away and schematic view of another embodiment of the invention

FIG. 13 shows a mounting structure 141 for the X-ray source 36 in another exemplary embodiment of a scanner according to the present invention. With reference thereto, mounting structure 141 is a gimbal mechanism with a gimbal ring 143 rotatably mounted on girders 40, 41 by means of a shaft 151, 153 drivably coupled to a first servomotor 147 to rotate ring 143 about the shaft. X-ray source 36 is here rotatably mounted in the ring on a shaft 145 which is drivably coupled to a second servomotor 149.

Operation of servomotor 147 rotates ring 143 through an arc 155 in a plane parallel to the rotation of the scanner rotor to move the X-ray beam, and widen the effective arc of the X-ray beam, to enable faster scanning, using appropriate modifications to the detector and adjustment of the output power level of the X-ray source.

Servomotor 148 can be operated to rotate X-ray source 36 about axis 145 so as to swing the source along the plane of a second arc 157 which is orthogonal to the plane of arc 155. This can allow, for example, broadening the width of the X-ray beam to facilitate scanning a greater length of a cargo container, as well as to increase the scanning speed and/or reduce the movement of the cargo container.

If desired, source 36 can be mounted so that rotation is permitted in only one of the planes of the arcs 155, 157 to enlarge the scanning area in only one dimension.

Figure 14:
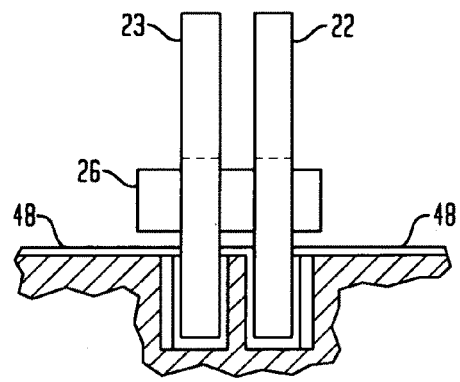
FIG. 14 is a side elevation view, partially cross-sectional and partially schematic, of a further embodiment of the invention.

A further exemplary embodiment of the invention is shown in FIG. 14, in which two or more scanners 22 and 23 can be, for example, provided at different longitudinal positions along the cargo container 26 to double or further multiply the scanning speed of the installation.

In exemplary embodiments of the present invention, X-ray source 36 can be any of a variety of known, relatively high output-energy devices. One that has been found to have desirable properties is the Varian "Linac" (term of art for "linear accelerator") model MI6 source, which can produce either a 6 MEV or a 3 MEV output.

Some sources, such as, for example, the Linac MI6, are designed to be stationary when operated, as in a hospital, and therefore tend to be relatively heavy. Therefore, in exemplary embodiments of the present invention one of a variety of readily-available custom-designed sources can be used, each of which can have substantially less weight than those designed for stationary operation.

Other X-ray sources, currently in development, use laser acceleration of the electron beam to generate the X-rays instead of RF magnetron acceleration. Such sources can be used to advantage in exemplary embodiments of the present invention inasmuch they are much lighter in weight and shorter in length than typical sources now available.

In exemplary embodiments of the present invention X-ray source 36 can be used, for example, to scan "in colors"—that is, to scan a selected volume with both the high-energy (6 MeV) and lower-energy (3 MeV) X-rays to produce different images of the same objects and improved identification of those objects.

Scanning in colors can be useful because many compounds have different behavior at 3 MeV and 6 MeV, thus allowing a better result and the avoidance of borderline cases. In fact, the examples of compounds, having different behaviors in these two energies are almost infinite. Dual (high) energy X-ray material discrimination is based on the fact that different materials have different energy dependence in X-ray attenuation coefficients. Total attenuation coefficients of different materials at both lower energies (<3 MeV) and higher energies (>5 MeV), high-Z materials, such as lead and uranium, are more attenuating than low-Z materials, such as most organic goods. This is due to the photo-electric effect and to pair-production, respectively. The total attenuation coefficients change with photon energy. Therefore, the detector signal can be attenuated differently by the same object at different source energies. For example, 6 MeV X-rays are more penetrating than 3 MeV X-rays. For light material, such as plastic, the difference is the most significant. However, because it is necessary to wait some seconds to change the energy (say, for example, from 3 MeV to 6 MeV), in exemplary embodiments of the present invention scan can generally be made using one or other energy, and only in cases of doubt, a dual energy scan can be performed.

Exemplary Detector Structure Detail

Figure 8:
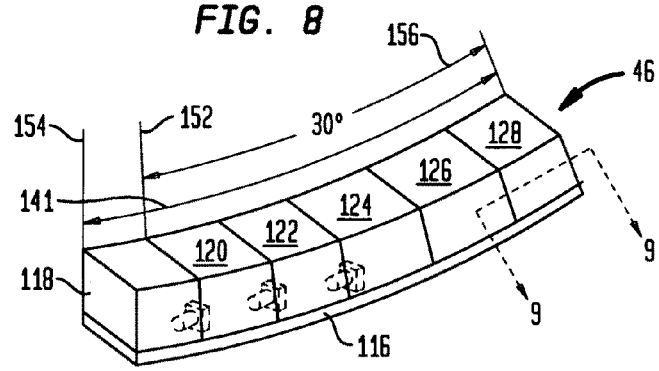
FIG. 8 is a perspective, partially broken-away and partially schematic view of an exemplary detector array used in the systems shown in FIGS. 1-7.
Figure 9:
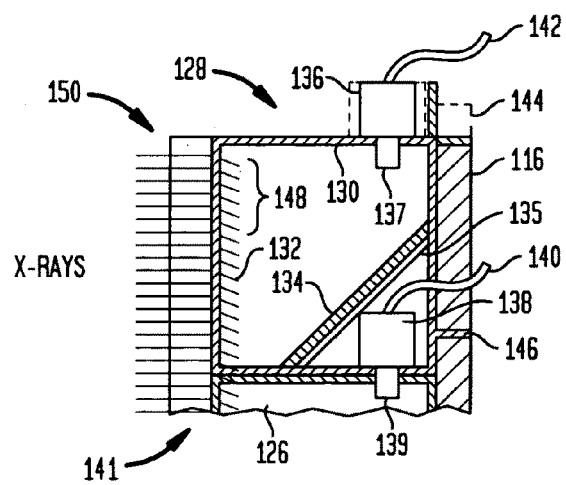
FIG. 9 is a cross-sectional, partially schematic view taken along section line 9-9 of FIG. 8.
Figure 10:
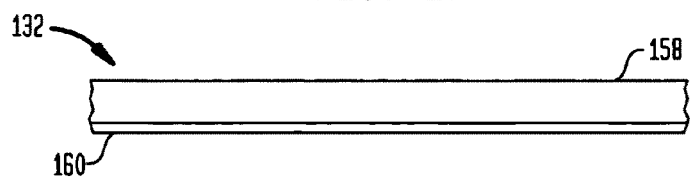
FIG. 10 is a cross-sectional view of a detector plate portion of the structures shown in FIGS. 8 and 9.

FIGS. 8-10 are schematic drawings showing, in principle, the structure of exemplary detector 46. Detector 46 can, for example, have an array of individual modules 118, 120, 122, 124, 126 and 128 which can be joined together end-to-end to form a composite large-area detector. In exemplary embodiments of the present invention the front surface of each module can be slightly curved and the array of modules can also be slightly curved to follow the arc of a circle having X-ray source 36 as its center. Although only six modules are shown in FIG. 8, a larger or smaller number can be used in various exemplary embodiments.

FIGS. 16 and 17 show an embodiment having three rows of detector modules 129, 131, 133 each having ten modules in the row. The edge lines 39, 41 show the angular extent of the detector, and the center of the source is the center of the arc formed by the detector array. Row 133 has each of modules 118, 120, 122, 124, 120, and 128 shown in FIG. 8, as well as identical modules 121, 123, 125 and 127.

The total angular extent of the exemplary array is approximately 30°. As described above, this angle can be made larger or smaller as needed, depending upon the power output of the X-ray source and other such parameters. Adjusting the angle and other parameters of the system allows the size of the scanner to be reduced, if needed or described by reducing the length of the rotor.

As can be seen by edge lines 152, 154, 156 in FIG. 8 defining the X-ray beam, the beam has a generally pyramidal shape, with a curved bottom surface. In exemplary embodiments of the present invention other beam shapes can be used as may be needed and/or desired.

FIG. 9 is a cross-sectional view taken along lines 9-9 of FIG. 8 illustrating the construction of module 128. Module 128 has a housing 130, and a front plate 132. The front plate 132 is curved slightly to form an arc, as shown in FIGS. 8 and 16, when the modules are assembled together.

Figure 12:
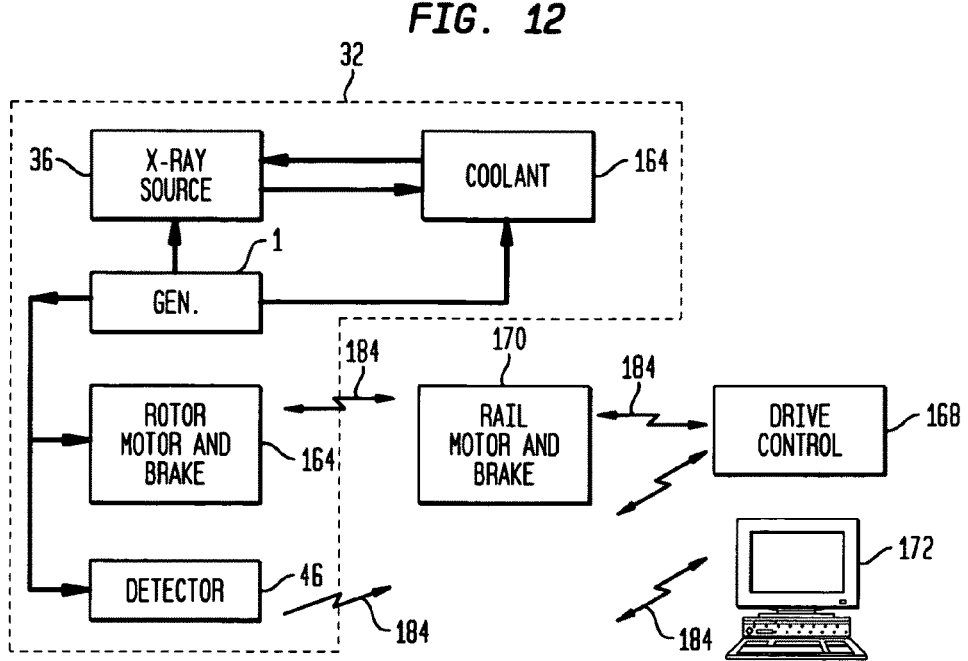
FIG. 12 is a schematic block diagram of another embodiment illustrating the electrical and mechanical operating system of the invention.

Mounted inside housing 130 can be a mirror 134 with a lead plate 135 on the rear surface to provide a means for mounting the mirror in the housing and to form an X-ray shield. Mirror 134 can be provided at a 45 degree angle, for example, or at other various desirable angles. A CCD or ICCD camera 136 can be mounted to the outside of housing 130 with its lens 137 extending into the housing to receive light images from the mirror 134. A cable 142 can carry data from camera 136 to a computer or data processor 172 (FIGS. 11, 12). In exemplary embodiments of the present invention cameras 136 can be enhanced, for example, by adding standard night vision features to them. Thus, for example, a CCD camera provided with The next module 126 in the array is partially shown at the lower portion of FIG. 9, and can have the same construction as module 128. It also has a CCD or ICCD camera 138 with its input lens 139 extending into the module. In exemplary embodiments of the present invention each of the individual modules can have the same construction. In exemplary embodiments of the present invention the housing of each module can be approximately cubical in shape.

Figure 15:
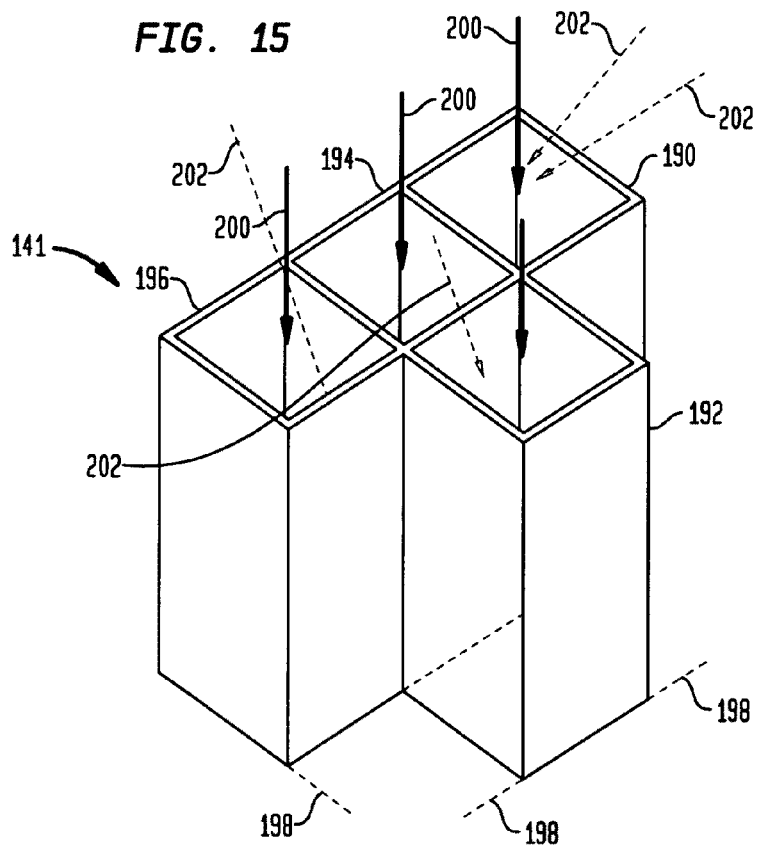
FIG. 15 is a perspective view of a portion of a part of the detector structure of the invention.

Continuing with reference to FIG. 9, plate 132 can receive X-rays 150 through a "honey comb" type of filter structure indicated schematically by dashed lines 141 in FIGS. 8, 16 and 17, and as shown in detail in FIG. 15. Plate 132 can have a phosphor coating 160 (FIG. 10) which can immediately convert the X-rays it receives into light signals 148, for example, visible light signals in the green region of the electromagnetic spectrum. The visible light signals can be reflected using mirror 134 to camera 136 which transmits corresponding image signals to computer 172.

In exemplary embodiments of the present invention, each of cameras 136, 138, etc. can be covered with lead shielding (shown in dashed outline) so that the shielding, together with shielding 135, can protect the camera from damage by the X-rays.

Additionally, rear lead shield 116 is shown in FIG. 9. It can, for example, stop most X-rays from exiting the detector at the rear and thus protects nearby personnel and equipment. Its thickness and weight can be varied to achieve balance of the rotor.

In exemplary embodiments of the present invention, mirror 134 can be used to reflect the light images to the camera rather than placing the camera directly in the path of the X-rays in order to minimize damage to the camera by the x-rays. Filter 141 can ensure that the X-rays actually received by the plate 132 are correctly directed and avoids or minimizes scattering. Its structure is shown in FIG. 15, which is a perspective view of a portion of the structure.

Filter 141, shown schematically in FIGS. 15-17, can, for example, consist of a plurality of metal tubes 190, 192, 194, 196, etc. secured together side-by-side to form an array covering the entire front surface of the detector 46.

Each of the tubes has a height and side wall dimensions such that it can transmit substantially only on-axis x-rays 200 to detector 46. Other rays, such as rays 202 entering the tubes at an angle to the axis from the source 36, strike the internal walls of the tubes and do not reach the detector.

Thus, using filter 141, the effects of scattering of the X-rays can be reduced or eliminated, and the X-rays transmitted accurately indicate the portion of the cargo being scanned.

Detector Plate

Luminescence is the name generally given to the emission of light by a material as a consequence of its absorption of energy. The excitation of the luminescent material is a prerequisite for the emission. Depending on the origin of the excitation, the luminescent process can be designated as: (i) Photoluminescence, where low energy photons are used to excite the material (such as visible or UV light); (ii) electroluminescence, where an electrical field is used to excite the material; (iii) chemiluminescence, where the energy is derived from a chemical reaction; (iv) bioluminescence, where the chemical reaction is produced in a living organism; (v) sonoluminescence, When the material is excited by ultrasound; (vi) incandescence, where the material is excited thermally; and (vii) magnetoluminescence, where the excitation is induced by magnetic fields.

Luminescence can also be classified depending on the duration of the emission after excitation. When the excitation is suspended, there is always an exponential decay of the emitted light. Luminescence is termed "fluorescent" when the time that it takes for the initial intensity of emission to decay from its original value to 1/e (where "e" is the charge of the electron) is on the order of $10^{-3}$ sec or less. When this time is in seconds, or even in hours, then the luminescence is termed "phosphorescent."

In exemplary embodiments of the present invention, a detector plate can comprise phosphorescent material (i.e., phosphor compound(s)). Preferably, the X-ray energy that passes through the scanned object reaches the detector plate with an energy that does not exceed 400 KeV. Also preferably, if such X-ray energy exceeds 400 KeV, a barrier layer is added to or is placed in front of the detector plate to transform the X-ray energy to below 400 KeV. The barrier plate transforms any single high energy photon to several low and optimal energy photons which excite the phosphor compound. The barrier plate may comprise or consist for example of aluminum or any other special metal for high energies and its thickness may vary depending on the X-ray energy that should be slowed down.

Some non-limiting examples of phosphor compounds are shown in Table 1 below, as well as their dopants (substances in a minute proportion that produce substitutions in the network of the phosphorescent and facilitate electronic transitions and which are responsible for the color); the function of each one will be explained in more detail below.

TABLE 1

Examples of phosphorescent materials.

| Phosphorescent | Activator | Color |
|---|---|---|
| $Zn_2SiO_4$ willemite | $Mn^{2+}$ | green |
| $Y_2O_3$ | $Eu^{3+}$ | red |
| $CaMg(SiO_3)_2$, diposide | Ti | blue |
| $CaSiO_3$, wollastonite | Pb, Mn | Yellow, orange |
| $(Sr, Zn)_3(PO_4)_2$ | Sn | orange |
| $Ca_5(PO_4)_3(F, Cl)$ fluoropatite | Sb, Mn | "White" |

Excited Electron States

When an atom absorbs energy, an electron transition occurs from a ground state to an excited state. When a molecule is excited, the electrons can enter empty molecular orbits of higher energy, and depending on the different possible configurations, can form various excited states.

Figure 18:
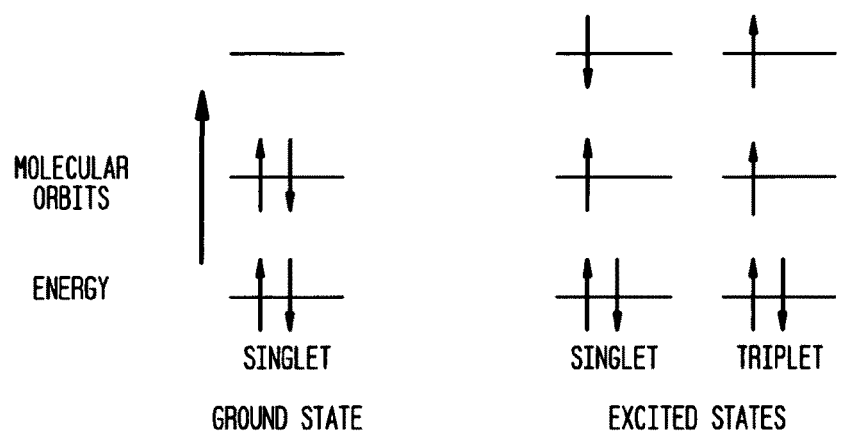
FIG. 18 shows a schematic diagram of the typical arrangements in molecular orbits for the ground, singlet and triplet states.

If the electrons take the same spin orientation as in the ground state, the resulting spin is zero and this excited state is called a singlet. If a spin has a total value equal to one, the excited state is called a triplet, as shown in FIG. 18. In general, triplet states produce phosphorescence, because they take longer to reach their ground state, and singlets produce fluorescence.

Phosphors

Figure 19:
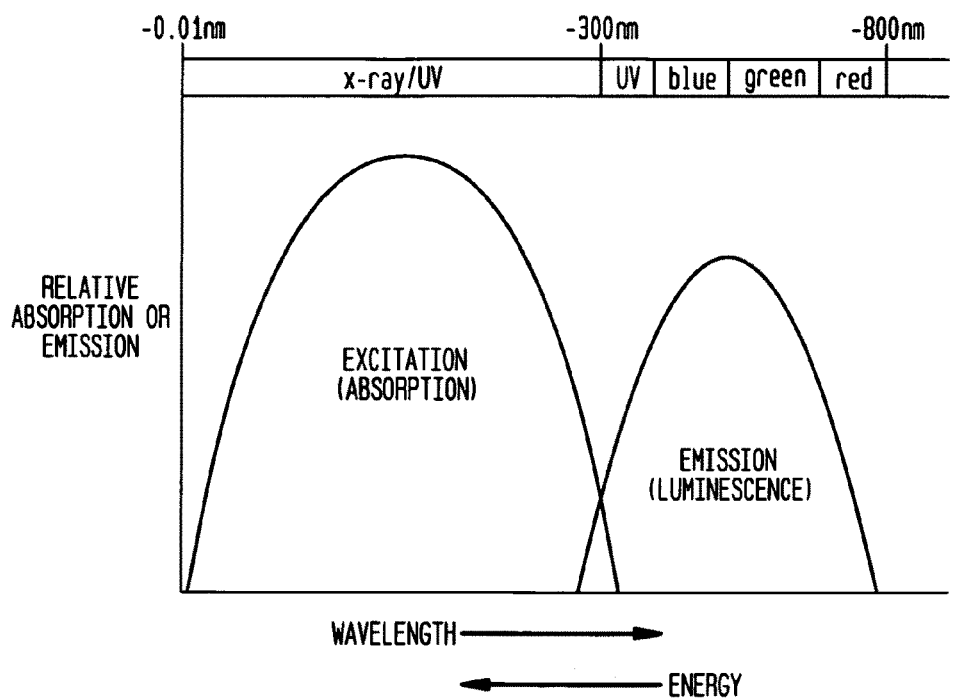
FIG. 19 shows a diagram of energy absorbed and emitted by a phosphor.

Generally speaking, a phosphor is a substance that exhibits phosphorescence. Generally, phosphors absorb some type of invisible radiation and more or less quickly convert it into visible radiation, as shown in FIG. 19. Some phosphors absorb radiation and emit it slowly. Thus, phosphors are also substances capable of storing light for a certain amount of time.

One of the first known phosphors was barium platinum cyanide. This was the substance employed by Roentgen in the discovery of X-rays, for example. However, this substance is no longer used, as it is very toxic, expensive and not very efficient. Substances such as, for example, zinc sulfide with minute impurities are much cheaper, more luminous and safer.

Another important application of rare earth based luminophors is their utilization in so-called X-ray intensifier screens. $CaWO_4$ was the first luminescent material used in the manufacturing of X-ray intensifier screens. In the last 20 years various materials have been studied with the purpose of improving this technology, employing new materials in which the luminophors are rare earths. Among the best used phosphors include $Gd_2O_2S$:Tb (green); LaOBr:Tm (blue); $YTaO_2$:Nb or Tm (blue). The oxysulfides of rare earths are materials that show a great luminescent efficiency in addition to an excellent chemical stability. The composition of the most preferred rare earth phosphorescent elements used in the present invention are: Gadolinium oxysulfide, lanthanum oxysulfide, yttrium oxysulfide and lanthanum oxybromide, as shown in Table 2 below.

TABLE 2

Important Rare Earth Oxysulfides

| Gadolinium oxysulfide | ($Gd_2O_2S$: Tb) Activated by terbium |
| Lanthanum oxysulfide | ($La_2O_2S$: Tb) Activated by terbium |
| Yttrium oxysulfide | ($Y_2O_2S$: Tb) Activated by terbium |
| Lanthanum oxybromide | (LaOBr) |

Photoluminescent materials generally require a guest crystalline structure including but not limited to ZnS, $CaWO_4$, $Zn_2SiO_4$, etc. The guest crystalline structure is doped with a minute quantity of an activator. Preferably, the activator is a cation selected from the group consisting of $Mn^{2+}$, $Sn^{2+}$, $Pb^{2+}$, and $Eu^{2+}$. Sometimes, a second type of dopant is adhered that acts as a sensitizer. A sensitizer is defined as a compound capable of emitting light after having received energy from a molecule previously excited in a chemical reaction.

The emitted radiation, which defines the characteristic color of the luminescence, depends on the nature of the phosphor used and not on the exciting radiation.

A phosphor for X-rays must be a good absorbent of X-rays, a high-density compound that contains elements with high atomic numbers. Preferably, these compounds are selected from the group consisting of $CaWO_4$, $YTaO_4$, $Gd_2O_2S$ and LaOBr. A phosphor for X-rays must also achieve a proper efficiency in the conversion of X-rays into visible light. The efficiency normally being in the interval between 5 and 20% of the energy of the UV-visible light versus the energy of the X-rays absorbed by the phosphorus. Most of the energy absorbed is lost thermally.

Figure 20:
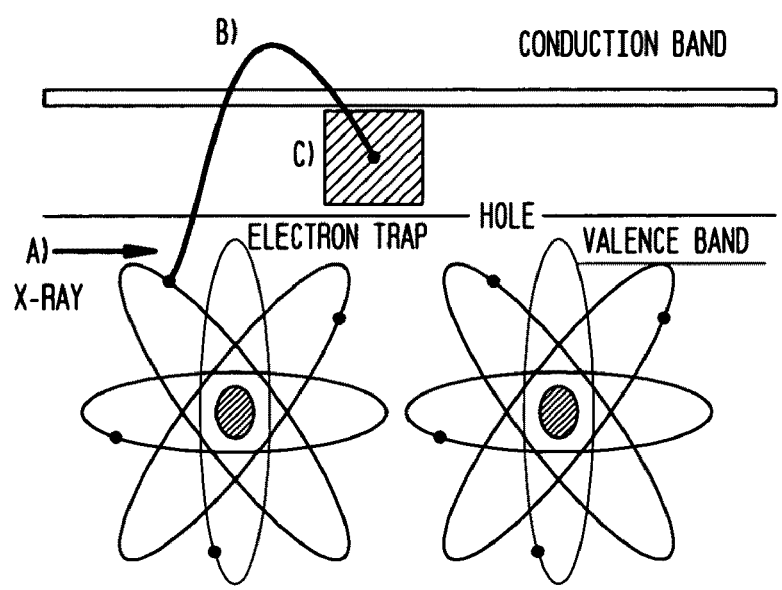
FIG. 20 shows a schematic representation of how the X-rays interact with the phosphor. (A) X-ray arrives; (B) Electron (e) jumps to conduction band; (C) and e is trapped.

When X-rays are shot onto one of these phosphor plates, the X-ray beam interacts with the material of the phosphor, freeing electrons from the atoms of the impurities (dopants such as, for example, europium, samarium, or terbium). This is equivalent to the electrons passing from the energy levels of the valence band to the energy levels of the conduction band, as shown in FIG. 20.

Once in the conduction band, many of these electrons are trapped by energy states slightly below the minimum energy of the conduction band, and remain held in them with a certain half life. If they are to be released before they decay after this amount of time, the phosphor must be bombarded with a beam of photons, of an appropriate energy, that returns them to the conduction band and they remain free in the structure.

Once free in the conduction band, they can decay to the valence band, emitting visible light.

This entire process is produced due to the fact that electrons from the conduction band are captured by impurity atoms from the dopant material (such as, for example, europium, samarium, terbium, etc.) which would have previously released an electron through the action of the X-rays.

Luminescent Inorganic Solids

Phosphorus, an inorganic solid material, is a photoluminescent substance that requires a crystalline structure, a guest and an activator. The activators are usually transition metals, main groups or rare earth ions. The activator is a dopant that creates substitutional defects in the "guest" crystalline structure. This dopant is preferably selected from the group consisting of MgO, ZnO and $Al_2O_3$. The luminescence comes from the activators and is generally found in x=0.1 atomic ratio.

In order to create a solid detector, a compromise must be reached between two opposing criteria. First, the material must be capable of supporting a large electrical field, so that the electrons and the ions can be gathered to form an electronic pulse. Furthermore, in the absence of radiation, the current flow must be minimal or zero so that the background noise is low. Second, the electrons must be easily extracted from the atoms, and in large numbers, by the radiation, and the electrons and ions must be capable of easily travelling in the material.

Inasmuch as the first condition appears to require an insulating material, while the second suggests using a conductor, a good compromise is, for example, to use a semiconductor.

Scintillator counters solve the dilemma of the choice of the material in the following way: the electrons that are formed in the ionization process are not the same as those for the electronic pulse. The intermediary between both is the normal light.

The complete process is as follows. The incidental radiation interacts with the atoms and the molecules of the material, exciting them. Then the excited states de-excite, emitting fluorescent visible (or near-visible) light. Then the light reaches a photosensitive surface picking up photoelectrons. The electrons are accelerated and multiplied to form an electronic pulse in the photomultiplier tube. (In the case of laminated scintillators, which are preferably used in the present invention, the amplification is achieved with the inclusion of inorganic oxides that act as a reflecting layer, avoiding the loss of photons).

It is noted that the primary characteristics of a phosphor are: (i) high efficiency in the conversion of X-ray photons into visible photons; (ii) high capacity to arrest X-ray radiation; (iii) high spatial resolution; (iv) being highly uniform; (v) good distribution of light in the emission spectrum; and (vi) light with a small decay time.

Variation in the thickness of the phosphor samples, in the weight of the coating, the size of the grain, and the finish of the plate give rise to different results in the light emitted and the resolution.

Investigation of the Concentration of the Phosphor Compounds in the Detector Plate During experimentation, the yield increased with the phosphor compounds in the detector plates in the range from about 5 to about 25 $mg/cm^2$. Preferably, the optimal concentration for the phosphor screen is about 10 $mg/cm^2$. This is what is preferably required by the system of the present invention in order to obtain an energy in the range of 5-25 KeV. These values must determine the design of the detector plate, introducing bases that give these output energies, since the energy that they receive is much greater.

Investigation of the Concentration of the Phosphor Compounds in the Detector Plate In exemplary embodiments of the present invention the thickness of the detector plate can be from about 0.2 to about 3 mm, or, for example, about 1 mm.

Investigation of the Presence of a Reflector Compound in the Detector Plate

The yield in transforming X-rays into visible light by the detector plate increased with the presence of a reflector/amplificator compound such as an aluminum compound within the mixture that forms the detector plate and not as just a coating layer to said plate. Preferably, the amount of the reflector/amplificator compound in the detector plate can be, for example, up to a maximum of about 30% by weight. The uniformity of the distribution of light was poorer for phosphors with an aluminum coating (±15% maximum). A coating of an absorbing agent produced a decrease in the yield (maximum of 35%). The presence of an aluminum compound mixed within the detector plate did not influence the uniformity of the distribution of light from the phosphor.

Investigation of the Particle Size of the Phosphor

The yield of the light did not change linearly with the particle size. In exemplary embodiments of the present invention the particle size of the phosphor compounds can be from about 2 to about 10 µm. In exemplary embodiments of the present invention a particle size of about 4 µm resulted in an optimal yield for emission of light. The uniformity of the distribution of light generally increased with the increase of the particle size.

In exemplary embodiments of the present invention, selection of materials for detector plates can, for example, consider (i) the fraction of the incidental energy that appears as light;

(ii) the efficiency (the probability that the radiation will be absorbed); (iii) the response time; and (iv) the resolution in energy.

In exemplary embodiments of the present invention inorganic materials used as a crystalline network can be gaps with ionic bonds, composed with a band gap in the UV region. The activator has discrete energy levels associated with the network and these levels can be modified with different values as a function of the type of activator and the local environment in the crystalline structure.

In exemplary embodiments of the present invention, the activator can directly absorb the excitation energy, thus promoting an electron from the ground state of the atom to excited states. Or, for example, this energy can be transferred from the crystalline network to the activator.

When the activator ions were found to be very little influenced by the structure of the crystalline network, they showed a luminescence with a very narrow emission line characteristic of the activator atom. This narrow emission line was common for activators from ions of rare earths such as $Tb^{3+}$, $Tm^{3+}$, or $Eu^{3+}$, whose optical transitions are exclusively between the energy levels of f-orbits. When the energy levels of the activators were found to be very modified by the crystalline structure, the emission of the activator transitions were generally of a more complicated nature and were often only partially understood.

A strong influence of the crystalline structure gave rise to the appearance in the luminescence of a wide band of emission. Furthermore, the same activator in two crystalline structures that significantly modified the energy levels of the activator gave rise to a luminescence of one color in one matrix and another color in the other.

Figure 21:
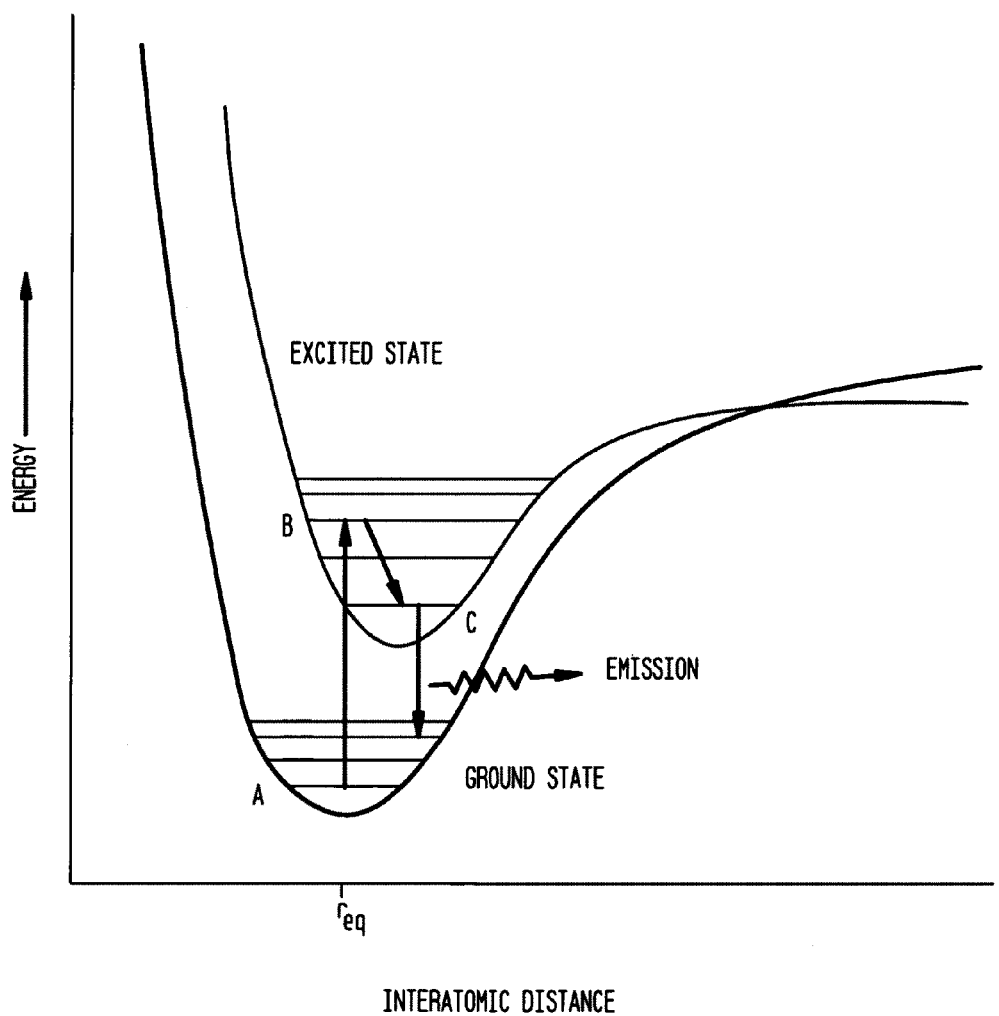
FIG. 21 shows a diagram of the luminescence process.

The diagram of FIG. 21 illustrates luminescence of a phosphor with ionic bonds where the activator is excited from the ground state (A) to higher energy levels (B). Part of this absorbed energy is lost in the crystalline structure in the form of heat and the excited ion relaxes, falling to a less energetic excited state (C). The activator goes back to the ground state (A), losing energy through light emission. It is noted that the excitation energy is greater than the emission energy. The reduction of energy or the increase in the wavelength is known as the Stokes shift.

A phosphor must exhibit a good absorption of X-rays. A high absorption of X-rays is necessary to minimize exposure time and maximize the signal to noise ration in order to optimize the image. The characteristics of some of the most widely sold phosphors are shown below in Table 3.

TABLE 3

Characteristics Of Exemplary Phosphors

| Phosphor | Conversion efficiency (%) | Density (g cm$^3$) | K-edge (keV) | Emission (color, width) |
|---|---|---|---|---|
| CaWO$_4$ | 5 | 6.12 | 70 | blue, broad |
| BaFCl:Eu | 16 | 4.56 | 37 | UV/blue, broad |
| LaOBr:Tm | 18 | 6.10 | 40 | UV/blue, line |
| Gd$_2$O$_2$S:Tb | 19 | 7.34 | 50 | green, line |
| M'-YTaO$_1$ | 8 | 7.57 | 67 | UV, broad |
| M'-YTaO$_4$:Nb | 8 | 7.57 | 67 | blue, broad |

Figure 22:
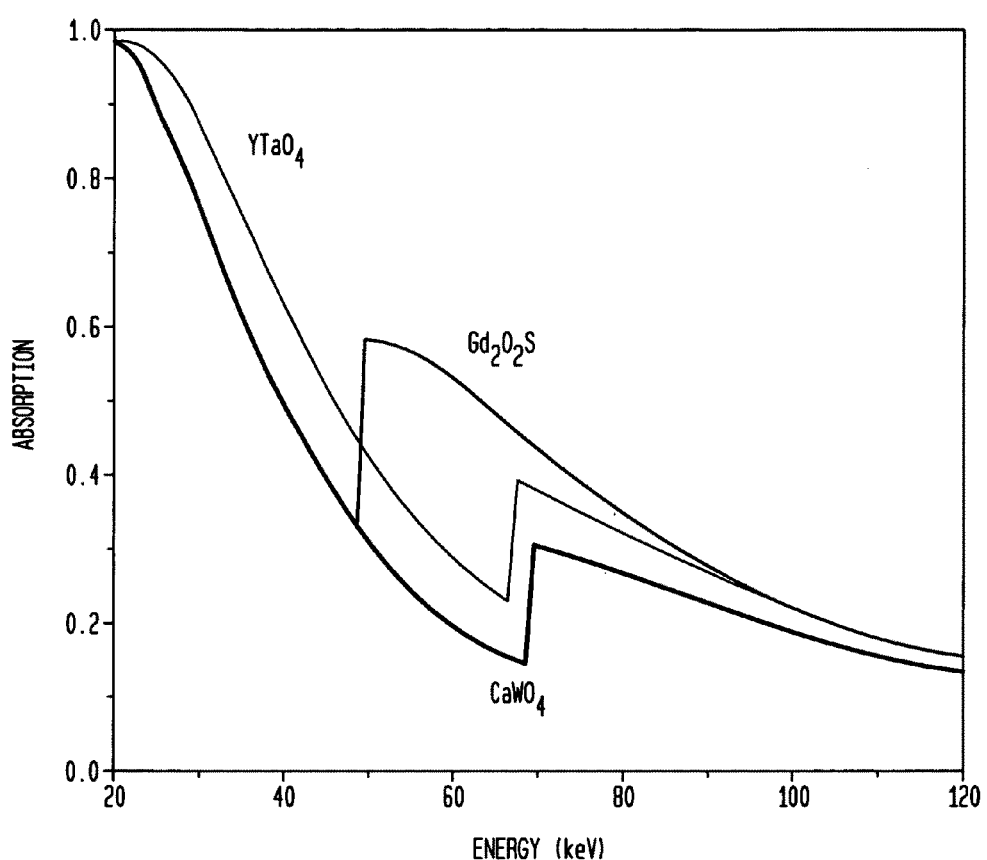
FIG. 22 shows the absorption of various phosphors as a function of the X-ray photons. The absorption is into the matrix of heavy elements, and a high luminescent efficiency (5-20%) is achieved.

FIG. 22 shows the absorption of various phosphors as a function of the X-ray photons. The absorption is into the matrix of heavy elements resulting in a high luminescent efficiency from about 5 to about 20%.

Luminescence of Gadolinium Oxysulfide

Materials that emit light in the UV/visible range after the absorption of high-energy photons are known as scintillators. Based on this property, these materials have numerous applications as radiation detectors in diagnostic medicine, industrial inspection, nuclear medicine, etc.

Due to their high luminescence, rare earth oxysulfides, such as $Gd_2O_2S$:Tb (green) and $Gd_2O_2S$:Eu (red), are especially used in the manufacturing of X-ray intensifier screens for medical diagnosis or television tubes. $Gd_2O_2S$:Tb (gadolinium oxysulfide activated with terbium) exhibits a brilliant green luminescence in addition to a high efficiency after its activation with X-rays.

Figure 23:
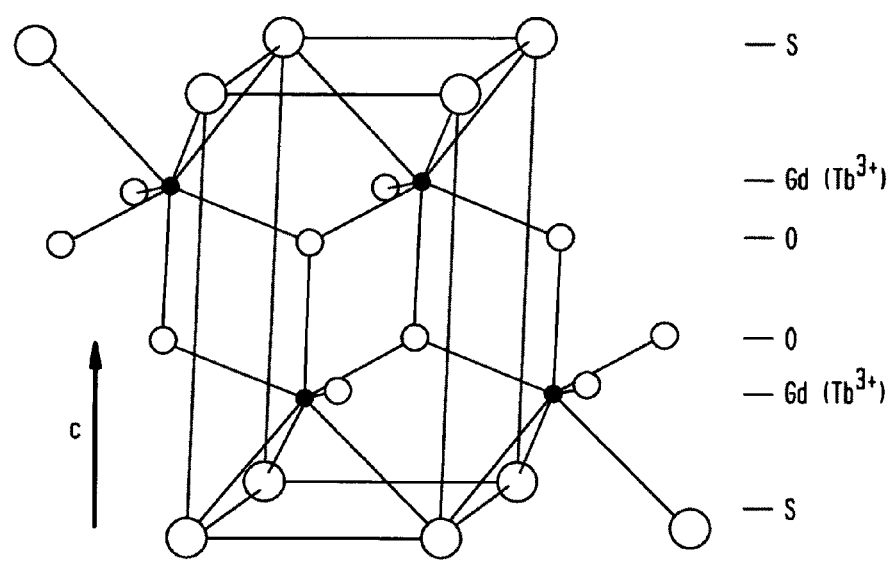
FIG. 23 shows the crystalline structure of $Gd_2O_2S:Tb$.

The crystalline structure of $Gd_2O_2S$:Tb is (trigonal) hexagonal, and is shown in FIG. 23. Its framework parameters are: a=3.851 and c=6.667 Å, it has a high density, 7.34 g/cm and a large capacity for absorption of X-rays, the $K_{edge}$ of Gd is 50 kev. Its structure is constructed by sharing layers with a monolayer of trigonal antiprisms formed by units of $GdO_4S_3$.

Both $Gd_2O_2S$ and $Tb_2O_2S$ have the same crystallographic structure and a similar ionic radius ($Gd^{3+}$=100 and $Tb^{3+}$=98 pm), so the perfect formation of solid solutions is expected.

Figure 24:
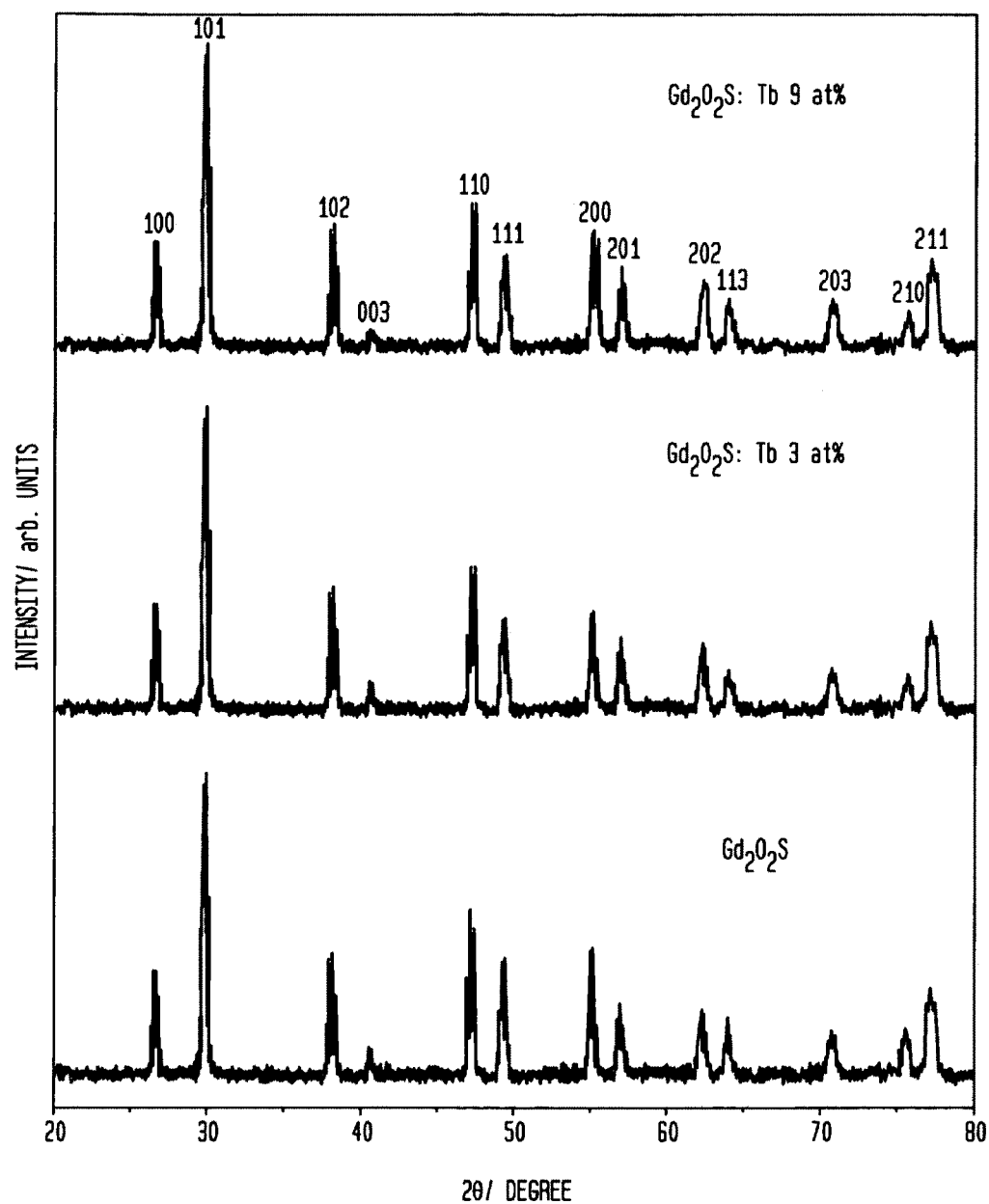
FIG. 24 shows diffractograms for $Gd_2O_2S$ and samples doped with $Tb^{3+}$.

In order to prove whether the incorporation of terbium exercises some influence on the structure of gadolinium oxysulfide, the diffractograms of $Gd_2O_2S$ and $Gd_2O_2S$:Tb (with different quantities of terbium) were compared; the diffractograms of the doped samples were equal to that of the $Gd_2O_2S$, indicating that the $Tb^{3+}$ ions occupy the sites of the $Gd^{3+}$ (FIG. 24).

Figure 25:
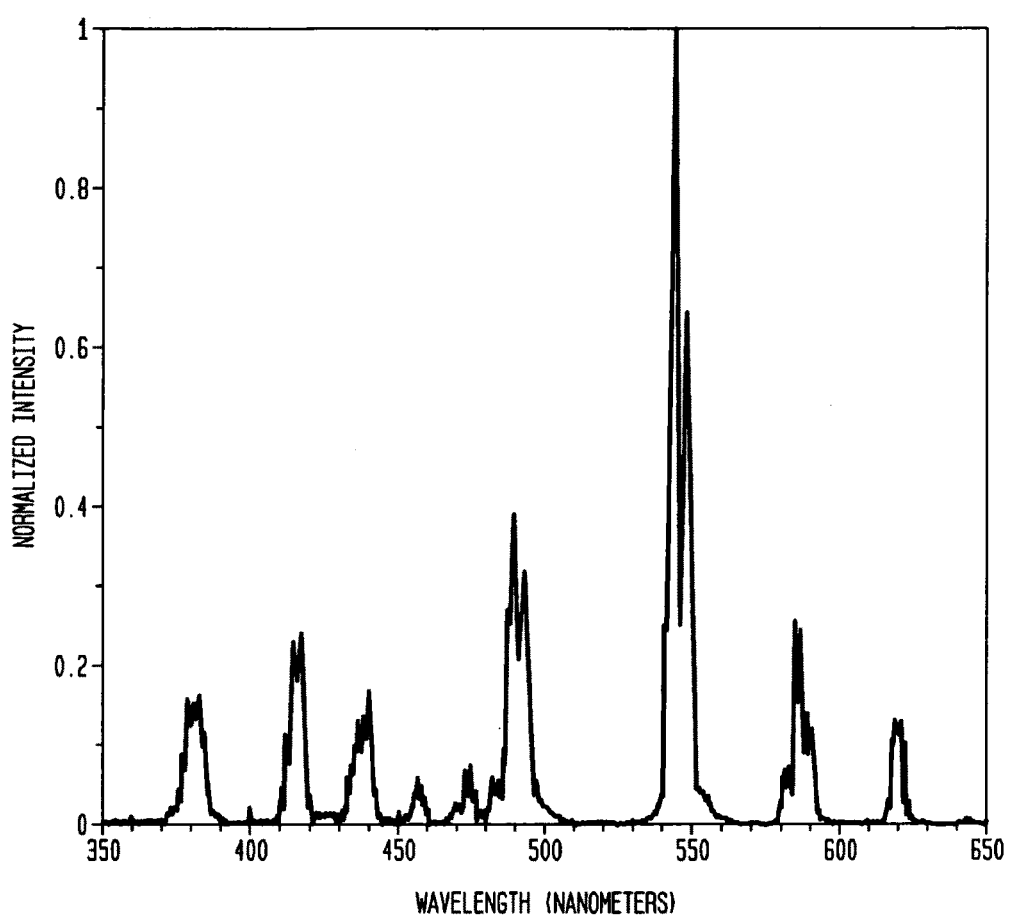
FIG. 25 shows an emission spectrum of $Tb^{3+}$ in $Gd_2O_2S:Tb$ due to excitation with X-rays.

Although gadolinium oxysulfide has been doped with other rare earth trivalent activator ions, more efficient (19%) X-ray scintillators were obtained doping with $Tb^{3+}$. $Gd_2O_2S$:Tb predominantly emits a green light with a narrow line in its emission spectrum (FIG. 25). However, the color of the luminescence depended on the activator concentration, since the concentration was decreased, a blue emission was observed due to an increase of intensity in the peak of the emission spectrum in the region close to 500 nm.

The emission of the terbium occurs after its direct excitation or by a transfer of energy through $Gd^{3+} \rightarrow Tb^{3+}$, or through matrix $\rightarrow Tb^{3+}$.

$Gd_2O_2S$:Tb is used in X-ray intensifier screens because of the brilliance of the green emission that it exhibits after excitation. Its high density (7.44 g/cm$^3$), the high absorption of X-ray radiation photons, in addition to the high intrinsic conversion efficacy (approx. 20%) and the chemistry of the $Tb^{3+}$ bring about a high yield.

Particle form and size also play an important role, it being the spherical particles with diameter comprising between 3-10 μm that give rise to optimal packing conditions. The optical properties of scintillators depend on the size and the morphology of the particle. Both $Gd_2O_2S$ and $Gd_2O_2S$:Tb exhibit spherical particles with an average size of 250 nm, indicating that the presence of a dopant does not produce significant changes in the form and size of particle. In the case in which particle aggregates appear, a suitable capacity for the packing of the particles is a much desired characteristic for scintillators used in X-ray intensifier screens.

Figure 26:
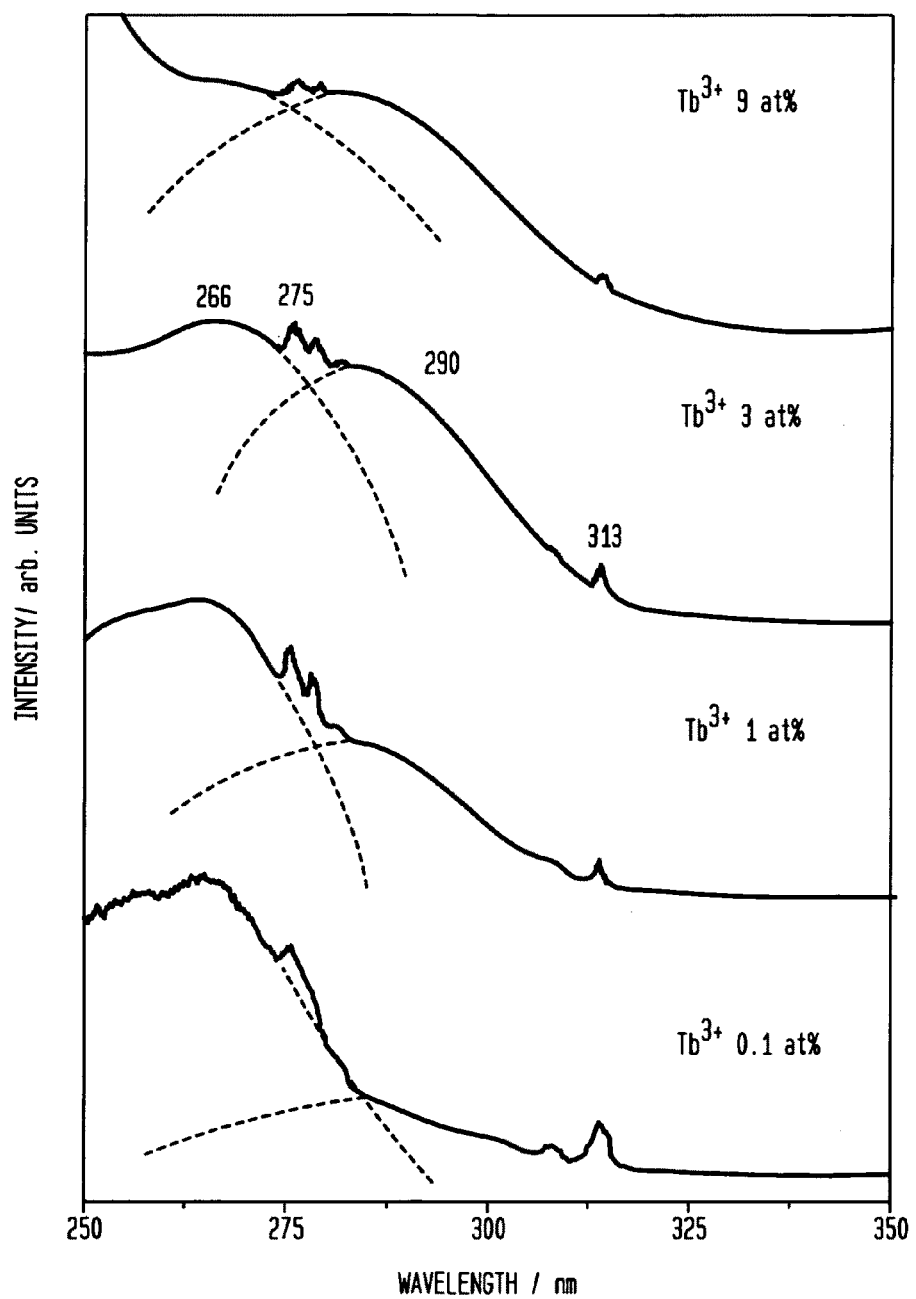
FIG. 26 illustrates the excitation spectrum obtained with an emission wavelength of 544 nm (most intense transition of $Tb^{3+}$, $^5D_4 \rightarrow ^7F_5$)

The excitation spectrum obtained for an emission wavelength of 544 nm (most intense transition of $Tb^{3+}$, $^5D_4 \rightarrow ^7F_5$) is shown in FIG. 26, where two wide bands were observed at 266 and 290 nm and two peaks of lines at 275 and 313 nm.

The excitation lines may be attributed to the f→f transitions of the $Gd^{3+}$ that correspond with $^8S \rightarrow ^6I$ and $^8S \rightarrow ^6P$ respectively. The presence of the transitions of the gadolinium in the excitation spectrum made clear the transfer of charge between the $Tb^{3+}$ ion and the $Gd^{3+}$ ion. The energy transfer can occur from levels $^6I$ or $^6P$ of the Gd to higher energy levels of the $Tb^{3+}$, configuration $4f^75d$ or $4f^8$.

It is important to point out that the intensity of the bandwidth at 290 nm increases with the increase in the concentration of $Tb^{3+}$, while changes in the band are not observed at 266 nm. This behavior implies that the band that appears at 290 nm may be attributed to the $4f^8 \rightarrow 4f^75d$ transitions of the $Tb^{3+}$ and the emission takes place after a non-radioactive decay at the $^5D$ level. The excitation of the matrix is expected at 266 nm, the energy transferred to $Tb^{3+}$ centers by free electrons.

Figure 27:
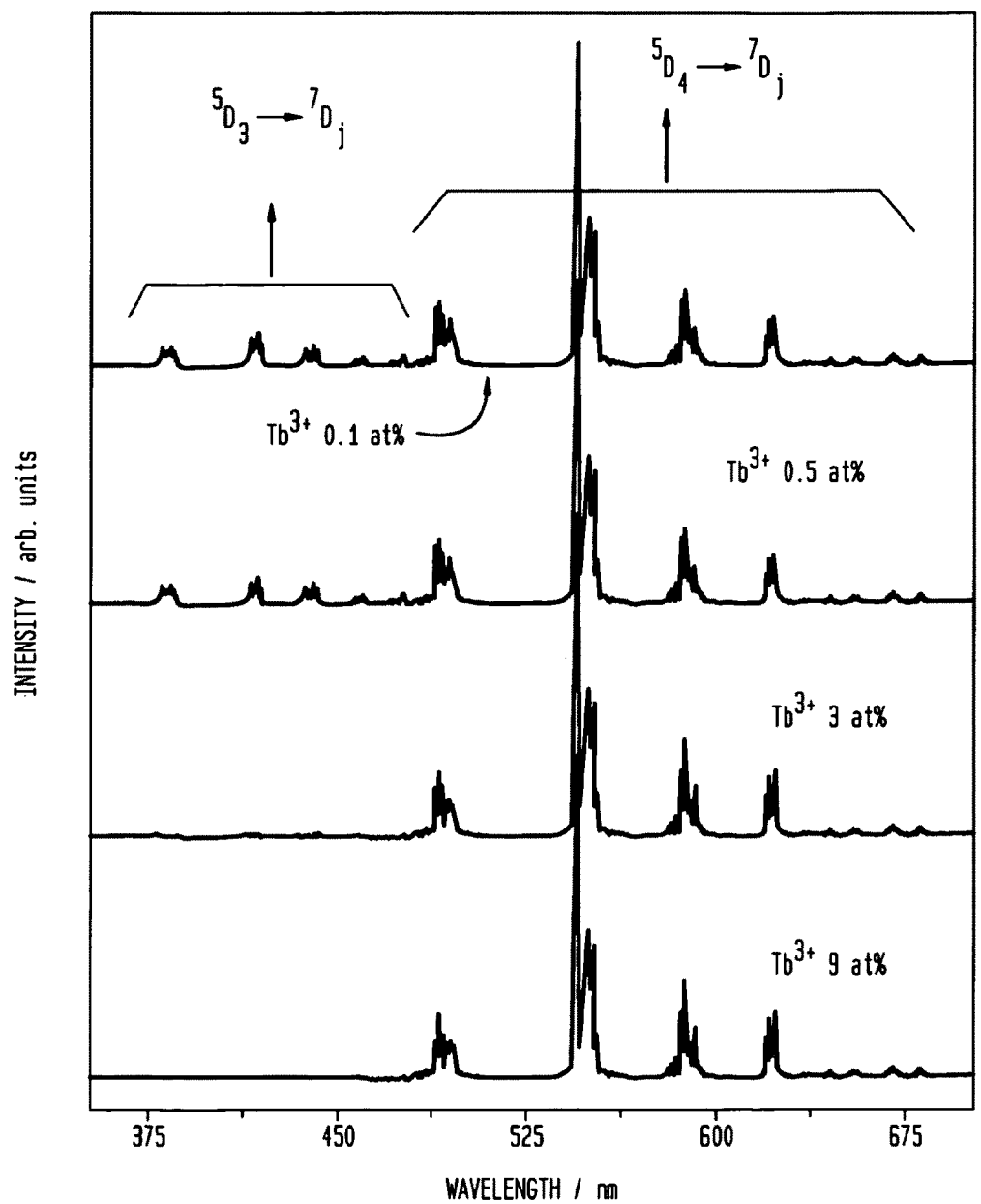
FIG. 27 shows $Gd_2O_2S:Tb$ emission spectra ($\lambda_{ex}=266$ nm), with different quantities of $Tb^{3+}$.

It is noted in the emission spectrum that for low concentrations of $Tb^{3+}$ the blue emission is observed from the $^5D_3 \rightarrow ^7F_j$ transition. When the concentration of the activator increases, the blue emission disappears and only the green emission is observed in the spectrum of the $^5D_4 \rightarrow ^7F_j$ transition (FIG. 27).

The color of the emission shifts from greenish-blue to green with the increase in the concentration of $Tb^{3+}$. The color of the composition of the $Tb^{3+}$ emission also affects the lifespan of the scintillator, which is related to the spatial resolution of the image. The lifespan averages at ambient temperature for the $^5D_4 \rightarrow ^7F_5$ and $^5D_3 \rightarrow ^7F_5$ transitions are shown in Table 4. It can be observed that the blue emission ($^5D_3 \rightarrow ^7F_5$) has a smaller lifespan than the green one ($5D_4 \rightarrow ^7F_5$).

TABLE 4

Lifespan Averages At Ambient Temperature For The $^5D_4 \rightarrow ^7F_5$ And $^5D_3 \rightarrow ^7F_5$ Transitions

| $\lambda_{ex}$/nm | Transition | $\lambda_{em}$/nm | Transition | Lifetime ($\tau$)/ms |
|---|---|---|---|---|
| 266 | VB→CB | 544.5 | $^5D_4 \rightarrow ^7F_5$ | 1.5 |
| 275 | $^8S \rightarrow ^6I_{3/2}$ ($Gd^{3+}$) | 544.5 | $^5D_4 \rightarrow ^7F_5$ | 1.5 |
| 290 | 4f→5d | 544.5 | $^5D_4 \rightarrow ^7F_5$ | 1.3 |
| 266 | VB→CB | 417.5 | $^5D_3 \rightarrow ^7F_5$ | 0.3 |
| 275 | $^8S \rightarrow ^6I_{3/2}$ ($Gd^{3+}$) | 417.5 | $^5D_3 \rightarrow ^7F_5$ | 0.3 |
| 290 | 4f→5d | 417.5 | $^5D_3 \rightarrow ^7F_5$ | 0.2 |

$Gd_2O_2S$:Tb Synthesis Methods

The classic method for synthesis of these compounds is by a reaction in a solid state of the oxides of the rare earths with sulfur with a flux, (S, $Na_2CO_3$) at 1100° C.:

$$Gd_2O_3 + xTb_4O_7 + S_{excess} \rightarrow Gd_2O_2S + \text{byproducts}$$

Preparation Method for a Cold Isostatic Press (CIP) Pretreatment

This is a reaction in a solid state between starting materials and different types of fluxes. The synthesis can be carried out both at normal pressure and at isostatic pressure using the following reactants: $GdO_3$, $Tb_4O_7$, S and the following fluxes: $Na_2CO_3$, $K_2CO_3$ and $K_3PO_4$.

The starting materials, $GdO_3$, $Tb_4O_7$ and the flux, were mixed and crushed in an agate ball mill for 30 min. The sample was separated into two parts to be used in two different treatments: CIP and NOR. The CIP sample was compressed using a cold isostatic press at 200 MPa for 3 min. (1974 atm), and the NOR mixture was introduced into a corundum crucible and compressed manually. The entire process was carried out in a reducing atmosphere ($H_2/N_2$: 10/90) at 350-1250° C. for 90 minutes. Finally the samples were washed several times with HCl and $H_2O$, then dried and sifted.

Preparation Method for Combustion Reaction

The combustion method for the preparation of said compound consisted of a combustion reaction starting with the mixed metallic nitrates and an organic combustible, dithiooxamide (($CSNH_2)_2$).

Reactants:
Gd($NO_3$)$_3$.6$H_2O$ (99.999%)
Td($NO_3$)$_3$.6$H_2O$ (99.999%)
($CSNH_2$)$_2$ First of all, the nitrates were dissolved in water and mixed in stoichiometric quantities. They were then melted in an oven at 100° C. During the cooling of the mixture of metallic nitrate reactants, the appropriate amount of organic solvent was added, which was mixed and ground with the nitrate.

After 24 hours of dehydration in a dryer, the mixture was heated in a tubular oven to the ignition temperature, $T_i$=300-350° C. During the heating, the decomposition reaction took place, forming precursors. Due to the large amount of heat produced in the exothermic reaction between the metallic nitrates and the combustible, the reactants were heated locally to a high temperature, called a flame temperature, $T_f$, and the metallic oxysulfide was quickly formed.

Flux Thermal Method

This is a synthesis method starting from mixtures of precursor oxides, a flux, mineral additives and a source of sulfur.

Reactants:
$GdO_3$
$Tb_4O_7$

Fluxes:
$Na_2CO_3$
$Li_2CO_3$

Mineral additives:
$Na_3PO_4$.12$H_2O$
$Na_4P_2O_7$.10$H_2O$

Sulfur source:
S
$Na_2S_2O_3$.5$H_2O$

This method consisted of the preparation of the mixtures starting with the precursor oxides and the sulfur source in the presence of a basic carbonate flux. The alkaline phosphate was used as a mineral additive to control the particle size.

The samples were calcinated at 1200° C. in air, for 4 hours in closed aluminum to crucibles. Next, a cleaning stage was conducted with diluted HCl.

Sulfur Vaporization Method

This method of synthesis is by vaporization of sulfur over the carbonate precursors of the rare earth cations.

Reactants:
$GdO_3$
$Tb_4O_7$
$GdCl_3$
TbCl
Urea
Elemental sulfur
Gases: Ar, $H_2/N_2$ mixture (3%/97%).

The carbonates of the rare earths were used as precursors for the oxysulfide. They were prepared by heating of the metallic chlorides in a urea solution at 85° C. under continuous agitation for 2 hours.

The oxysulfide samples of the rare earths were prepared by deposition of the sulfur over the carbonates. A tube of quartz was used, in which were placed the aluminum crucibles with the precursors or with the elemental sulfur in a tubular two-zone oven. In the first zone, the elemental sulfur was heated to 300° C., while in the second zone the precursors were heated to 750 and to 780° C. for 2 hours at both temperatures. The quartz tube was completely sealed to maintain an atmosphere free of oxygen. Thus, the quartz tube was purified with a stream of argon through the system during the reaction and during the cooling. The samples were then heated to 900° C.

for 2 hours in the same way described above, but in this case a dynamic atmosphere of the $H_2/N_2$ (3%/197%) mixture was maintained.

Exemplary Preparation Of Plates

In exemplary embodiments of the present invention, detector plates can be prepared, for example, by mixing the ingredients shown below in Table 5 at room temperature (or at about 20° C.) at a pressure of about 700 mm Hg.

TABLE 5

Ingredients For Detector Plate Preparation

| Compounds | Amounts |
| --- | --- |
| Gadolinium oxysulfide | 4 g |
| Sodium silicate neutral solution QP | 50 mL (Density 1.365 kg/L) |
| Aluminum acetate | 25 mL (1% w/v) |
| Dopant | 20% w/w of the total weight of mixture |

In fact, several mixtures were prepared by adding variable amounts of $Gd_2O_2S$:Tb of inorganic luminescent pigment (in order to result about 0.05 g to about 0.2 g/cm² of solid plate preferably 0.07 g/cm² of solid plate) to quantities of a dopant (MgO, ZnO or $Al_2O_3$) which range from 10% to 50% by weight of the total weight of the mixture which includes the below liquid ingredients. The mixtures were completed with sodium silicate and aluminum acetate in a sufficient amount (40-60 ml silicate and 20-30 ml aluminum acetate (1% w/v)) to avoid the formation of agglomerates.

Reactants included gadolinium oxysulfide, sodium silicate, aluminum acetate, dopant. The syntheses were carried out through mixing the reactants by continuous agitation. For 10 cm×5.5 cm (aluminum) plates, gadolinium oxysulfide (between 3 and 6 g) and the indicated amount of dopant (between 10 and 50% by weight) was added over sodium silicate (between 20 and 100 ml) maintaining constant agitation. Next, 1% aluminum acetate was added, maintaining the agitation for 30 minutes. It was left to rest for 5 minutes and deposited on the aluminum plate. After the phosphor has been deposited over the plate, the floating excess was removed, and [the plate] is left to dry 1 or 2 hours in air and placed in the heater at 90° C. for 24 hours.

Prior Art Detectors

Figure 28:
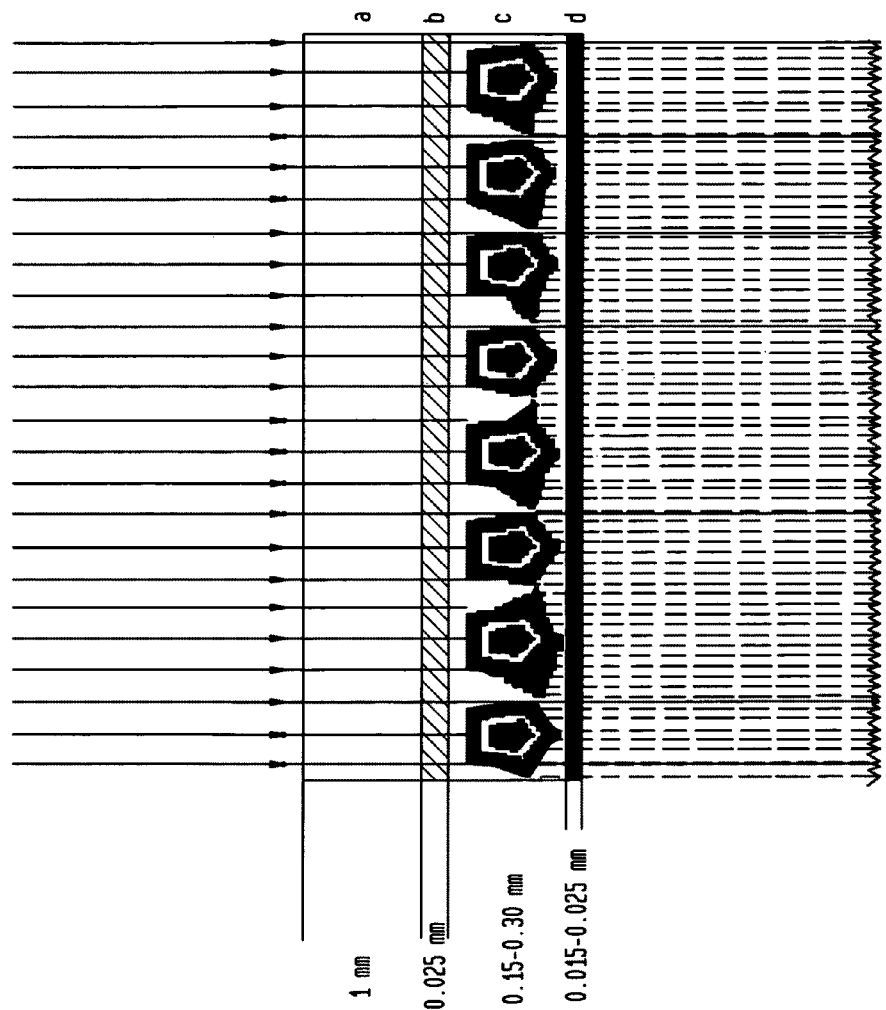
FIG. 28 shows the structure of an intensifier screen according to an exemplary embodiment of the present invention, including base, reflector layer, phosphorescent material layer, and protective layer.

Conventional intensifier screens are a flexible sheet, composed of a material capable of interacting with X-rays. Normally these screens have four layers: a protective layer, the phosphorescent material, a reflector and the base, as shown in FIG. 28. The protective layer is the closest to the detector and serves to protect the screen against external harm. It is composed of a transparent material that is meant to minimize static electricity.

The layer of phosphorescent material that is made up of an emulsion containing a compound capable of interacting with X-ray photons, produces and transmits a visible light.

In exemplary embodiments of the present invention an exemplary phosphorescent material can fulfill a series of characteristics: high atomic number (they interact with more X-rays), emits a large quantity of light when interacting with X-rays, brightness or emission of light that remains once the X-ray has gone away is minimal, distribution of the phosphorescent solid in the emulsion must be uniform so that the luminous emission can have the same intensity at each point on the screen.

In exemplary embodiments of the present invention, intensifier screens can differ by the type of phosphorescent solid, by the different thickness of the fluorescent layer, and by the concentration and size of the crystals of the phosphorescent solid.

In exemplary embodiments of the present invention an exemplary reflector layer can be composed of, for example, titanium dioxide. This layer is used to avoid losing the light from the emitted photons.

Finally, the base, which is the layer farthest from the detector, is the thickest (about 1 mm) and can, for example, serve as a mechanical support to the layer of phosphorescent material.

X-Ray Detectors According to the Present Invention

The principal difference between prior art intensifier screens and exemplary detector plate "phosphorescent paper" of the present invention is the absence, in the latter, of the protective and reflector layers described above.

Surprisingly, the protective layer is not needed due to the fact that the above-described mixture, where the phosphorescent solid is dispersed, creates a small protective layer on the surface of the phosphorescent solid due the presence of a protective compound like a silicate compound, preferably sodium silicate or potassium silicate. Also, for example, the amount of the protective compound can be, for example, from about 0.01 to about 0.05% w/w of the total weight of the solid plate.

Also surprisingly, the reflector layer is preferably not needed because of the presence in the above-described mixture, where the phosphorescent solid is dispersed, of a reflector/amplificatory compound such as an aluminum compound. The reflector/amplificatory compound is preferably selected from the group consisting of aluminum acetate, barium acetate and zinc acetate, most preferably aluminum acetate. Also preferably, the amount of the reflector/amplificatory compound is from about 1 to about 10% w/w of the total weight of the solid plate.

Another difference is the base where in the intensifier screens of the prior art employ a polyester. The detector plate of the present invention preferably employs different bases which include but are not limited to: polyester, aluminum, glass, etc. The use of different bases is primarily done with the objective of optimizing and improving the efficiency of the phosphorescent solid.

Electrical and Mechanical Controls

FIG. 11 is a schematic diagram showing the electrical and mechanical operational controls according to exemplary embodiments of the present invention.

An electrical power source 166 delivers power to the X-ray source 36, the rotor motor and brake 162, and the detector 46 which are mounted on the rotor 32. The power is delivered over cables through a cable handling system indicated schematically at 176 that spreads the cables into a linear array and has equipment that alternatingly takes up the slack of the cable and then rewinds it during the reciprocating motion of the rotor. This can prevent the cable from tangling, and can reduce wear and breakage.

A coolant supply 164 consists of a pump and a heat exchanger. It sends coolant liquid (water) through a hose dispensing and rewind system 174 to the x-ray source 36 to remove the excess heat generated by the source, and returns the coolant to the heat exchanger to cool. If desired, or if necessary, refrigeration of the coolant can be provided as well.

In exemplary embodiments of the present invention, a drive control unit 168 can be provided. It supplies control signals to the rotor motor and brake system 162, through a cable dispensing and rewind system 178. It also supplies control signals to the rail motor and brake 170 for the cargo container railcar 28 (FIG. 1) to ensure that the cargo container moves in synchronizism with the movement of the rotor.

Preferably, the cargo container is stationary while it is being scanned, and is moved along the rails 48 and 50 to the next scanning position while the rotor is being slowed down at each end of its path, and reverses direction and accelerates to scanning speed in the opposite direction.

The distance for the cargo to be moved is relatively small (e.g. 1.5 meters) so that the movement of the rotor back and forth through the 5° arc segment at each end of its travel path gives sufficient time to move the cargo container to the next scanning position.

Alternatively, the cargo container can move continuously while the x-ray source 36 swings back and forth in the plane 157 (FIG. 13) parallel to the plane of motion of the cargo container to compensate for the motion of the container.

Signals from the detector unit 46 are transmitted through another cabling dispensing and rewind system 180 to the computer 172 where visible images showing the contents of the container are displayed on the screen.

FIG. 12 shows an alternative system which is like the one shown in FIG. 11 except that the coolant supply system 164 and an electrical power generator 182 are mounted on the rotor 32 rather than on the ground. Furthermore, control signals from the drive control unit 168 are transmitted and received by wireless transmission, as indicated at 184, rather than through cables. Similarly, data from the detector 46 is transmitted to the computer also by wireless.

Referring again to FIG. 9, in this exemplary embodiment, antennas 144 and 146 are shown and transceivers (not shown) are used together with the antennas for wireless communication.

This embodiment of the invention has the advantage of not requiring any cabling to be handled as the rotor moves.

When this embodiment is used, the electrical generator 182 and the coolant supply system 164 can be mounted in one of the locations 110, 112 and 114 shown in FIG. 6 so as to maintain the overall balance of the rotor about the rotational axis.

Data Acquisition Software

As described above, in exemplary embodiments of the present invention an exemplary detector system can be based on modular elements, where each element is composed of a scintillator plate and a CCD camera or ICCD camera. For each orientation of the X-ray source, each camera stores an image of a portion of the projection beam, 2D (fan beam) or 3D (cone beam).

The design objectives of the software for image acquisition are: the reading of each one of these images at a sampling rate sufficiently high to ensure that no information is lost; its storage in the computer where the software for reconstruction is located; and the display of raw data (without reconstruction).

To this end, the software includes a module for the configuration of the cameras. This module adjusts the exposure time, the working area of the camera, and all other additional parameters that determine the reading speed, i.e. the number of frames per second, and synchronizes firing of the cameras.

In another software module, the protocols for communication with the camera have been implemented. A software thread serves each of the cameras independently to ensure the reception of all projection.

Another module is responsible for merging all images into one and then storing them to implement the reconstruction algorithm. Also, during the inspection of the container, and before making the reconstruction, it is possible to preview the raw projections.

Besides the acquisition of data from the sensory system, the software allows data entry from simulation software such as, for example, Geant4, CTsim and Take3.

Software Configuration and Calibration of the Scanner

In exemplary embodiments of the present invention, software can be provided for configuration and calibration of the equipment. Due to the configuration, the reconstruction software is tailored to the geometry of the scanner. This will ensure that the software is valid for different scanner modules depending on the size of the containers to be scanned: suitcases, truck, etc. Therefore, one can easily adjust parameters for each particular scanner, such as focal length (distance to the X-ray generator), emitter-detector distance, area of the detector, number of detectors, and angle for each detector in order to arrive at the desired equiangular configuration as well as the correct distance between detectors for equilinear arrangement, etc.

Such software can include, for example, positioning software. Such software can receive signals from the motor and position sensors of the wheel, and can, for example, fit this movement with the rotation of the container (if any). Different lasers positioned along the structure ensure the proper disposal container-detector. In turn, a positioning system guide can insures that the subject, or container, is in the right axis, centered with respect to the x-ray beam.

In order to differentiate between objects according to their densities, other software can be provided to enable measurement of the densities of patterns and storing of them in a database designed for this purpose. The task to determine the density patterns, and therefore the software, is dependent on the machine, and particularly on the X-ray source, detection system, and on the reconstruction software.

Once the equipment is in operation, it can, for example, be periodically calibrated to correct the imbalances and misalignments which can develop during operation. Such physical calibration can be done using positioning software and density calibration, involving reference patterns of homogeneous density. For example, an exemplary system can contain a "calibration phantom", so that a position of the system (when the source is in the lowest point) serves to make a self-calibration. This process that can be repeated from time to time either manually or automatically. By using this test tool one can determine simultaneously (i) signal standardization and dose indicator on monitor, (ii) homogeneity, (iii) spatial resolution, (iv) contrast resolution, (v) alignment of light field and the field of useful beam, (vi) image scale and artifacts. Such a phantom can be, for example, phantom T41014© PTW Freiburg GmbH, which is a completely closed stationary water phantom for high energy photon dosimetry with PTW Farmer chambers.

In exemplary embodiments of the present invention, the calibration software can allow an operator to easily adjust different parameters of the scanner to match the densities of the patterns. It is noted that system noise in general limits the contrast/resolution, and calibration can, for example, help to reduce such noise.

Figure 29:
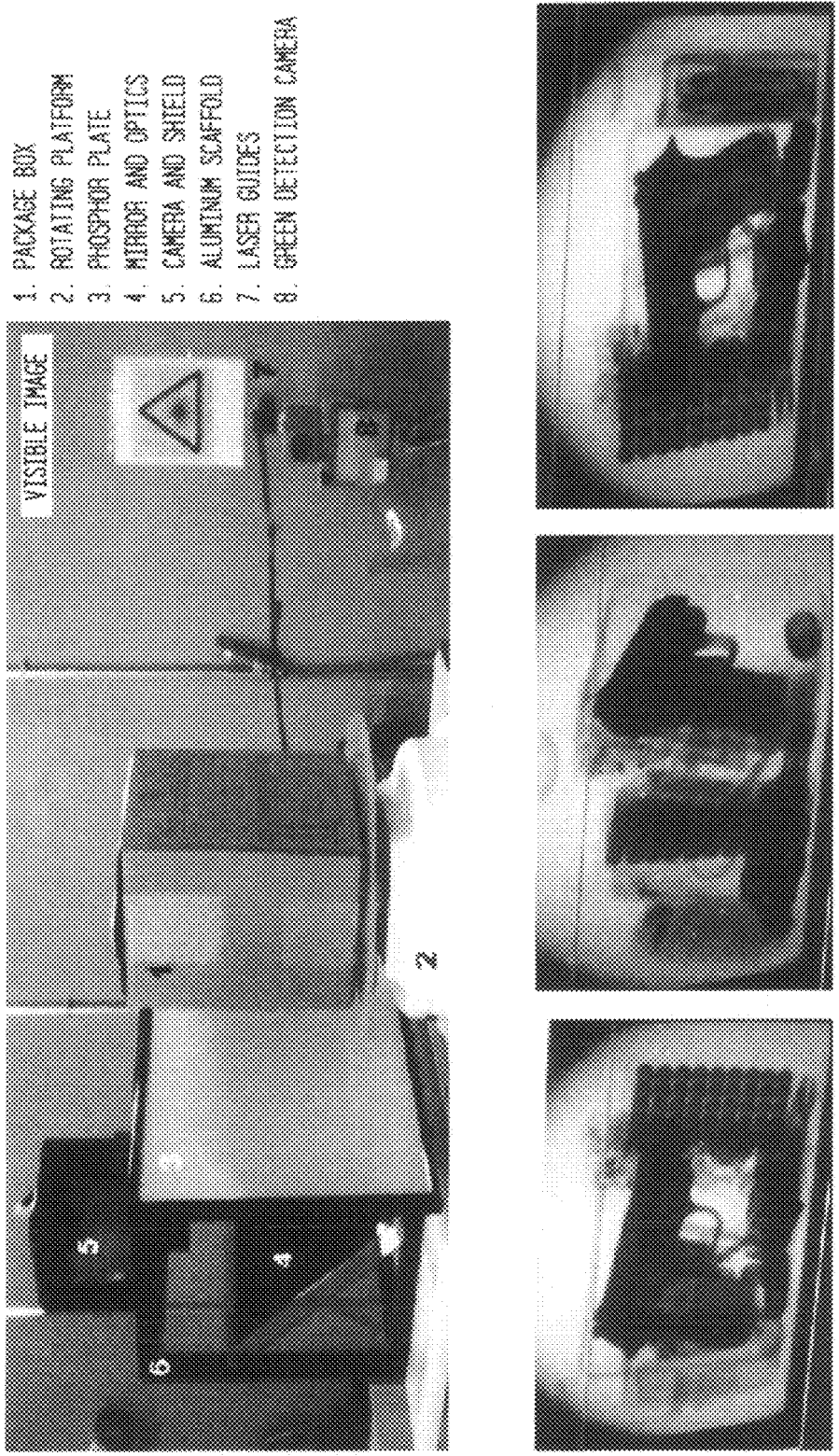
FIG. 29 depicts an exemplary small scale scanning system according to an exemplary embodiment of the present invention.

To assist an operator with configuration and calibration, in exemplary embodiments of the present invention the software can, for example, facilitate the display of images captured by the camera in which guide lines and reference marks have been added. Simple examples of this feature are shown in FIG. 29, where redlines are provided above and below a section of interest.

Exemplary Image Reconstruction Software

In exemplary embodiments of the present invention, software for reconstruction of images can include, for example, several 2D and 3D algorithms for different geometries of the scanner. Exemplary embodiments of such software have been designed following the paradigm of object-oriented programming, where each software component has been identified by seeking the common stages of filtered back projection algorithms.

An exemplary algorithm that can be used for 2D and 3D reconstruction using (i) projections from an object scan in a circular 360° path of rotation (full-scan) or (ii) 180° plus the angle of beam aperture (short-scan), can be based, for example, on the FDK method proposed by Feldkamp, Davis and Kress (1984), comprising three stages: weighting, filtering and back-projection. Process flow for the exemplary algorithm is illustrated in FIG. 46, next described.

Figure 46:
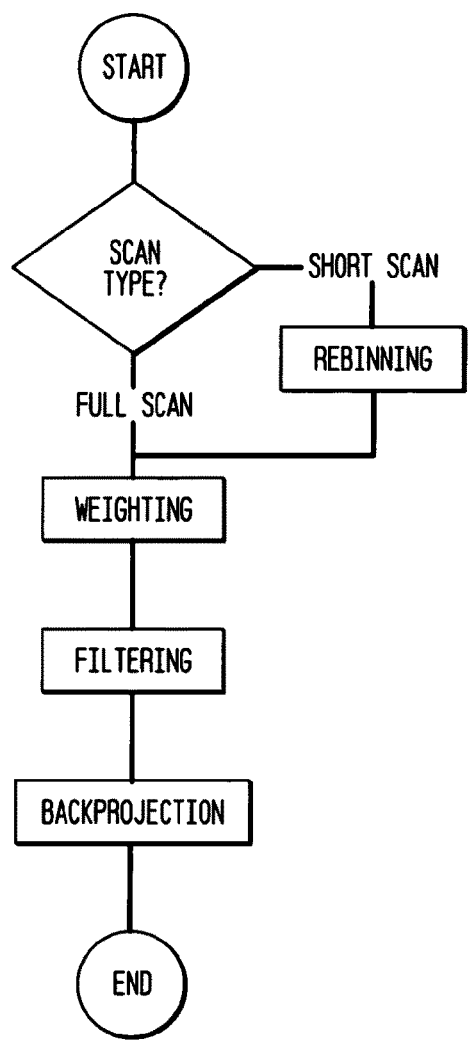
FIG. 46 is a process flow chart for an image reconstruction algorithm according to an exemplary embodiment of the present invention.

Beginning at START in FIG. 46, the scan type (long or short) can be, for example, determined. If the scan is a short scan, for example, a rebinning process can occur so as to prepare the data for subsequent processing. This process is described more fully below.

After rebinning for short scans, or initially for long scans, a weighting phase can be performed. In a weighting phase a correction factor is applied to each point of is the projection. The correction factor depends on the geometry of the detector: i.e., flat or curved, and the type of scan: i.e., full scan or short scan. In the case of an equilinear detector and a full-scan, the correction factor can, for example, be given by the following expression:

$$\frac{R}{\sqrt{R^2 + a^2 + b^2}}$$

where R is the focal length (distance between the source and the axis of rotation of the platform) and a & b are the distances from the center point of the detector to the point of projection. This correction factor can, for example, be interpreted geometrically as the cosine of the angle between the central beam and the beam of the projection.

Following such weighting, in a filtering phase, for example, a ramp filter can be applied to the results of the previous phase. The application of this filter can be, for example, done in the frequency domain where the product of the Fourier transform of the projection and the transfer function of the filter can be calculated. This can, for example, then be followed by an inverse Fourier transform or IFFT. This is done for each row of the projection independently. In exemplary embodiments of the present invention, in order to correct problems with the data it is possible to add any additional filter as may be desired.

Finally, at a back-projection stage, for example, weighted and filtered projections can be projected back (back-projected) into the reconstruction volume. In general, mathematical expressions for these calculations will depend on the geometry of the scanner. In the case of an equilinear detector and a full scan, for example, the following expression can be used, $$f_{FDK}(x, y, z) = \int_0^{2\pi} \frac{R^2}{U(x, y, \beta)^2} p^F(\beta, a(x, y, \beta), b(x, y, \beta)) \, d\beta$$

where (x, y, z) are the coordinates of the image to reconstruct, $p^F$ is the filtered projection, $\beta$ is the angle from which the projection is taken, and the factor U is given by:

$$U(x, y, \beta) = R + x \cos \beta + y \sin \beta$$

In addition to the above-described example, in various exemplary embodiments of the present invention a projection has been implemented for equiangular and parallel scanner configurations for both full-scans and short-scans.

From the various different proposed configurations, one that has been found to be particularly effective is a conical beam short-scan path. In this case the reconstruction can be done, for example, with a P-FDK (parallel FDK) or similar algorithm. This exemplary reconstruction includes a preliminary re-binning phase, which allows one to translate the fan beam geometries (fan-beam) and cone beam (cone-beam), with equilinear and equiangular detector, to parallel beam geometry. Such a process involves the rearrangement of data. During such a rebinning phase, redundancy in the data can be eliminated using, for example, the Parker weighting that is based on Smooth Sinogram Windowing.

Retroprojection Hardware

In general, filtered retro-projection algorithms have a high computational complexity, due to the fact that the amount of data to be processed is large. In general, data volume directly depends upon (i) the spectral resolution being used and (ii) the volume of the container to be scanned. Additionally, computational complexity can be high due to the available time for image reconstruction, which depends on the number of containers to be scanned by unit of time, and the number of images to be taken.

To minimize processing times, or even to work in real time at a reasonably economical cost, in exemplary embodiments of the present invention, an exemplary system can include a Graphics Processing Unit (GPU). This is a multiprocessor system with several cores each, which allows parallel processing speed in the multi-core GPU. Using such specific hardware has in turn allowed the development of specific software using massive data parallel processing techniques with low coupling dependence among them. This implies that the speedup, or acceleration, depends only on the number of cores. Using a software design based on threads, blocks and grids, in exemplary embodiments of the present invention it is possible to include one or several GPU units. This permits scaling the devices and adapting them to different configurations according to needed scanning speeds and allowed equipment costs.

In exemplary embodiments of the present invention computer time reduction can also be achieved in the filtering phase by the use of a CUFFT library that can, for example, provide better performance than the others available, due to the use of a graphics card. In this connection it is noted that an exemplary CUFFT, such as the NVIDIA® CUDA™ (computed unified device architecture) Fast Fourier Transform (FFT) library, can be used. As known in the art, the FFT is a divide-and-conquer algorithm for efficiently computing Discrete Fourier Transforms of complex or real-valued data sets, and is one of the most important and widely used numerical algorithms, with applications that include computational physics and general signal processing.

Visualization Software

In exemplary embodiments of the present invention, software can be provided to visualize the reconstructed objects. Such visualization can include, for example, 2D and 3D visualization for each of fan-beam and cone-beam geometries. In exemplary embodiments of the present invention, a color can be assigned to each one of the pixels or voxels, as the case may be, depending upon its density value. This can facilitate, for example, quick inspection of objects adjacent to each other having markedly different densities, as described below.

In exemplary embodiments of the present invention such visualization software can further allow an operator, for example, (i) to zoom the image with an amplification factor and a size adequate to enhance details of a region of interest; (ii) to shift and to rotate the image, to allow different views of the object; (iii) to cut the image in planar slices, to eliminate non-relevant portions, such as the container walls; (iv) to adjust the contrast and brightness of the image; (vi) to define densities that finally will be shown as transparent, to exclude non-interesting elements—such as air—or to select the range of densities to be displayed, and thus (vii) to introduce a density window to be displayed by giving the density span and the density value at the center.

In exemplary embodiments of the present invention, in order to provide a global view of the different densities of various objects inside a container, there can, for example, be provided a software module using artificial intelligence techniques (related with Kohonen's Self Organized Maps) that can, for example, classify the inspected substances into clusters according to their densities.

With proper training of an operator, this can, for example, allow the detection of certain substances inside the container as well as their exact localization. Moreover, for a better visualization, the operator can, for example, choose a density window and assign false colors to this range.

In order to apply visual effects to the images, such as, for example, textures, light, shadows, etc., shaders written in GLSL (OpenGL Shading Language) can, for example, be used. Since such shaders can be run on the GPU, an acceleration of the graphic visualization of the objects can, for example, be achieved. Since the GPU has a multi-core design, it can directly perform parallel processing on the image pixel which can result in an increase in processing efficiency.

In various exemplary embodiments built by the inventors, all software modules (Image Reconstruction Software and Visualization Software) have been developed using standard C++, and by using libraries available on a wide variety of platforms. Thus, such software can be run under Windows, Linux, and, it is believed, on an Apple Macintosh platform. in exemplary embodiments of the present invention implementation of the visualization software can, for example, use OpenGL in a reusable module.

Exemplary Systems and Results

Figure 30:
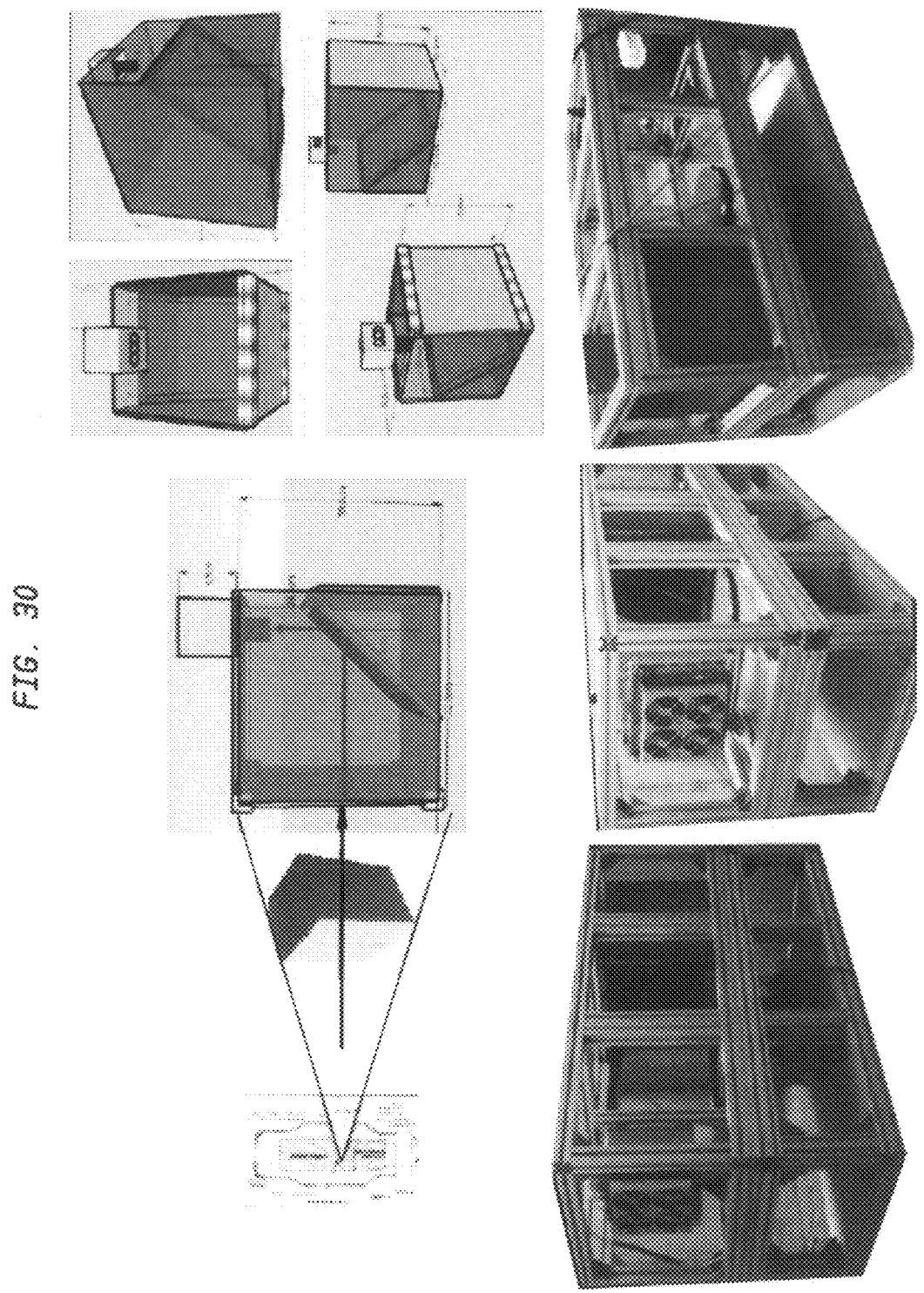
FIG. 30 depicts various design diagrams of an exemplary detector structure similar to that of FIG. 29, with the X-ray source built in to the system, and also shows images of an exemplary system built according to the depicted design.
Figure 31:
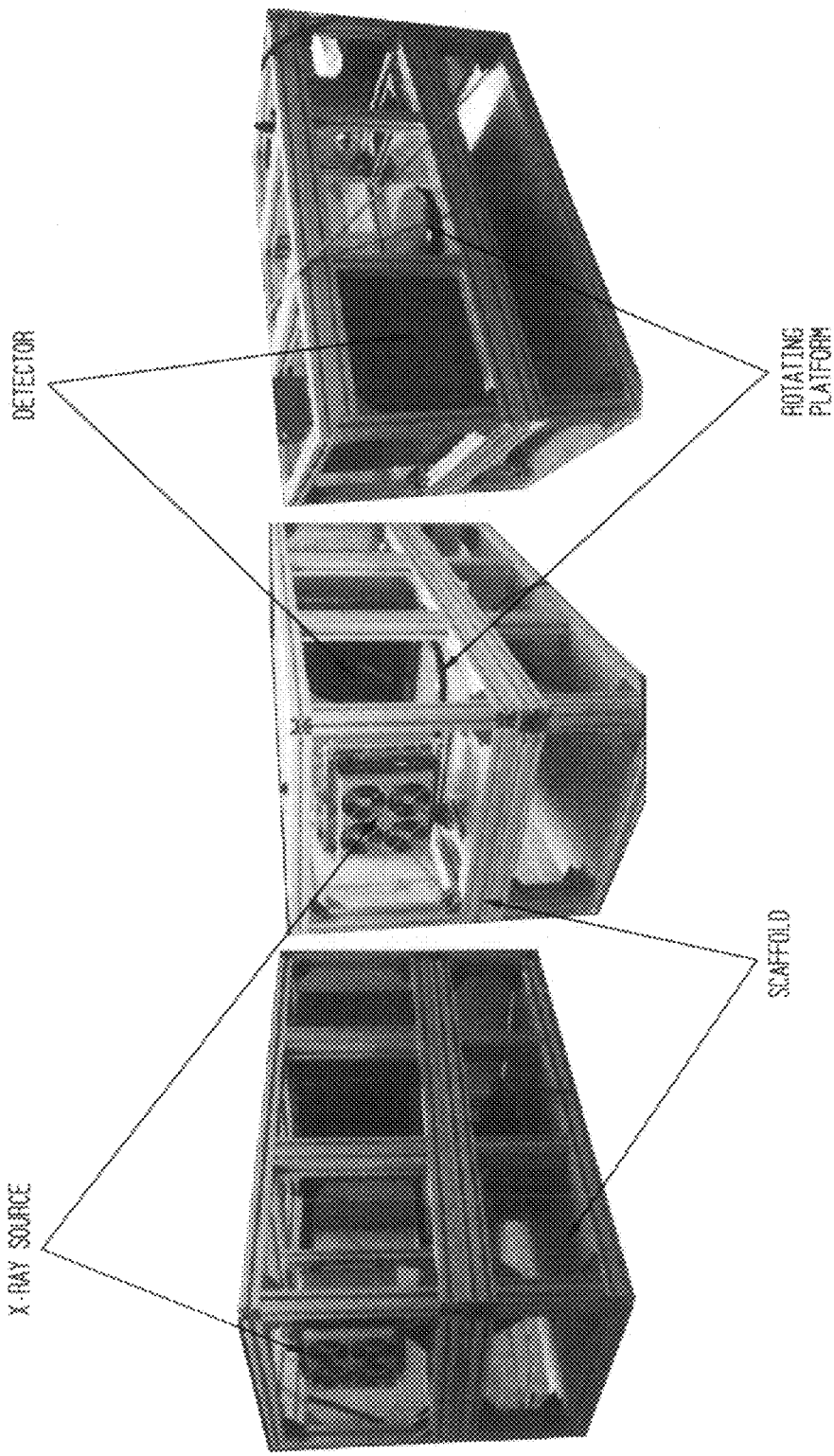
FIG. 31 shows further details of the exemplary detector structure of FIG. 30.

FIGS. 29-31 depict an exemplary small scale scanner according to an exemplary embodiment of the present invention. With reference thereto, such an exemplary small scanner can have, for example, five basic parts:

1. An X-ray source. If the system is dedicated to a single use, such as, for example, airport safety, the X-ray source can be specific to a given voltage and amperage, thus simplifying the system. Example single use energies for X-ray sources include plastics industry—up to 60 KeV, airport luggage security—up to 100 KeV, aircraft structures—up to 120 KeV, welding industry—up to 150 KeV; small cargo security—up to 250 KeV, and medium cargo security—up to 350 KeV. It is noted that more than 450 KeV is impossible to obtain with a normal X-ray tube, and intensities greater than 1 MeV need a linear accelerator system.

2. A Rotating platform with the ability to speed regulation and docking systems with motion capture. In exemplary embodiments of the present invention a rotating platform can have a separate motor that is associated with an encoder and a retarder with a digital speed controller that precisely selects the lap time and which is coupled to the scanning system. A failure in this link will generally make the images appear defective or blurred.

3. A Detector, comprising (i) a phosphorus panel as described above, synthesized and deposited in a thin aluminum layer; (ii) mirror, positioned at an angle and distance as described above, (iii) intensified CCD camera focused on the mirror to capture as many of the photons as possible, (iv) "scaffold" structure opaque to light and rigid to avoid any distortion or vibration.

4. A Rigid support structure.

5. Hardware and software for imaging acquisition.

In exemplary embodiments of the present invention, a typical scanning operation can be implemented as follows. An exemplary system can have, for example, a modulated X-ray system that allows control of the intensity and output voltage of the X-ray beam. Using such a system, for example, appropriate optimum is values for voltage and amperage can be experimentally obtained for each type of material, including, for example, plastic, aluminum, steel, etc. After selecting the best balance between voltage and amperage to obtain the highest quality in the resulting images, an X-ray source tube can be obtained for a given scanning milieu.

Using the chosen X-ray source, an appropriate shot of X-rays, optimally adjusted in voltage and amperage, can be emitted towards a container, box or object. The X-rays will thus be sent through the object(s) to be scanned and will then hit the phosphor plate panel. During this process, a portion of the original x-rays are absorbed by the contents of the container, depending on the component density (and thus the linear attenuation coefficient).

The X-rays that hit the phosphor panel are transformed into light (or, for example, other electromagnetic radiation). Once the X-rays passing through the phosphor panel are transformed to such light, a mirror can be used, for example, to focus this light to an ICCD, for example. Such an ICCD can then transmit the acquired signal to a computer or data processor that can, for example, generate a grayscale image based on the received light (itself directly related to the X-rays received by the phosphor panel). The grayscale mage can then, for example, be analyzed so as to differentiate structures and shapes depending on their composition.

This process can be repeated for each of various platform rotation angles. At the end of such repetitions, the computer or data processor will have received, for example, hundreds of images that can then be fused and reconstructed into a single three-dimensional image that contains all the acquired information regarding the scanned object(s).

FIG. 29 thus depicts an exemplary small scanner and an exemplary package box 1 that was scanned using it. The box sits on a rotating platform 2, and X-rays are sent through the box 1. Some of these X-rays pass through to interact with a phosphor plate 3. The phosphor plate generates light signals as a result of its interaction with the X-rays, and the light can be reflected via mirror and optics 4 to camera and shield 5. The camera is here provided on aluminum scaffold 6. As also shown in FIG. 29, laser guides 7 can be used. Laser guides 7 are a laser emitting light that can be used, for example, to determine the correct position and alignment of the object to be scanned, and to further ensure that it is centered in front of the axis of the X-ray beam. Finally, green detection camera 8 is a CCD camera that can image the green light emitted from the phosphor panel after its interaction with the received X-rays. Thus, both laser guides 7 and green detection camera 8 are control and positioning mechanisms used to properly position and orient the object or box to be scanned. The X-ray source is not shown; it is positioned outside the diagram at the right.

At the bottom of FIG. 29 are shown three example images that were obtained of package box 1, showing, inter alia, a gun inside. As is known, CT provides, as opposed to a particular image, a video with 360° projections. FIG. 29 shows a selection of some of the frames of this video at random positions, which corresponding roughly to 0°, 90° and 180° of rotation (i.e., of rotating platform 2).

FIG. 30 shows various design diagrams of an exemplary detector structure similar to that shown in FIG. 29, with the X-ray source built in to the system (upper panels). FIG. 30 also shows images of an exemplary system built according to the depicted design (lower panels). FIG. 31 shows further details of the exemplary detector structure of FIG. 30.

In exemplary embodiments of the present invention, objects within packages or containers can be identified based on their atomic number. This process is based upon the "mass attenuation co-efficient", next described. To identify materials the physical principle of "mass attenuation coefficient" can be used to measure to what extent a chemical species or substance absorbs or scatters light at a given wavelength, per unit mass.

In addition to visible light, mass attenuation coefficients can be defined for other electromagnetic radiation (such as X-rays). The defining equation for the mass attenuation coefficient is essentially a different way to write the Beer-Lambert law. The Beer-Lambert law is normally written as $$I = I_0 e^{-\mu l}$$

Where:
$I_0$ is the original intensity of the beam;
I is the intensity of the beam at distance l;
e is Euler's number, about 2.718; and
$\mu$ is the attenuation coefficient.

The attenuation coefficient is a quantity that characterizes how easily a material or medium can be penetrated by a beam of energy. I.e., how transparent or opaque it is to that type of energy. A large attenuation coefficient means that the beam is quickly "attenuated" (weakened) as it passes through the medium, and a small attenuation coefficient means that the medium is relatively transparent to the beam. The attenuation coefficient describes the extent to which the intensity of an energy beam is reduced as it passes through a specific material.

Figure 32:
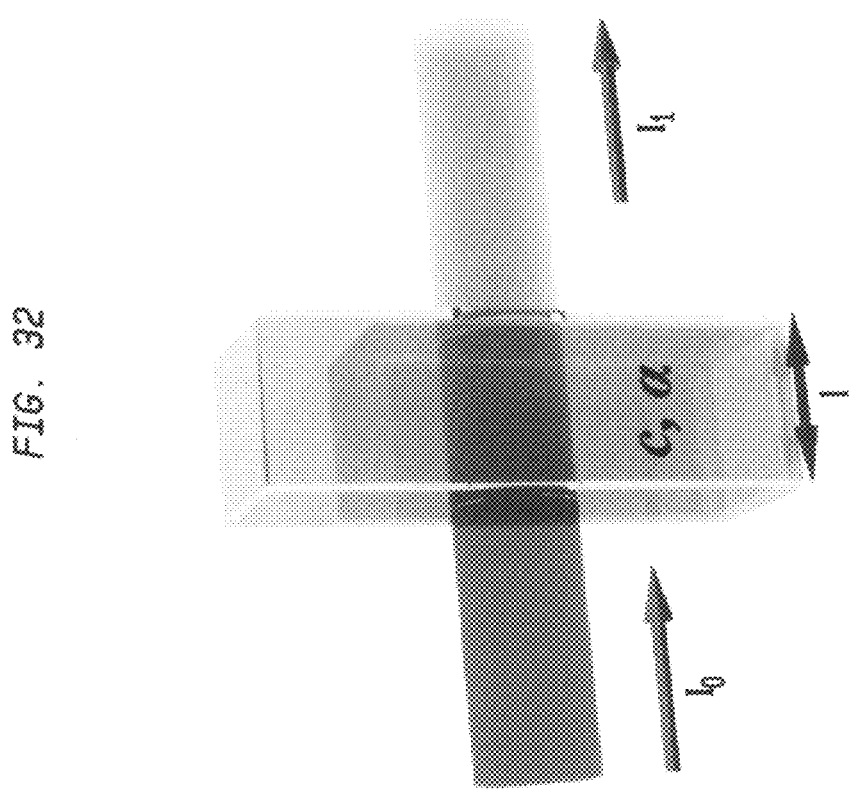
FIG. 32 depicts an illustration of the mass attenuation co-efficient, which is the basis of exemplary object identification algorithms according to exemplary embodiments of the present invention.

FIG. 32 illustrates the attenuation of incident radiation $I_0$ by an object of thickness I, having attenuation coefficient c and density $\alpha$. As shown, the intensity of the radiation that exits the object is $I_1$. $I_1$ is always less than or equal to $I_0$.

The linear attenuation coefficient is dependent upon both the type of material and the energy of the radiation. Generally, for electromagnetic radiation, the is higher the energy of the incident photons and the less dense the material in question, the lower the corresponding linear attenuation coefficient will be. Given this fact, objects and their chemical compositions can be distinguished based on their respective attenuation coefficients.

Exploiting this fact, FIGS. 33-37 depict exemplary examples of objects scanned with the exemplary small scanner of FIGS. 29-31 and the CT images generated from those scans. Using these images, the scanned objects can be identified by Z number.

Figure 33:
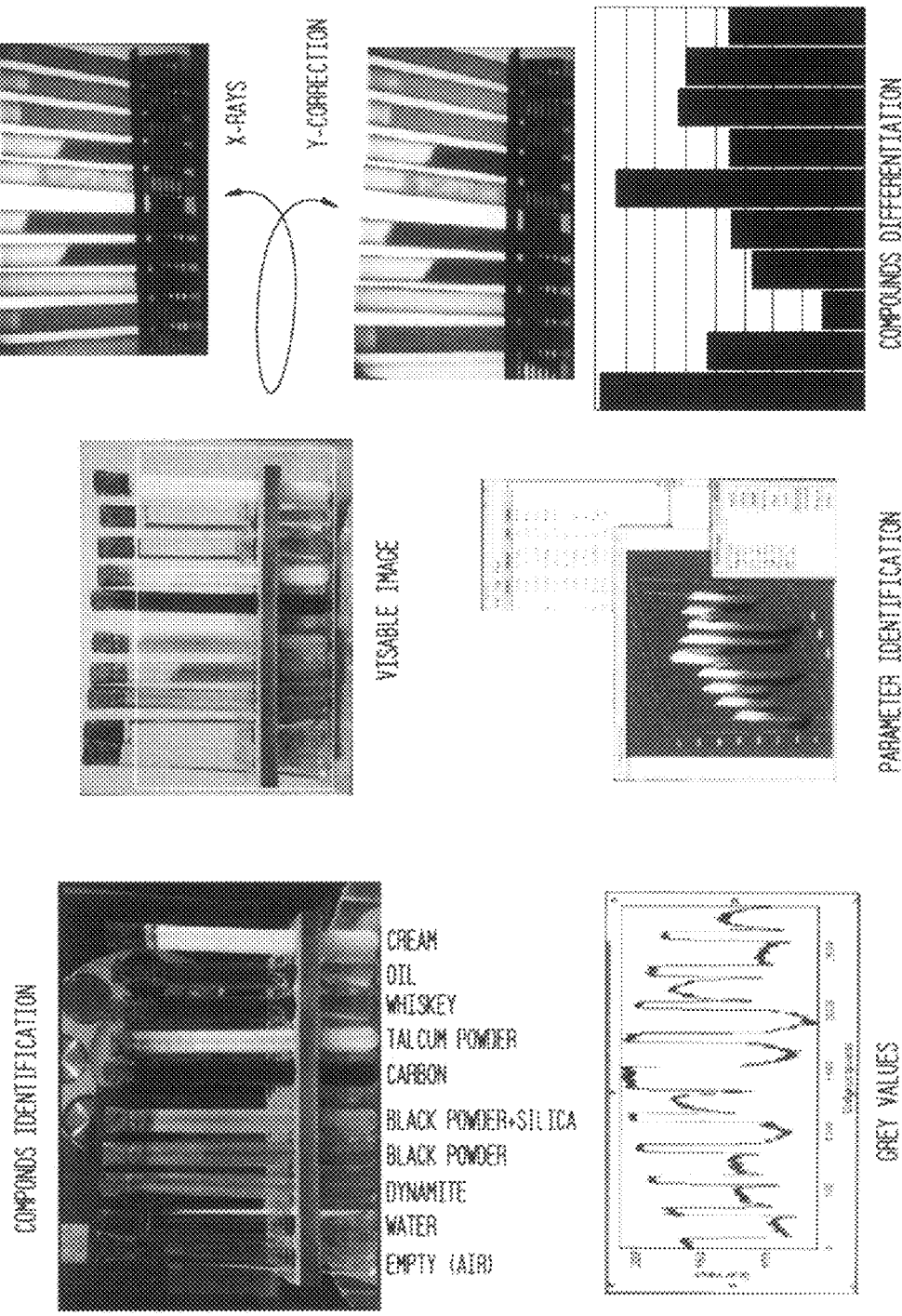
FIG. 33 depicts an initial test of compound separation according to an exemplary embodiment of the present invention.

With reference thereto, FIG. 33 depicts an initial test of compound separation. In this test, various test tubes were filled with materials of different known densities. The different densities were identified based on attenuation co-efficient, the known energy of the incident X-rays, and use of a system database containing records associating attenuation coefficients to known compositions, as shown.

Figure 34:
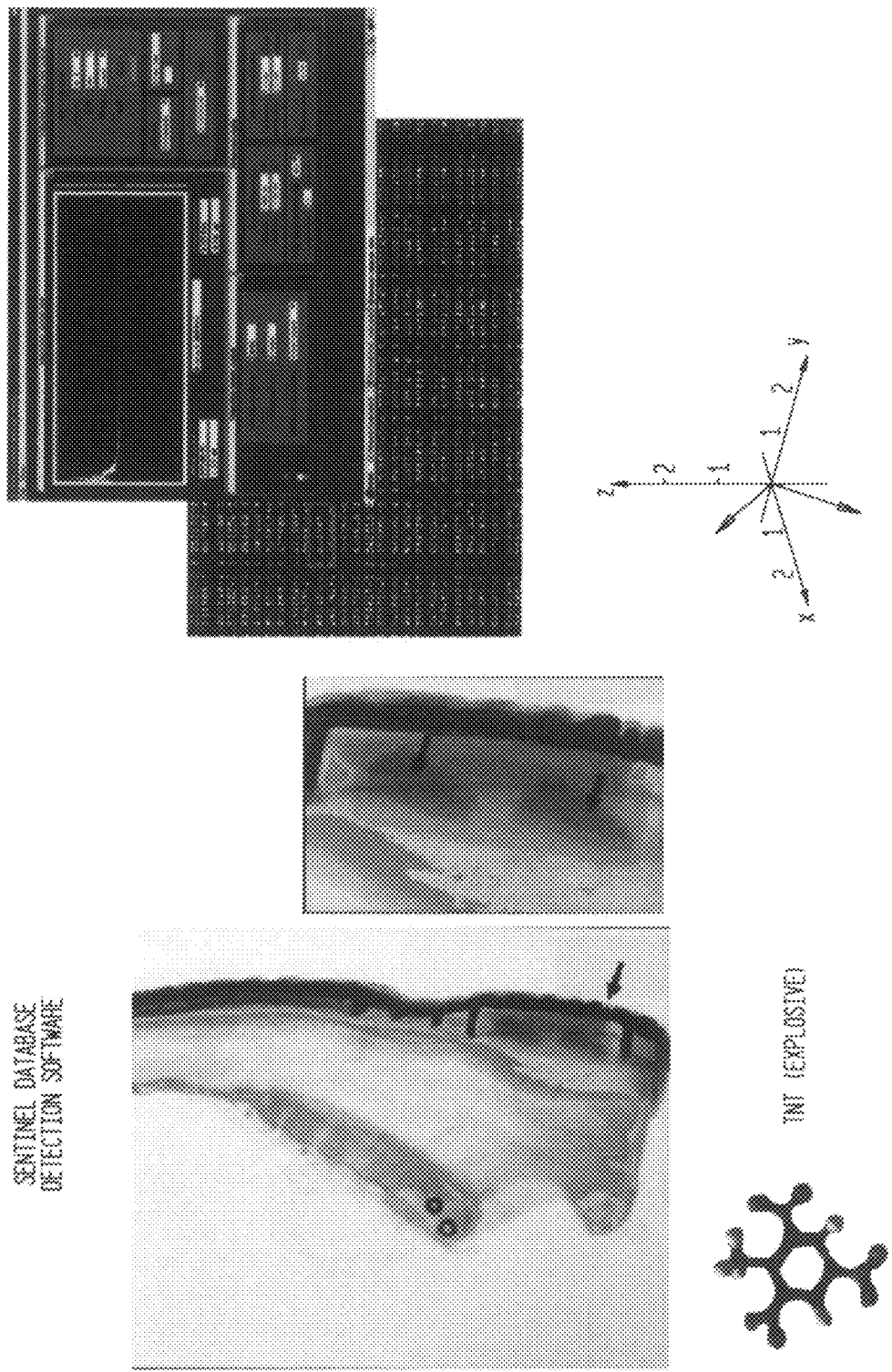
FIG. 34 depicts an exemplary normal use of a system database according to an exemplary embodiment of the present invention; here a shoe is studied with an exemplary X-ray scanning system.

FIG. 34 illustrates a common exemplary use of such a system database. In this case, a shoe is studied with an exemplary X-ray scanning system, and the values of linear attenuation coefficients are compared with those values stored in a system database. A positive match was found. Thus, CT scanning allows identifying the test compound as being in the sole of the shoe and its composition as TNT.

Figure 35:
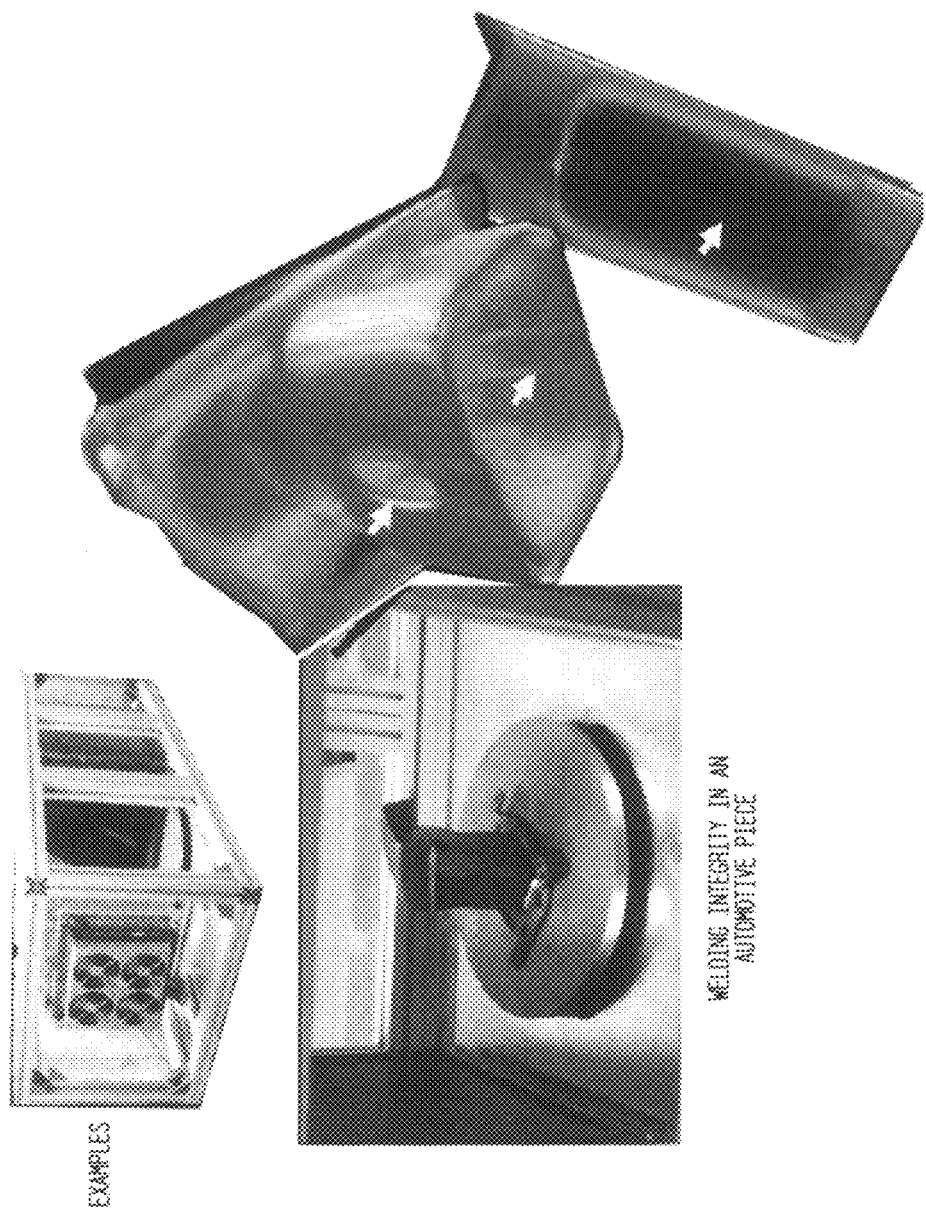

FIGS. 35-38 depict several real examples of objects scanned and identified using an exemplary small scale scanning system, as described above. Thus, FIG. 35 depicts examination of welding integrity in an automotive piece. Here, for example, what is of interest is whether welds have been completed correctly. The test is whether the welding material is homogeneously distributed and if all welds (known from a welding schedule) appear where and how they are supposed to be. Thus, one obtains a map of the correct welding patterns and can, for example, compare it with the image obtained from the scanner. In FIG. 35 there can be seen a continuous and homogeneous linear structure where the weld was found, corresponding to a proper weld.

FIG. 36 illustrates identification of a hidden detonating fuse (pointed to by the arrows) in a bottle. It is noted that a fuse does not have a determined attenuation coefficient, so detection involves detecting a large difference between the detonator and its surrounding material (as described above). X-ray based scanning systems according to exemplary embodiments of the present invention can very easily sense such a variation of density. The depicted colors are generated by exemplary visualization software and correspond to different densities (in this particular mapping yellow corresponds to denser material, and thus corresponds to the glass bottle, whereas the detonator appears with different colors (blue-green)).

Figure 39:
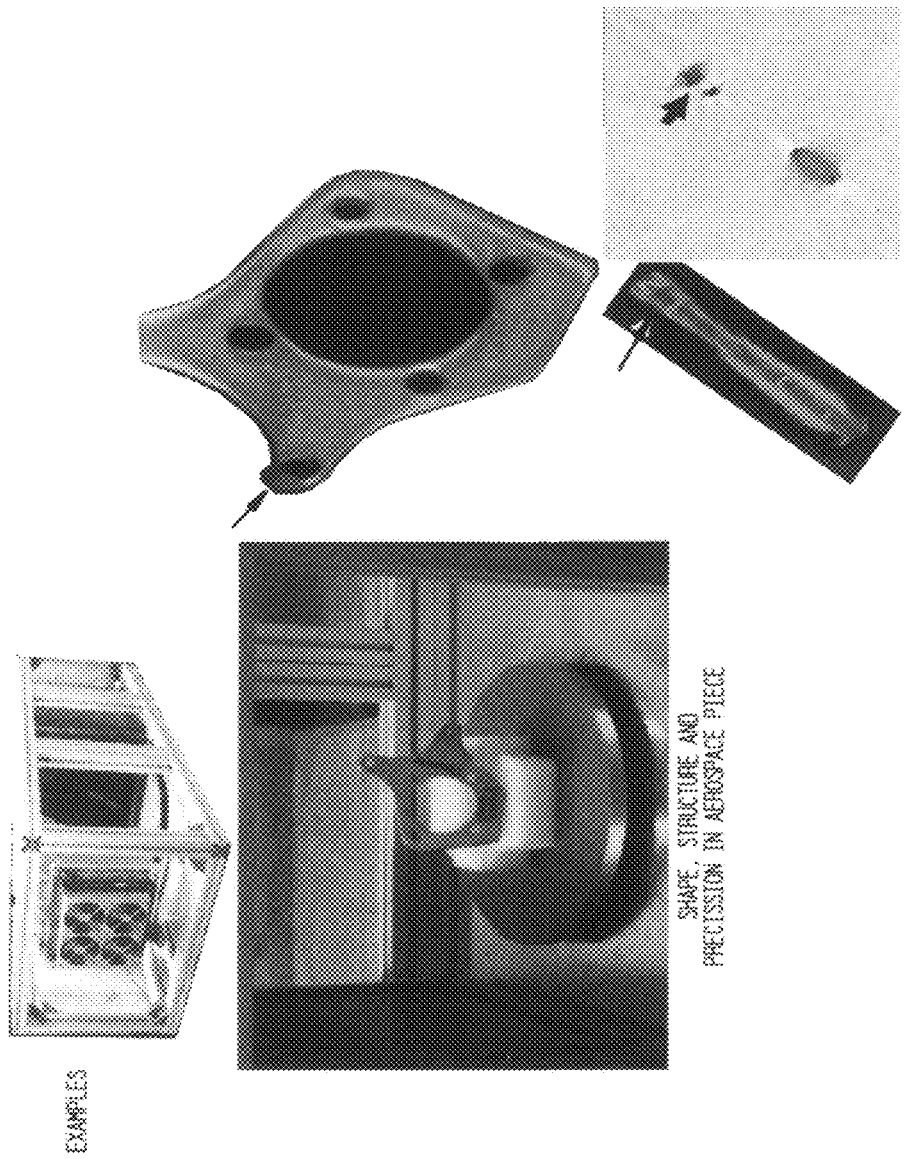

FIG. 37 depicts hidden depleted plutonium in a food package, and FIG. 38 depicts hidden dynamite in a bottle, and FIG. 39 depicts examination of shape, structure and precision in aerospace piece.

FIGS. 40-44 depict an exemplary large scale cargo system, suitable for scanning of, for example, maritime containers or other large transportation containers. Such exemplary scanners can use, for example, a dual linear accelerator capable of outputting 3 MeV and 6 MeV as a radiation source. A dual linear accelerator is a system capable of shooting two fixed energies, here 3 MeV and 6 MeV. These energies are not random, rather, 3 MeV is more than the minimum required to pass through a container and be able to scan and detect different materials and 6 MeV is set as the maximum to avoid ionization phenomena in the materials contained within the container. According to international guidelines this maximum energy is 8 MeV, so to operate within a safety margin, a maximum energy of 6 MeV was chosen. Shooting the dual form allows one to see "in colors", as described above, i.e., to look at two energies to distinguish materials that behave differently with one or another energy. For example, two very similar materials to 3 MeV absorption can be completely different in the case of 6 MeV interaction, thereby improving the resolution and efficiency of the system.

Figure 40:
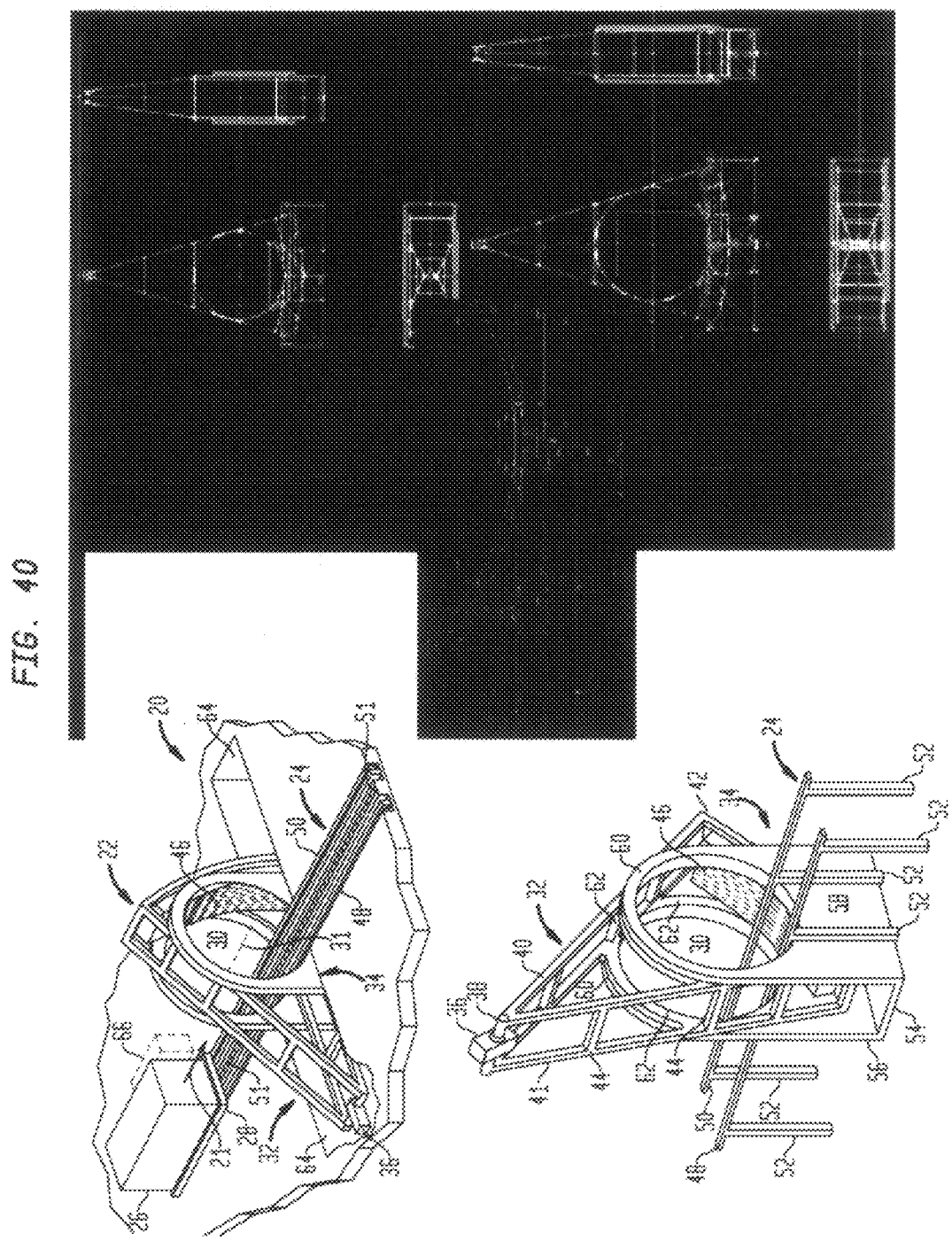
FIGS. 40-44 depict an exemplary large scale cargo system, suitable for scanning of, for example, maritime containers, according to an exemplary embodiment of the present invention.
Figure 41:
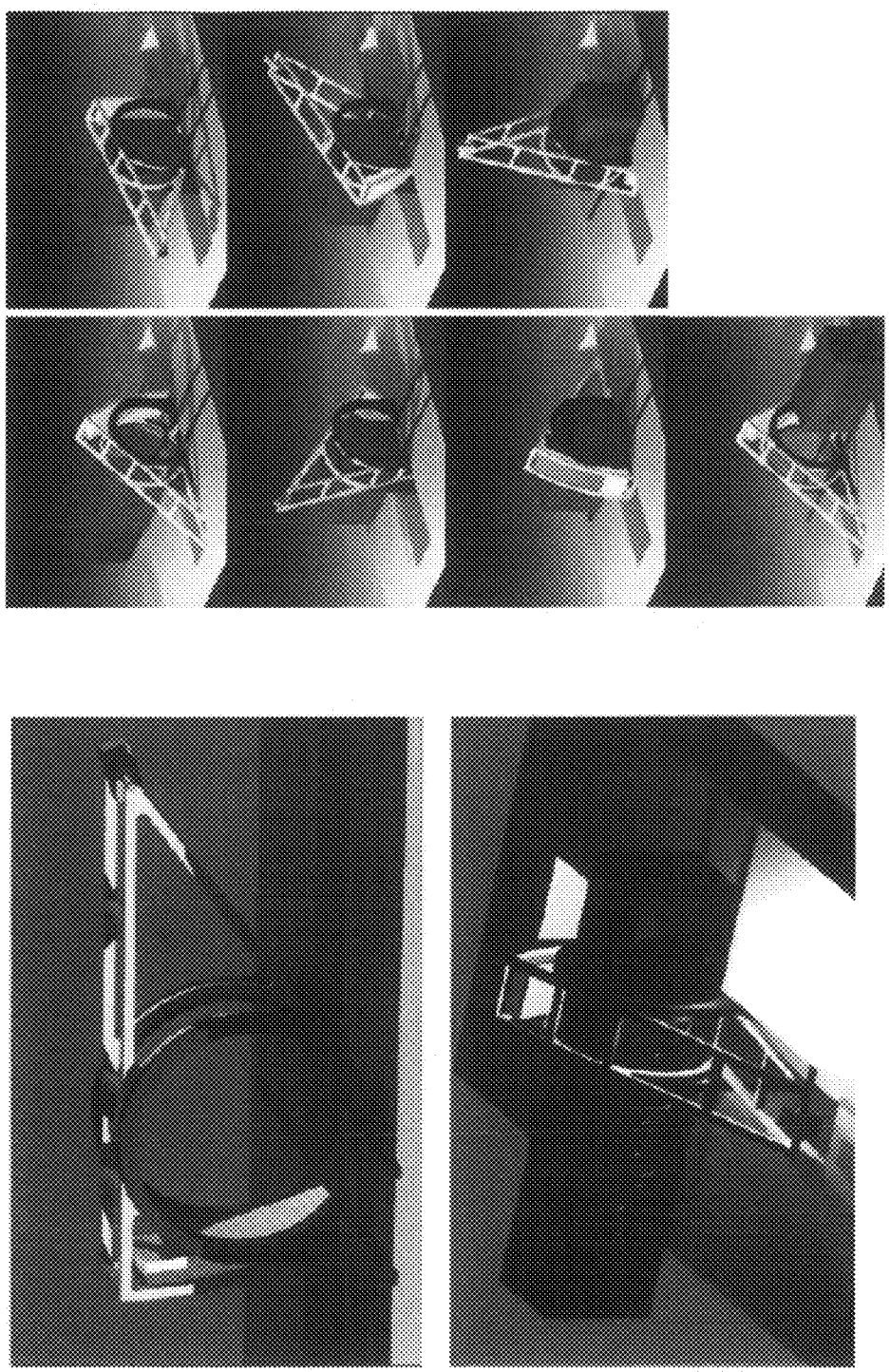
Figure 42:
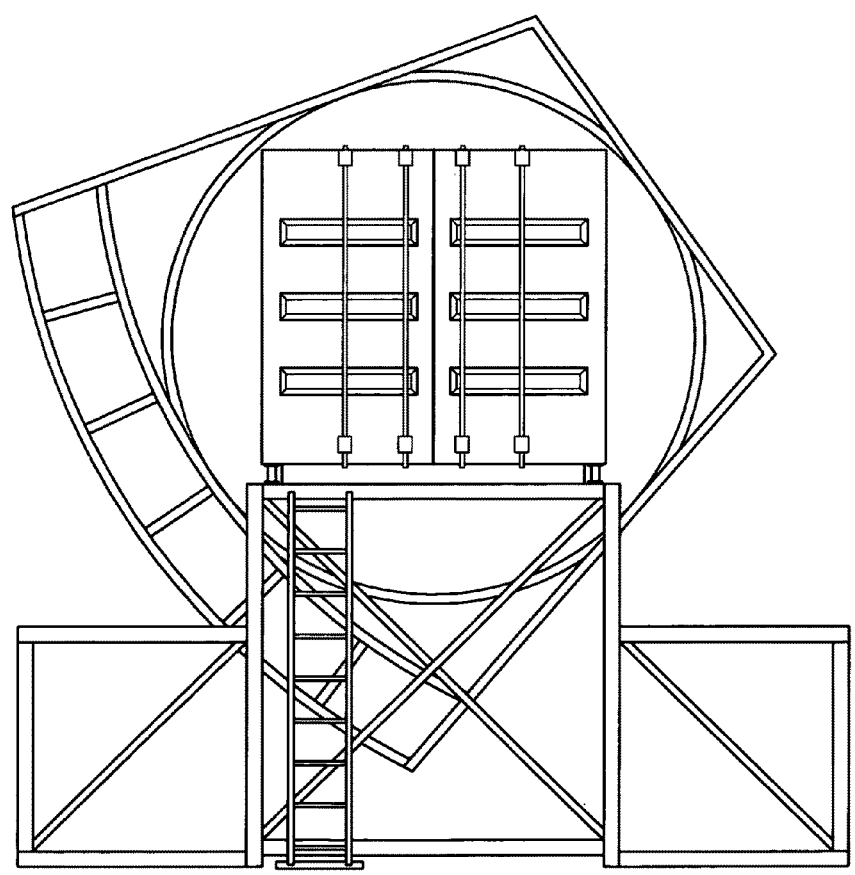
Figure 43:
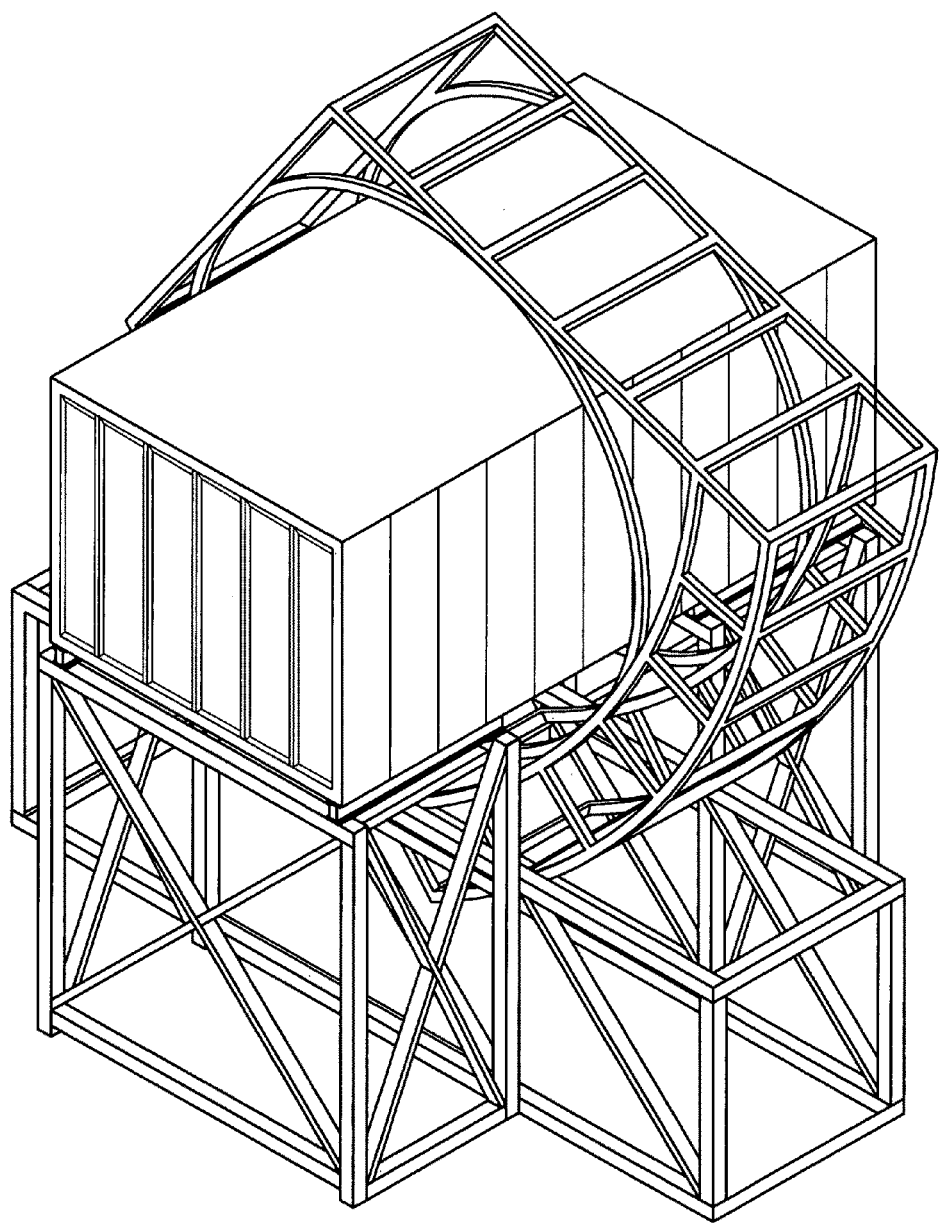
Figure 44:
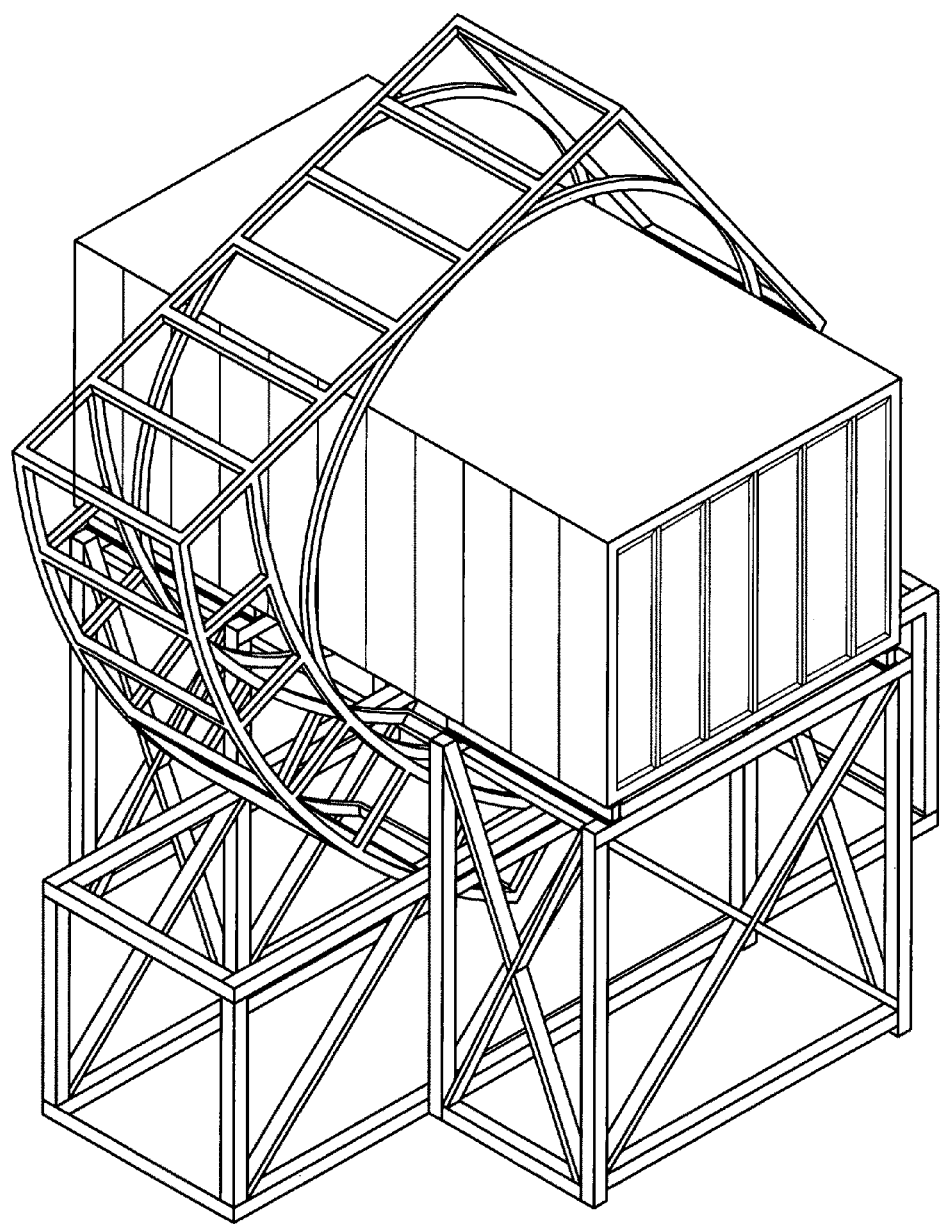

Thus, FIGS. 40 and 41 depict exemplary initial designs, and FIGS. 41-44 depict a full scale prototype of such an exemplary large scale scanning system.

Figure 45:
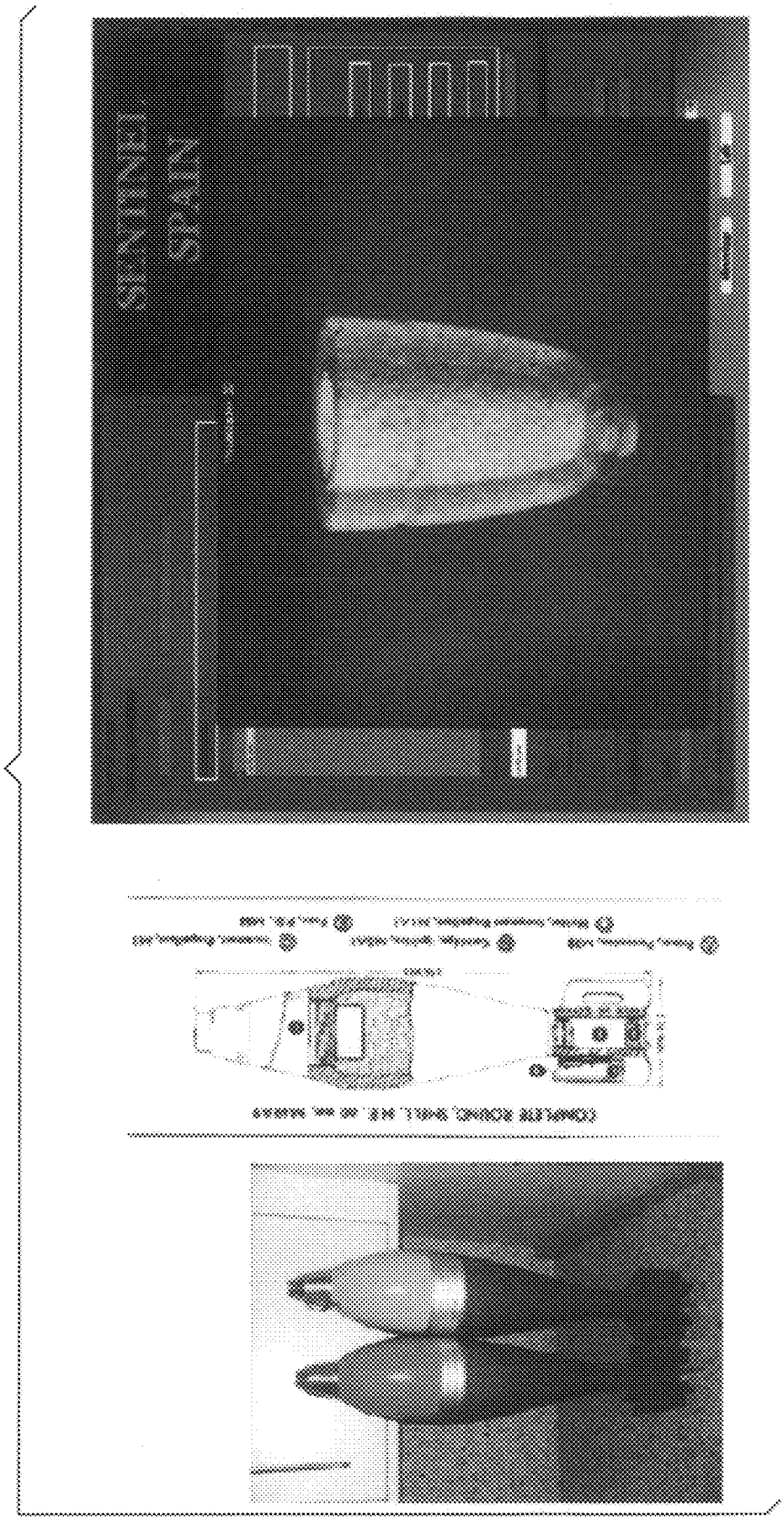
FIG. 45 depicts exemplary test results using such an exemplary large scale scanner to see inside bombs, and identify the explosive material.

Finally, FIG. 45 depicts exemplary test results using the exemplary scanner, with a 3 MeV linear accelerator as a radiation source, in an explosives manufacturing company. Here the scanner was able to see inside some bombs, and identify the explosive material (detect air bubbles). The detection system included a portable detector system comprising a detector with the phosphor panel, a CCD camera, scaffold, mirror and shielding, and a laptop computer running software. The X-ray source used was a Varian 3 MeV lineal accelerator. The right panel of FIG. 45 shows the bombs scanned on a rotating platform, yellow corresponding to the bomb external structure and pink, the explosive, observed air bubbles in the explosive.

The present invention has been described in terms of various exemplary embodiments, but is more broadly applicable as will be understood by those skilled in the art. The scope of the invention is only limited by the following claims.

What is claimed:

1. An inspection system, comprising:
a scanner support structure with an opening;
a rotor mounted on said scanner support structure, said rotor mounted so as to rotate about an axis of rotation running through the opening, said rotor including:
an X-ray source, and
a detector, the detector being positioned to receive X-rays emitted from said X-ray source; and
a drive device configured to move a container through said opening, a braking system configured to stop the rotation of said rotor at each of two stop positions and reverse the direction of rotation of said rotor at each of said stop positions, and move said container from a first reading position to a second reading position during the deceleration, stopping, and acceleration of said rotor at each of said stop positions.

2. The inspection system of claim 1, wherein said detector comprises a plate that directly converts incident X-rays into electromagnetic radiation of a wavelength differing from the wavelength of the X-rays.

3. The inspection system of claim 1, wherein said opening is one of: (i) greater than or equal to 3 meters in diameter, (ii) greater than or equal to 3.5 meters in diameter, (iii) greater than or equal to 4 meters in diameter, (iv) greater than or equal to 5 meters in diameter, (v) less than or equal to 2 meters in diameter and (vi) less than or equal to 1.5 meters in diameter.

4. The inspection system of claim 1, further comprising a data processor for processing the X-rays received by said detector to generate 2D and/or 3D images of at least some of the contents of a container placed in the opening.

5. The inspection system of claim 4, wherein said 2D and/or 3D images are color enhanced by the data processor.

6. The inspection system of claim 5, wherein said color enhancing assigns different colors to objects, as a function of their density.

7. The inspection system of claim 1, wherein said opening is of a size and shape to allow a transportation container to pass through it.

8. The inspection system of claim 1, wherein said detector comprises a coating on said a substrate, said coating comprising a mixture of:
a phosphor compound that converts X-rays into electromagnetic radiation of a wavelength differing from the wavelength of said X-rays; and
a protective compound that provides protection to said phosphor.

9. The inspection system of claim 8, wherein said coating further comprises a reflector compound that amplifies said electromagnetic radiation.

10. The inspection system of claim 9, wherein said phosphor compound is selected from the group consisting of $CaWO_4$, $YTaO_4$, $Gd_2O_2S$ and $LaOBr$.

11. The inspection system of claim 9, wherein said phosphor compound is doped or activated with rare earth elements.

* * * * *